United States Patent [19]

Earls et al.

[11] Patent Number: 5,270,404

[45] Date of Patent: Dec. 14, 1993

[54] CURABLE COMPOSITIONS OF MESOGEN-CONTAINING ADVANCED EPOXY RESINS AND CURING AGENTS THEREFOR

[75] Inventors: Jimmy D. Earls; Robert E. Hefner, Jr.; Paul M. Puckett, all of Lake Jackson, Tex.

[73] Assignee: The Dow Chemical Company, Midland, Mich.

[21] Appl. No.: 916,305

[22] Filed: Jul. 17, 1992

Related U.S. Application Data

[63] Continuation-in-part of Ser. No. 616,538, Nov. 21, 1990, abandoned, which is a continuation-in-part of Ser. No. 553,491, Jul. 13, 1990, abandoned, which is a continuation-in-part of Ser. No. 298,431, Jan. 17, 1989, abandoned.

[51] Int. Cl.$^5$ ............... C08G 59/06; C08G 59/40; C08G 59/46; C08L 63/02
[52] U.S. Cl. ............... 525/481; 525/482; 525/523; 525/526; 525/528; 525/533; 528/96; 528/97; 528/98; 528/99; 528/100; 528/101; 528/104
[58] Field of Search ............... 525/523, 526, 528, 533, 525/481, 482; 528/96, 97, 98, 99, 100, 101, 104

[56] References Cited

U.S. PATENT DOCUMENTS

| | | | |
|---|---|---|---|
| 2,698,315 | 12/1954 | Greenlee | 528/219 |
| 3,383,360 | 5/1988 | Harrison . | |
| 3,408,407 | 10/1968 | Cotter et al. | 528/98 |
| 4,624,872 | 11/1986 | Stuetz . | |
| 4,694,066 | 9/1987 | DeMartino et al. . | |
| 4,762,901 | 8/1988 | Dheim et al. . | |
| 4,764,581 | 8/1988 | Müller | 528/100 |
| 4,877,858 | 10/1989 | Hachiya et al. . | |
| 5,043,192 | 8/1991 | Jones et al. . | |
| 5,149,730 | 9/1992 | Murata | 525/481 |

FOREIGN PATENT DOCUMENTS

| | | |
|---|---|---|
| 348873 | 1/1990 | European Pat. Off. . |
| 355772 | 2/1990 | European Pat. Off. . |
| 361853 | 4/1990 | European Pat. Off. . |

OTHER PUBLICATIONS

C. Noel & P. Navard, Prog. Polym. Sci., 16, 55-110 (1991).

C. K. Ober & R. A. Weiss, "Liquid Crystalline Polymers," R. A. Weiss and C. K. Ober ed., ACS Symp. Series 435, Am Chem Soc. Washington, D.C., pp. 1-13 (1990).

ACS Symposium Series 114, Chapter 17,00. 259-262, (given Sep. 1978, at th 176th meeting of the American Chemical Society by James R. Griffith).

Derwent Abstracts: 90-143153/19 "Handbook of Epoxy Resins", Lee and Neville, McGraw-Hill 1967, pp. 13-19.

Derwent Publications Ltd., London, GB & JP-A-63 169 619; Jul. 13, 1988; Chemical Patents Index Basic Abstracts, Journal, Section A, week 8834, 19th Oct. 1988, A0285, No. 88-237750/34.

Primary Examiner—John C. Bleutge
Assistant Examiner—D. R. Wilson

[57] ABSTRACT

Compositions comprising epoxy resins containing one or more rodlike mesogenic moieties per molecule are cured with curing agents which will normally cure epoxy resins. These curable compositions can be oriented by the application of an electric field, magnetic field drawing and/or shear flow prior to and/or during curing. The resultant cured products exhibit an improvement in one or more physical or mechanical properties as compared to a like epoxy resin system which does not contain any rodlike mesogenic moieties.

16 Claims, No Drawings

CURABLE COMPOSITIONS OF MESOGEN-CONTAINING ADVANCED EPOXY RESINS AND CURING AGENTS THEREFOR

CROSS-REFERENCE TO RELATED APPLICATIONS

This application is a continuation-in-part of application Ser. No. 7/616,538 filed Nov. 21, 1990 (now abandoned) which is a continuation-in-part of application Ser. No. 07/553,491 filed Jul. 13, 1990 (now abandoned) which is a continuation-in-part of application Ser. No. 07/298,431 filed Jan. 17, 1989 (now abandoned) all of which are incorporated herein by reference in their entirety.

FIELD OF THE INVENTION

The present invention pertains to epoxy resins containing rodlike mesogenic moietie(s), curable compositions and cured compositions thereof.

BACKGROUND OF THE INVENTION

Epoxy resins are useful in many applications such as coatings, laminates, composites, adhesives, castings and the like. In each of these applications, it is desirable to have epoxy resins with an improvement in any one or more of their physical and/or thermal and/or chemical resistant properties.

The present invention provides a method for improving one or more of these properties by incorporating into the polymer chain of the epoxy resin one or more rodlike mesogenic structure(s). These epoxy resins exhibit ordering of the molecular chains in the melt phase and/or in the advanced compositions thereof. This morphology is susceptible to flow induced orientation during processing which can result in enhanced unidirectional, mechanical properties. This is not possible to any great extent with conventional epoxy resins.

In contrast to other types of mesogenic polymers, which are primarily thermoplastics, the epoxy resins containing rodlike mesogenic moieties provide an advantage in that final chain extension and/or crosslinking occurs during the curing stages of the fabricated part. This permits new systems which process at much lower temperatures.

The rodlike mesogenic structures incorporated into the chain provide the improvement in one or more of the properties. The property improvements obtained with epoxy resins of this type can be unidirectionally enhanced by electric or magnetic fields or by shear stresses applied during processing and/or curing.

SUMMARY OF THE INVENTION

One aspect of the present invention pertains to epoxy resins containing one or more rodlike mesogenic moieties represented by the following Formula I

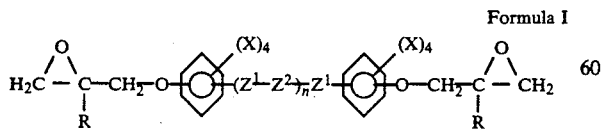

Formula I wherein at least about 80 percent of the -($Z^1$-$Z^2$)$_n$-$Z^1$- linkages and the glycidyl ether groups are in the para position with respect to each other: each R and $R^1$ is independently hydrogen or an aliphatic hydrocarbon group having from 1 to about 4 carbon atoms; each X is independently hydrogen, a hydrocarbyl or hydrocarbyloxy group having suitably from 1 to about 12, more suitably from 1 to about 6, most suitably from 1 to about 4, carbon atoms, a halogen atom (preferably chlorine or bromine), —$NO_2$, or —C≡N; each $Z^1$ is independently —$CR^1$=$CR^1$—, —$CR^1$=$CR^1$—$CR^1$=$CR^1$—, —$CR^1$=N—N=$CR^1$—, —$CR^1$=$CR^1$—CO—O—$CH_2$—, —$CR^1$=$CR^1$—CO—O—$CH_2$—$CH_2$—, —$CH_2$—O—CO—$CR^1$=$CR^1$—, —$CH_2$—O—CO—$CR^1$=$CR^1$—, —$CR^1$=$CR^1$—CO—O—, —O—CO—$CR^1$=$CR^1$—, —CO—$NR^1$—, —$NR^1$—CO—, —CO—$NR^1$—$NR^1$—CO—, —C≡C—, —C≡C—C≡C—, —$CR^1$=$CR^1$—O—CO—$CH_2$—, —$CH_2$—CO—O—$CR^1$=$CR^1$—, —$CR^1$=$CR^1$—O—CO—$CH_2$—$CH_2$—, —$CH_2$—$CH_2$—CO—$CR^1$=$CR^1$—, —$CH_2$—$CH_2$—CO—O—, —O—CO—$CH_2$—$CH_2$—, —CO—O—$CR^1$=$CR^1$—, —$CR^1$=$CR^1$—O—CO—,

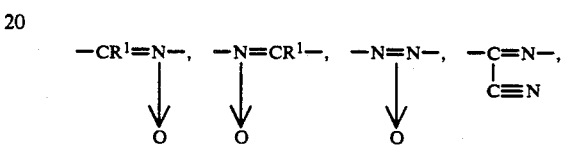

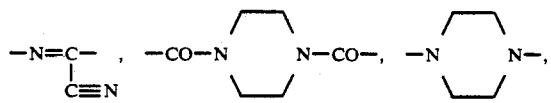

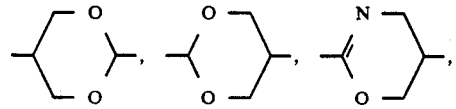

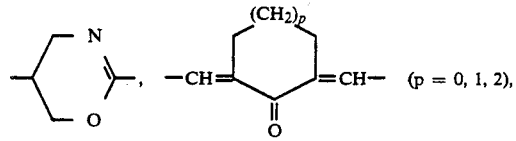

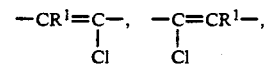

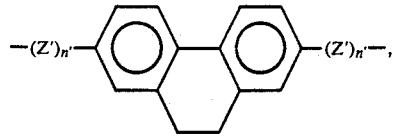

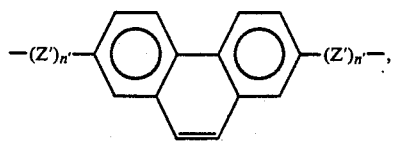

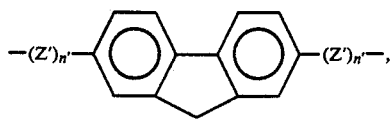

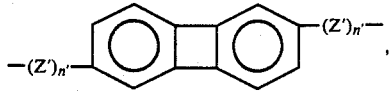

-continued

[chemical structures: various substituted cyclohexane, cyclohexene, quinoline, furan, thiophene, benzimidazole, benzoxazole, benzothiazole, and benzothiazole-oxazole rings, each with $-(Z')_{n'}-$ substituents]

$Z^2$ is a group represented by a cyclic or bicyclic ring system containing from 5 to about 12 carbon atoms and may be cycloaliphatic, polycycloaliphatic, aromatic or a combination thereof; n is 0 to 2; each $Z'$ is independently a $-CO-$, $-O-CO-$, $-CO-O-$, $-CO-NR^1-$, or $-NR^1-CO-$ group and each $n'$ independently has a value of zero or one;

with the proviso that:

(a) both of the $R^1$ groups in the $-CR^1=CR^1-$ group cannot simultaneously be a hydrogen atom;

(b) each $Z^1$ can also independently be

[structures showing $-CR^1=C(-C\equiv N)-$ and $-C(-C\equiv N)=CR^1-$]

$-CR^1=N-$, $-N=CR^1-$, $-CO-CR^1=CR^1-$ and $-CR^1=CR^1-CO-$ when $Z^2$ is not a benzene ring and $n \neq 0$;

(c) $R^1$ in the $-CR^1=N-$ and $-N=CR^1-$ groups is other than hydrogen;

(d) when n=1, either one of $Z^1$ can also be selected from the group consisting of $-CH=CH-$, $-N=N-$, $-CO-S-$, $-S-CO-$, $-CH=N-$, $-N=CH-$, $-O-CO-$, $-CO-O-$ and a direct single bond provided that the other $Z^1$ group is not selected from this same group or is not selected from a group selected from the group consisting of

[structures: piperazine ring $-N\langle\rangle N-$, and two dioxane-like rings with two O atoms]

[structure: $-(Z')_{n'}-$cyclohexane(CHR$^1$)$-(Z')_{n'}-$]

[structure: $-(Z')_{n'}-$cyclohexane$-(Z')_{n'}-$] and when (i) each n' is zero, or (ii) when one n'=zero and one n'=1 with $Z'$ being $-O-CO-$ or $-CO-O-$ and $R^1$ is a group having only one carbon atom;

(e) when n=2, one or two $Z^1$ groups can also independently be selected from the group consisting of $-CH=CH-$, $-N=N-$, $-CO-S-$, $-S-CO-$, $-CH=N-$, $-N=CH-$, $-O-CO-$, $-CO-O-$, and a direct single bond, provided that the remaining $Z^1$ groups are not selected from this group;

(f) when one $Z^1$ is

[structure: $-(Z')_{n'}-$cyclohexane(CHR$^1$)$-(Z')_{n'}-$] or

[structure: $-(Z')_{n'}-$cyclohexane$-(Z')_{n'}-$]

wherein (i) when each n'=1 with each $Z'$ being $-O-CO-$ or $-CO-O-$, or (ii) when one n'=1 with $Z'$ being $-O-CO-$ or $-CO-O-$ and the other n'=zero resulting in the other $Z'$ being a direct bond and $R^1$ is a group having only one carbon atom, then n must have a value of 1 or 2 and $R^1$ is a group having only one carbon atom.

Another aspect of the present invention pertains to epoxy resins containing one or more rodlike mesogenic moieties represented by the following Formula II

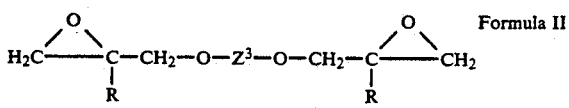

wherein $Z^3$ is

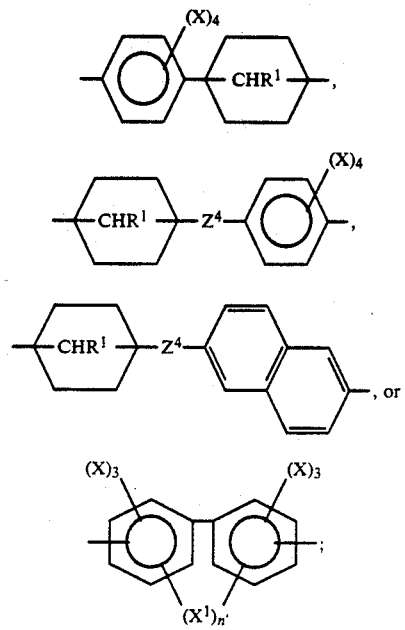

and $Z^4$ is —CO—O—, —O—CO—, —NR$^1$—CO— or —CO—NR$^1$—; X$^1$ is a divalent hydrocarbyl group having from 1 to about 10, preferably from 1 to about 4, carbon atoms which can contain one or more heteroatoms selected from N, O, S and the like and may be saturated or unsaturated; each R and R$^1$ is independently hydrogen or an aliphatic hydrocarbon group having from 1 to about 4 carbon atoms; each X is independently hydrogen, a hydrocarbyl or hydrocarbyloxy group having suitably from 1 to about 12, more suitably from 1 to about 6, most suitably from 1 to about 4, carbon atoms, a halogen atom (preferably chlorine or bromine), —NO$_2$, or —C≡N; and n' is zero or one; and with the proviso that $Z^4$ is not —CO—O— or —O—CO— when R$^1$ is a group having only one carbon atom.

Another aspect of the present invention pertains to monoepoxide compounds containing one or more rodlike mesogenic moieties represented by the following Formula III

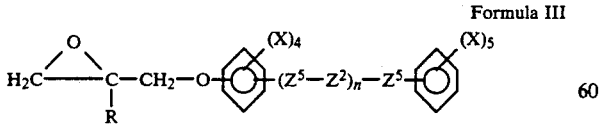

wherein at least about 80 percent of the -(Z$^5$-Z$^2$)$_n$-Z$^5$- linkages and the glycidyl ether groups are in the para position with respect to each other; each R and R$^1$ is independently hydrogen or an aliphatic hydrocarbon group having from 1 to about 4 carbon atoms; each X is independently hydrogen, a hydrocarbyl or hydrocarbyloxy group having suitably from 1 to about 12, more suitably from 1 to about 6, most suitably from 1 to about 4, carbon atoms, a halogen atom (preferably chlorine or bromine), —NO$_2$, or —C≡N; each $Z^5$ is independently —CR$^1$=CR$^1$—, —CR$^1$=CR$^1$—CR$^1$=CR$^1$—, —CR$^1$=N—N=CR$^1$—, —CR$^1$=CR$^1$—CO—O—CH$_2$—, —CR$^1$=CR$^1$—CO—O—CH$_2$—CH$_2$—, —CH$_2$—O—CO—CR$^1$=CR$^1$—, —CH$_2$—CH$_2$—O—CO—CR$^1$=CR$^1$—, —CR$^1$=CR$^1$—CO—O—, —O—CO—CR$^1$=CR$^1$—, —N=N—, —CO—NR$^1$—, —NR$^1$—CO—, —CO—NR$^1$—NR$^1$—CO—, —C≡C—, —C≡C—C≡C—, —CO—S—, —S—CO—, —CR$^1$=N—, —N=CR$^1$—, —CO—O—, —O—CO—, —CR$^1$=CR$^1$—O—CO—CH$_2$—, —CH$_2$—CO—O—CR$^1$=CR$^1$—, —CR$^1$=CR$^1$—O—CO—CH$_2$—CH$_2$—, —CH$_2$—CH$_2$—CO—CR$^1$=CR$^1$—, —CH$_2$—CH$_2$—CO—O—, —O—CO—CH$_2$—CH$_2$—, —CO—O—CR$^1$=CR$^1$—, —CR$^1$=CR$^1$—O—CO—, a direct single bond when n≧1,

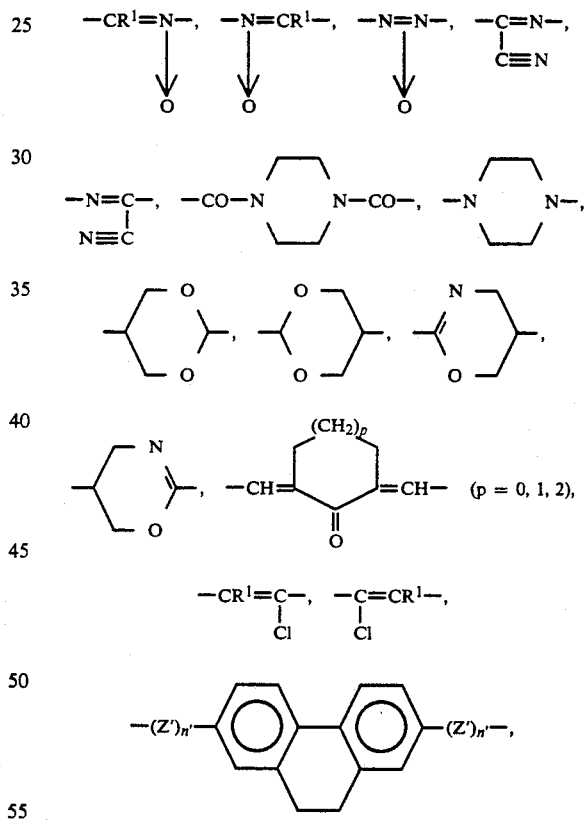

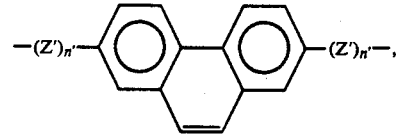

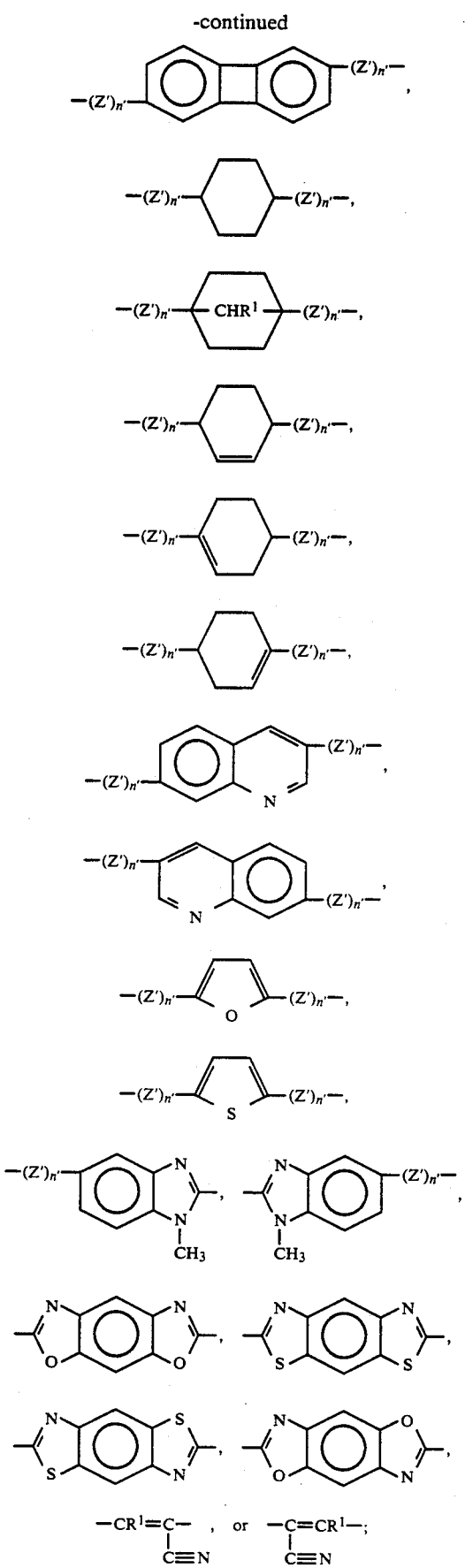

$Z^2$ is a group represented by a cyclic or bicyclic ring system containing from 5 to about 12 carbon atoms and may be cycloaliphatic, polycycloaliphatic, aromatic or a combination thereof; n is zero or two; each $Z'$ is independently a —CO—, —O—CO—, —CO—O—, —CO—NR$^1$—, or —NR$^1$—CO— group; and each n' is independently zero or one.

Another aspect of the present invention pertains to monoepoxide compounds containing one or more rod-like mesogenic moieties represented by the following Formula IV

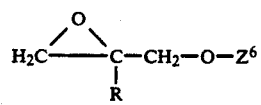

Formula IV wherein $Z^6$ is

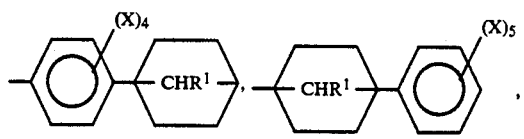

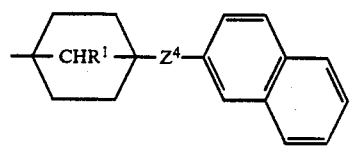

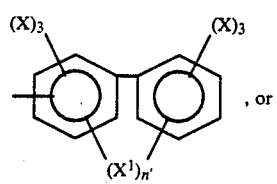, or

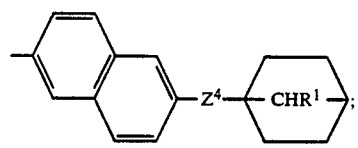

and $Z^4$ is —CO—O, —O—CO—, or —CO—NR$^1$—; each R and R$^1$ is independently hydrogen or an aliphatic hydrocarbon group having from 1 to about 4 carbon atoms; each X is independently hydrogen, a hydrocarbyl or hydrocarbyloxy group having suitably from 1 to about 12, more suitably from 1 to about 6, most suitably from 1 to about 4, carbon atoms, a halogen atom (preferably chlorine or bromine), —NO$_2$, or —C≡N; X$^1$ is a divalent hydrocarbyl group having from 1 to about 10, preferably from 1 to about 4, carbon atoms which can contain one or more heteroatoms selected from N, O, or S and may be saturated or unsaturated: and n' is zero or one.

Another aspect of the present invention pertains to advanced epoxy resin compositions prepared by reacting (A) one or more of the epoxy resins containing one or more rodlike mesogenic moieties, said epoxy resin being those represented by either the following Formula I

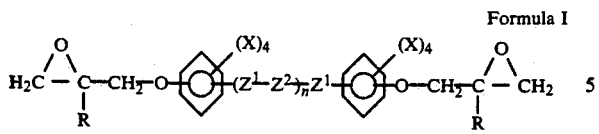
Formula I wherein at least about 80 percent of the $-(Z^1-Z^2)_n-Z^1-$ linkages and the glycidyl ether groups are in the para position with respect to each other; each R and $R^1$ is independently hydrogen or an aliphatic hydrocarbon group having from 1 to about 4 carbon atoms; each X is independently hydrogen, a hydrocarbyl or hydrocarbyloxy group having suitably from 1 to about 12, more suitably from 1 to about 6, most suitably from 1 to about 4, carbon atoms, a halogen atom (preferably chlorine or bromine), $-NO_2$, or $-C\equiv N$; each $Z^1$ is independently $-CR^1=CR^1-$, $-CR^1=CR^1-CR^1=CR^1-$, $-CR^1=N-N=CR^1-$, $-CR^1=CR^1-CO-O-CH_2-$, $-CR^1=CR^1-CO-O-CH_2-CH_2-$, $-CH_2-O-CO-CR^1=CR^1-$, $-CH_2-CH_2-O-CO-CR^1=CR^1-$, $-CR^1=CR^1-CO-O-$, $-O-CO-CR^1=CR^1-$, $-CO-NR^1-$, $-NR^1-CO-$, $-CO-NR^1-NR^1-CO-$, $-C\equiv C-$, $-C\equiv C-C\equiv C-$, $-N=N-$, $-CO-S-$, $-S-CO-$, $-CR^1=CR^1-O-CO-CH_2-$, $-CH_2-CO-O-CR^1=CR^1-$, $-CR^1=CR^1-O-CO-CH_2-CH_2-$, $-CH_2-CH_2-CO-O-CR^1=CR^1-$, $-CH_2-CH_2-CO-O-$, $-O-CO-CH_2-CH_2-$, $-CO-O-CR^1=CR^1-$, $-CR^1=CR^1-O-CO-$, a direct single bond when $n \geq 1$,

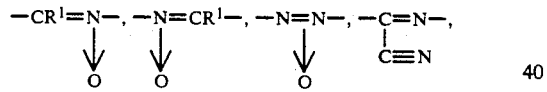

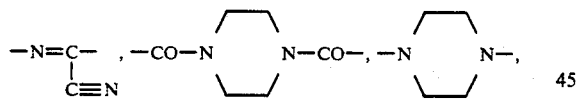

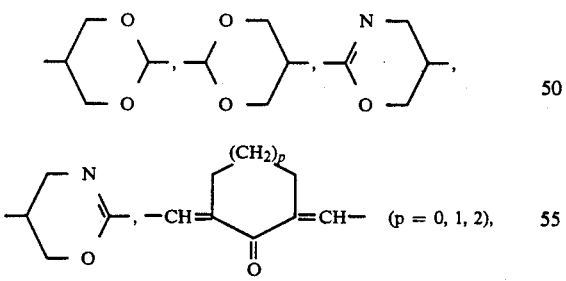

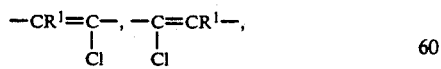

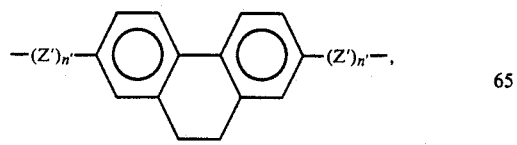

-continued

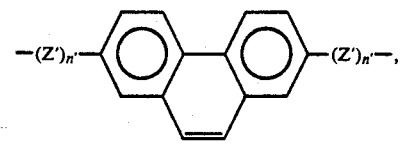

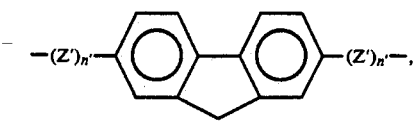

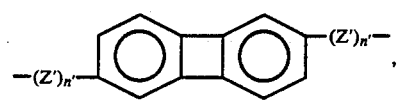

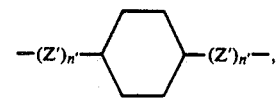

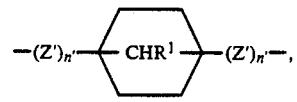

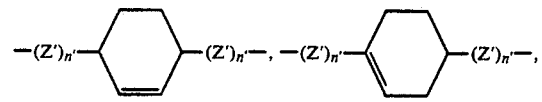

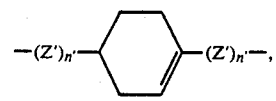

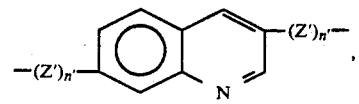

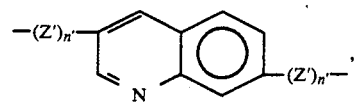

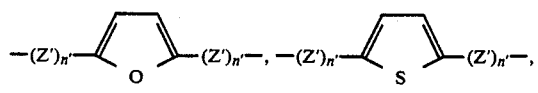

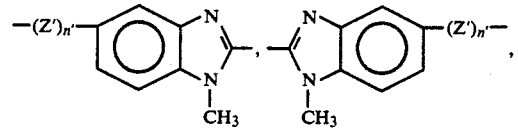

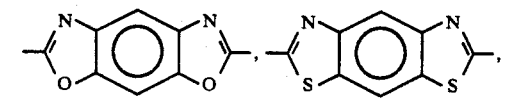

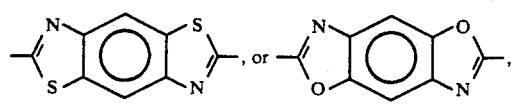

$Z^2$ is a group represented by a cyclic or bicyclic ring system containing from 5 to about 12 carbon atoms and may be cycloaliphatic, polycycloaliphatic, aromatic or a combination thereof; n is 0 to 2; each Z' is independently a —CO—, —O—CO—, —CO—O—, —CO—NR$^1$—, or —NR$^1$—CO— group and each n' independently has a value of zero or one; with the proviso that each $Z^1$ can also independently be

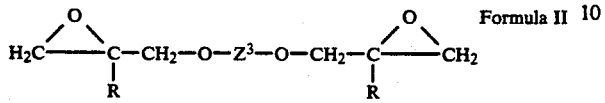
Formula II

—CR$^1$=N—, —N=CR$^1$—, —CO—CR$^1$=CR$^1$—, —CR$^1$=CR$^1$—CO—, —CO—O—, and —O—CO— when $Z^2$ is not a benzene ring and when n≠0; or the following Formula II

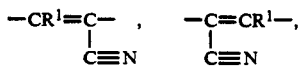

wherein $Z^3$ is

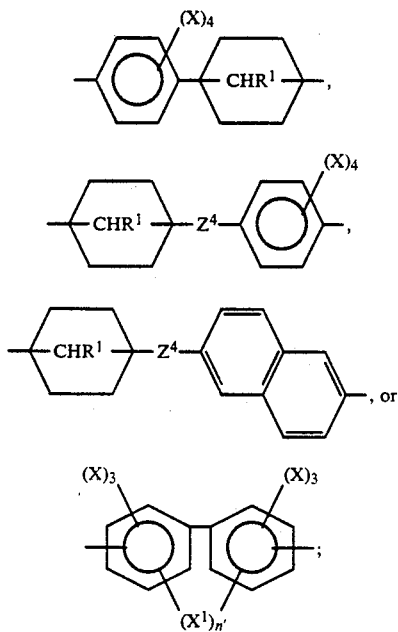

and $Z^4$ is —CO—O—, —O—CO—, —NR$^1$—CO— or —CO—NR$^1$—; $X^1$ is a divalent hydrocarbyl group having from 1 to about 10, preferably from 1 to about 4, carbon atoms which can contain one or more heteroatoms selected from N, O, S and the like and may be saturated or unsaturated; each R and R$^1$ is independently hydrogen or an aliphatic hydrocarbon group having from 1 to about 4 carbon atoms; each X is independently hydrogen, a hydrocarbyl or hydrocarbyloxy group having suitably from 1 to about 12, more suitably from 1 to about 6, most suitably from 1 to about 4, carbon atoms, a halogen atom (preferably chlorine or bromine), —NO$_2$, or —C≡N; and n' is zero or one; with (B) at least one compound having an average of more than one active hydrogen atom per molecule; and wherein components (A) and (B) are employed in quantities which provide a ratio of active hydrogen atoms per epoxide group of from about 0.01:1 to about 0.95:1, more suitably from about 0.05:1 to about 0.8:1, most suitably from about 0.1:1 to about 0.5:1.

Another aspect of the present invention pertains to phenoxy resin compositions prepared by the advancement reaction of (A) one or more of the epoxy resins containing one or more rodlike mesogenic moieties, said epoxy resins being those represented by either the following Formula I

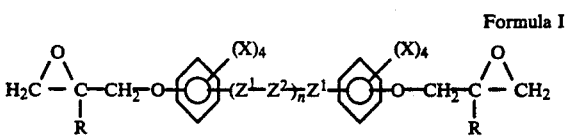
Formula I wherein at least about 80 percent of the -($Z^1$-$Z^2$)$_n$-$Z^1$- linkages and the glycidyl ether groups are in the para position with respect to each other; each R and R$^1$ is independently hydrogen or an aliphatic hydrocarbon group having from 1 to about 4 carbon atoms; each X is independently hydrogen, a hydrocarbyl or hydrocarbyloxy group having suitably from 1 to about 12, more suitably from 1 to about 6, most suitably from 1 to about 4, carbon atoms, a halogen atom (preferably chlorine or bromine), —NO$_2$, or —C≡N; each $Z^1$ is independently —CR$^1$=CR$^1$—, —CR$^1$=CR$^1$—CR$^1$=CR$^1$—, —CR$^1$=N—N=CR$^1$—, —CR$^1$=CR$^1$—CO—O—CH$_2$—, —CR$^1$=CR$^1$—CO—O—CH$_2$—CH$_2$—, —CH$_2$—O—CO—CR$^1$=CR$^1$—, —CH$_2$—CH$_2$—O—CO—CR$^1$=CR$^1$—, —CR$^1$=CR$^1$—CO—O—, —O—CO—CR$^1$=CR$^1$—, —CO-NR$^1$—, —NR$^1$—CO—, —CO—NR$^1$—NR$^1$—CO—, —C≡C—, —C≡C—C≡C—, —N=N—, —CO—S—, —S—CO—, —CR$^1$=N—, —N=CR$^1$—, —CO—CR$^1$=CR$^1$—, —CR$^1$=CR$^1$—CO—, —CR$^1$=CR$^1$—O—CO—CH$_2$—, —CH$_2$—CO—O—CR$^1$=CR$^1$—, —CR$^1$=CR$^1$—O—CO—CH$_2$—CH$_2$—, —CH$_2$—CH$_2$—CO—O—CR$^1$=CR$^1$—, —CH$_2$—CH$_2$—CO—O—, —O—CO—CH$_2$—CH$_2$—, —CO—O—CR$^1$=CR$^1$—, —CR$^1$=CR$^1$—O—CO—, —O—CO—, —CO—O—,

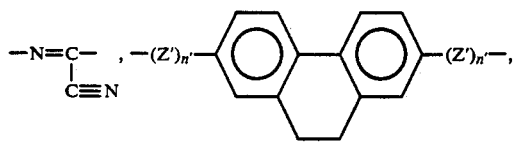

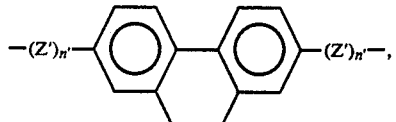

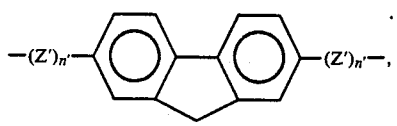

-continued

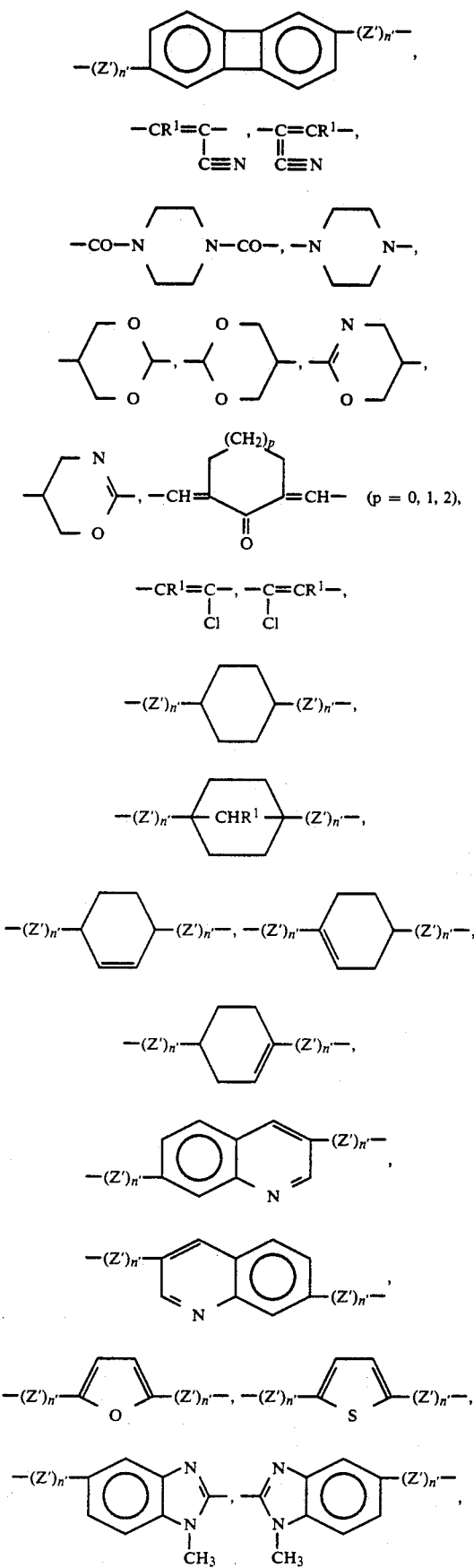

-continued

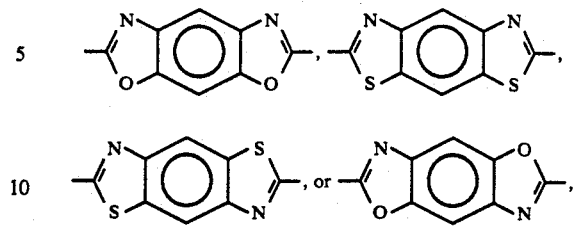

$Z^2$ is a group represented by a cyclic or bicyclic ring system containing from 5 to about 12 carbon atoms and may be cycloaliphatic, polycycloaliphatic, aromatic or a combination thereof; n is 0 to 2; each $Z'$ is independently a —CO—, —O—CO—, —CO—O—, —CO—NR$^1$—, or —NR$^1$—CO— group and each n' independently has a value of zero or one; or the following Formula II

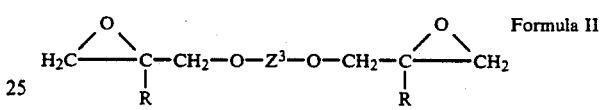

wherein $Z^3$ is

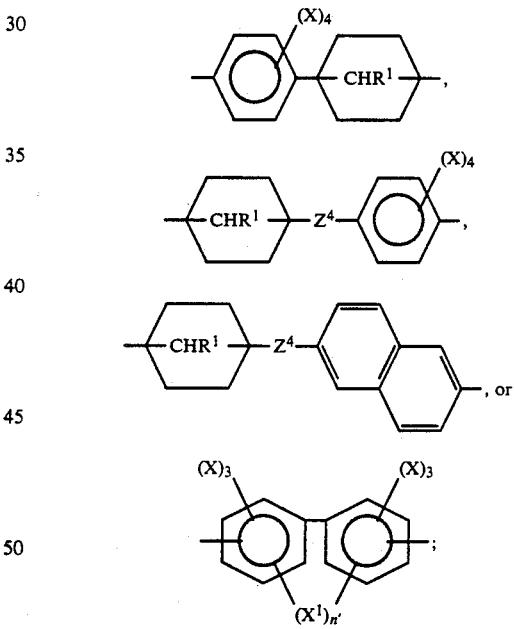

and $Z^4$ is —CO—O—, —O—CO—, —NR$^1$—CO— or —CO—NR$^1$—; $X^1$ is a divalent hydrocarbyl group having from 1 to about 10, preferably from 1 to about 4, carbon atoms which can contain one or more heteroatoms selected from N, O, S and the like and may be saturated or unsaturated: each R and R$^1$ is independently hydrogen or an aliphatic hydrocarbon group having from 1 to about 4 carbon atoms; each X is independently hydrogen, a hydrocarbyl or hydrocarbyloxy group having suitably from 1 to about 12, more suitably from 1 to about 6, most suitably from 1 to about 4, carbon atoms, a halogen atom (preferably chlorine or bromine), —NO$_2$, or —C≡N; and n' is zero or one; with (B) at least one compound having an average of more than one active hydrogen atom per molecule; and wherein components (A) and (B) are employed in quantities which provide a ratio of active hydrogen atoms per epoxide group of from about 0.96:1 to about 1.05:1.

Another aspect of the present invention pertains to blends of (A) one or more of the epoxy resins or monoepoxide compounds containing one or more rodlike mesogenic moieties which epoxy resins or monoepoxide compounds are represented by the aforementioned Formulas I, II, III or IV and (B) one or more polyepoxides represented by the following Formulas V, VI, VII, VIII, IX, X or XI;

Formula V
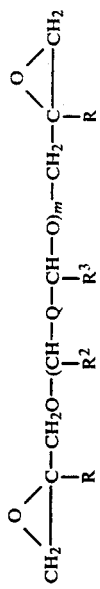
Formula VI
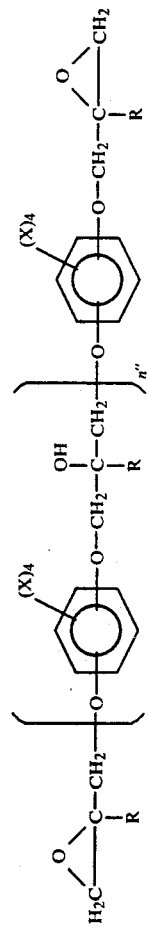
Formula VII
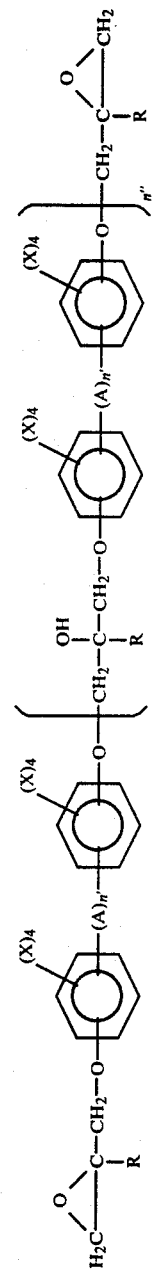
Formula VIII
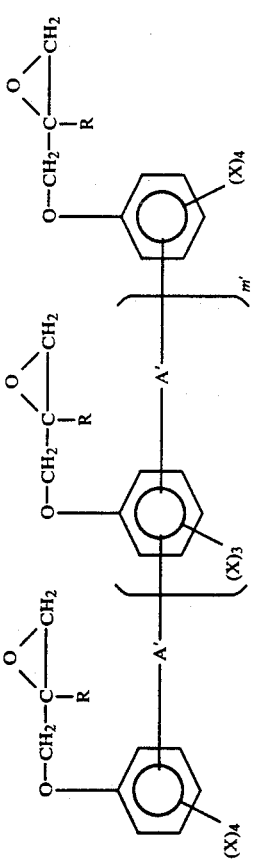
Formula IX
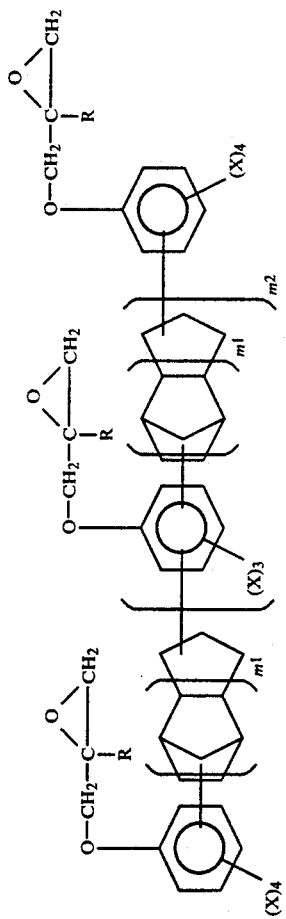

-continued
Formula X
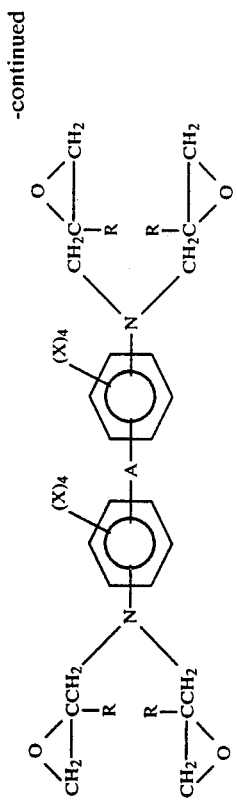
Formula XI
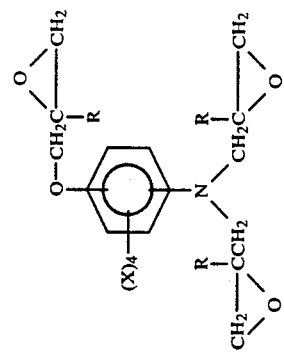

wherein each A is independently a divalent hydrocarbyl group having from 1 to about 12, preferably from about 1 to about 6, more preferably from 1 to about 3, carbon atoms, —O—, —S—, —S—S—, —SO—, —SO$_2$—, or —CO—; each A' is independently a divalent hydrocarbon group having from 1 to about 6, preferably from 1 to about 3, carbon atoms; Q is a single bond, —CH$_2$—S—CH$_2$—, —(CH$_2$)$_{n1}$—, or

each R is independently hydrogen or an alkyl group having from 1 to about 4 carbon atoms; each R$^2$ and R$^3$ is independently hydrogen, a hydrocarbyl or halohydrocarbyl group having from 1 to about 6, preferably from 1 to about 3, more preferably from 1 to about 2, carbon atoms; each X is independently hydrogen, a hydrocarbyl or hydrocarbyloxy group having from 1 to about 12, preferably from about 1 to about 6, most preferably from 1 to about 4, carbon atoms, a halogen atom, —NO$_2$ or —C≡N; m has a value from about 1 to about 10, preferably from about 1 to about 4, more preferably from about 1 to about 2; ml has an average value from about 0.01 to about 12, preferably from about 1 to about 6, more preferably from about 1 to about 3; m$^1$ has an average value from about 1 to about 12, preferably from about 1 to about 6, more preferably from about 1 to about 3; m$^2$ has a value from about 1 to about 12, preferably from about 2 to about 6, more preferably from about 2 to about 3; n' has a value of zero or 1; n" has an average value from about zero to about 3, preferably from about zero to about 1.5, more preferably from about zero to about 0.5, and n$^1$ has an average value from about 1 to about 10; and wherein component (A) is present in an amount suitably from about 1 to about 99, more suitably from about 10 to about 80, most suitably from about 10 to about 50, percent by weight based upon the combined weight of components (A) and (B) and component (B) is present in an amount suitably from about 99 to about 1, more suitably from about 90 to about 20, most suitably from about 90 to about 50, percent by weight based upon the combined weight of components (A) and (B).

Another aspect of the present invention pertains to blends of (A) one or more of the advanced epoxy resins containing one or more rodlike mesogenic moieties which advanced epoxy resins are prepared by reacting one or more epoxy resins represented by Formulas I or II and at least one compound having an average of more than one active hydrogen atom per molecule; and (B) one or more polyepoxides represented by Formulas V, VI, VII, VIII, IX, X or XI; and wherein component (A) is present in an amount suitably from about 1 to about 99, more suitably from about 10 to about 80, most suitably from about 10 to about 50, percent by weight based upon the combined weight of components (A) and (B) and component (B) is present in an amount suitably from about 99 to about 1, more suitably from about 90 to about 20, most suitably from about 90 to about 50, percent by weight based upon the combined weight of components (A) and (B).

Another aspect of the present invention pertains to curable compositions comprising at least one epoxy resin containing one or more rodlike mesogenic moieties represented by Formula I and a curing amount of a suitable curing agent therefor.

Another aspect of the present invention pertains to curable compositions comprising at least one epoxy resin containing one or more rodlike mesogenic moieties represented by Formula II and a curing amount of a suitable curing agent therefor.

Another aspect of the present invention pertains to curable compositions comprising (A) at least one epoxy resin containing one or more rodlike mesogenic moieties, said epoxy resin being represented by either the following Formula I Formula I

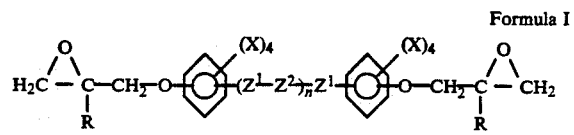

wherein at least about 80 percent of the -(Z$^1$-Z$^2$)$_n$-Z$^1$- linkages and the glycidyl ether groups are in the para position with respect to each other; each R and R$^1$ is independently hydrogen or an aliphatic hydrocarbon group having from 1 to about 4 carbon atoms; each X is independently hydrogen, a hydrocarbyl or hydrocarbyloxy group having suitably from 1 to about 12, more suitably from 1 to about 6, most suitably from 1 to about 4, carbon atoms, a halogen atom (preferably chlorine or bromine), —NO$_2$, or —C≡N; each Z$^1$ is independently —CR$^1$=CR$^1$—, —CR$^1$=CR$^1$—CR$^1$=CR$^1$—, —CR$^1$=N—N=CR$^1$—, —CR$^1$=CR$^1$—CO—O—CH$_2$—, —CR$^1$=CR$^1$—CO—O—CH$_2$—CH$_2$—, —CH$_2$—O—CO—CR$^1$=CR$^1$—, —CH$_2$—CH$_2$—O—CO—CR$^1$=CR$^1$—, —CR$^1$=CR$^1$—CO—O—, —O—CO—CR$^1$=CR$^1$—, —CO—NR$^1$—, —NR$^1$—CO—, —CO—NR$^1$—NR$^1$—CO—, —C≡C—, —C≡C—C≡C—, —N=N—, —CO—S—, —S—CO—, —CR$^1$=N—, —N=CR$^1$—, —CO—CR$^1$=CR$^1$—, —CR$^1$=CR$^1$—CO—, —CR$^1$=CR$^1$—O—CO—CH$_2$—, —CH$_2$—CO—O—CR$^1$=CR$^1$—, —CR$^1$=CR$^1$—O—CO—CH$_2$—CH$_2$—, —CH$_2$—CH$_2$—CO—O—CR$^1$=CR$^1$—, —O—CO—CH$_2$—CH$_2$—, —CO—O—CR$^1$=CR$^1$—, —CR$^1$=CR$^1$—O—CO—, —O—CO—, —CO—O—,

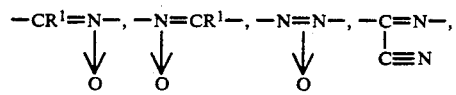

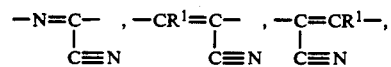

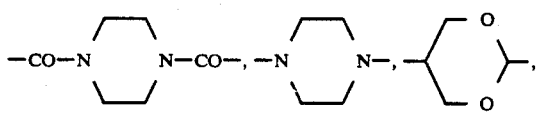

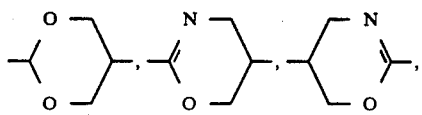

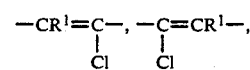

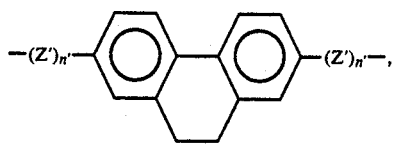

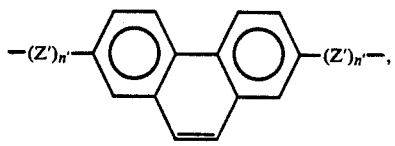

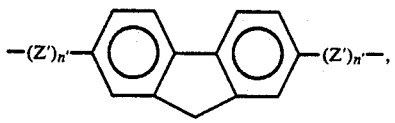

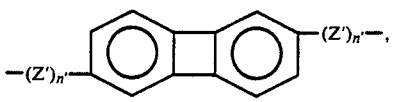

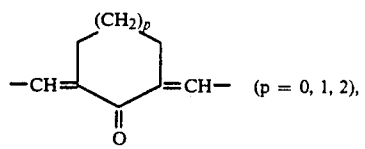

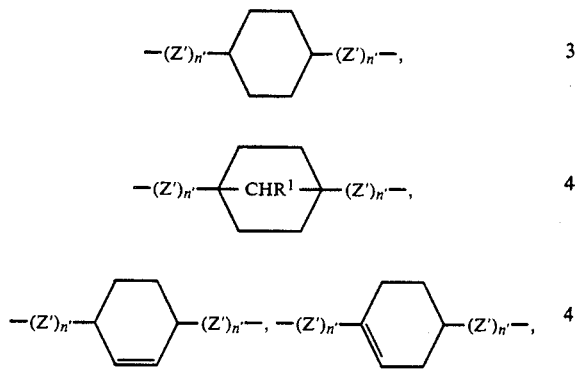

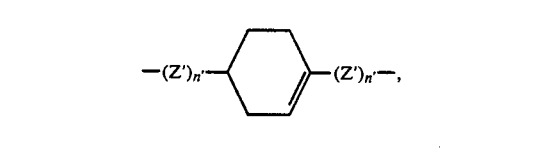

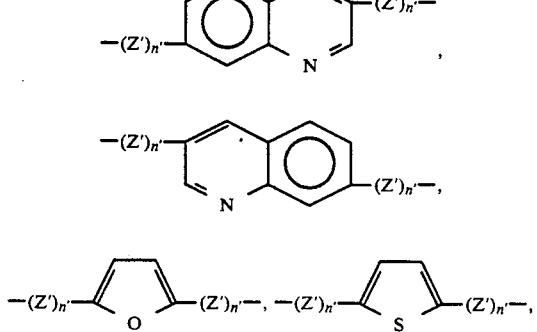

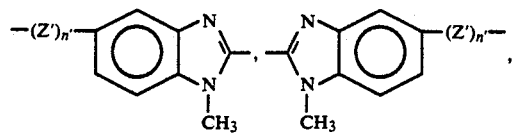

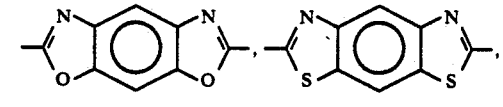

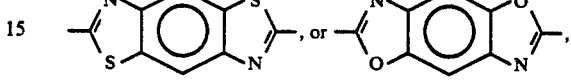

$Z^2$ is a group represented by a cyclic or bicyclic ring system containing from 5 to about 12 carbon atoms and may be cycloaliphatic, polycycloaliphatic, aromatic or a combination thereof; n is 0 to 2; each $Z'$ is independently a —CO—, —O—CO—, —CO—O—, —CO—NR$^1$—, or —NR$^1$—CO— group and each n' independently has a value of zero or one; or the following Formula II

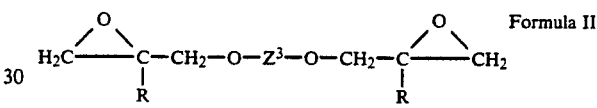

wherein $Z^3$ is

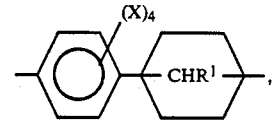

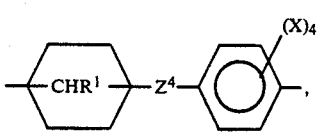

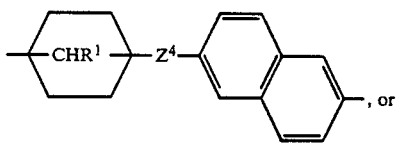

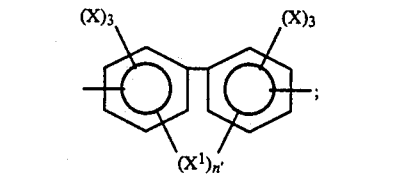

and $Z^4$ is —CO—O—, —O—CO—, —NR$^1$—CO— or —CO—NR$^1$—; $X^1$ is a divalent hydrocarbyl group having from 1 to about 10, preferably from 1 to about 4, carbon atoms which can contain one or more heteroatoms selected from N, O, S and the like and may be saturated or unsaturated; each R and R$^1$ is independently hydrogen or an aliphatic hydrocarbon group having from 1 to about 4 carbon atoms; each X is independently hydrogen, a hydrocarbyl or hydrocarbyloxy group having suitably from 1 to about 12, more suitably from 1 to about 6, most suitably from 1 to about 4, carbon atoms, a halogen atom (preferably chlorine or bromine), —NO$_2$, or —C≡N; and n' is zero or one;

(B) at least one of the aforementioned monoepoxide compounds containing one or more rodlike mesogenic moieties, said monoepoxide compounds being represented by Formulas III or IV, and (C) a curing amount of a suitable curing agent therefor; wherein component (A) is present in an amount suitably from about 1 to about 99, more suitably from about 50 to about 90, most suitably from about 70 to about 90, percent by weight based upon the combined weight of components (A) and (B) and component (B) is present in an amount suitably from about 99 to about 1, more suitably from about 50 to about 10, most suitably from about 30 to about 10, percent by weight based upon the combined weight of components (A) and (B).

Another aspect of the present invention pertains to curable compositions comprising (A) an advanced epoxy resin resulting from reacting (1) at least one of the epoxy resins containing one or more rodlike mesogenic moieties, said epoxy resins being those represented by either the following Formula I

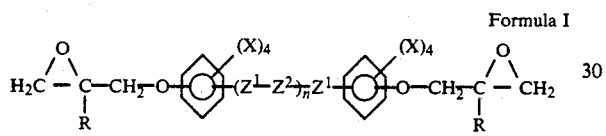

Formula I wherein at least about 8C percent of the -(Z$^1$-Z$^2$)$_n$-Z$^1$- linkages and the glycidyl ether groups are in the para position with respect to each other; each R and R$^1$ is independently hydrogen or an aliphatic hydrocarbon group having from 1 to about 4 carbon atoms; each X is independently hydrogen, a hydrocarbyl or hydrocarbyloxy group having suitably from 1 to about 12, more suitably from 1 to about 6, most suitably from 1 to about 4, carbon atoms, a halogen atom (preferably chlorine or bromine), —NO$_2$, or —C≡N; each Z$^1$ is independently —CR$^1$=CR$^1$—, —CR$^1$=CR$^1$—CR$^1$=CR$^1$—, —CR$^1$=N—N=CR$^1$—, —CR$^1$=CR$^1$—CO—O—CH$_2$—, —CR$^1$=CR$^1$—CO—O—CH$_2$—CH$_2$—, —CH$_2$—O—CO—CR$^1$=CR$^1$—, —CH$_2$—CH$_2$—O—CO—CR$^1$=CR$^1$—, —CR$^1$=CR$^1$—CO—O—, —O—CO—CR$^1$=CR$^1$—, —CO—NR$^1$—, —NR$^1$—CO—, —CO—NR$^1$—NR$^1$—CO—, —C≡C—, —C≡C—C≡C—, —N=N—, —CO—S—, —S—CO—, —CO—O—, —O—CO—, —CR$^1$=CR$^1$—O—CO—CH$_2$—, —CH$_2$—CO—O—CR$^1$=CR$^1$—, —CR$^1$=CR$^1$—O—CO—CH$_2$—CH$_2$—, —CH$_2$—CH$_2$—CO—O—CR$^1$=CR$^1$—, —CH$_2$—CH$_2$—CO—O—, —O—CO—CH$_2$—CH$_2$—, —CO—O—CR$^1$=CR$^1$—, —CR$^1$=CR$^1$—O—CO—, a direct single bond when n≧1,

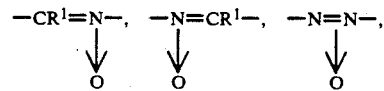

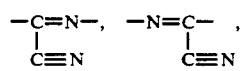

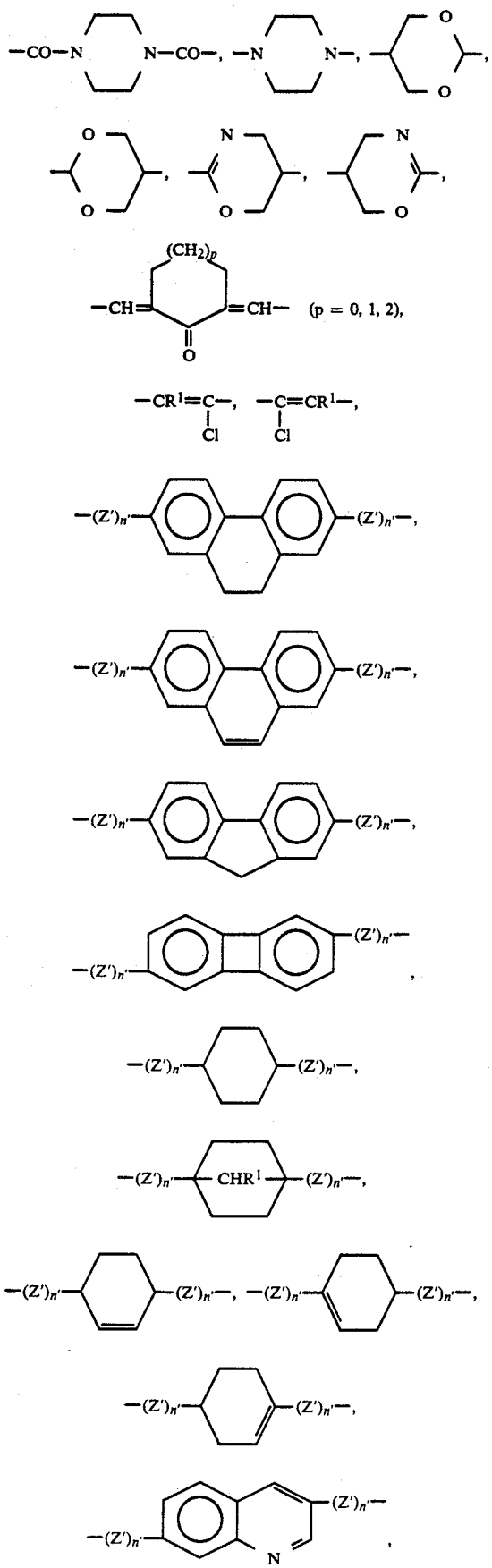

-continued

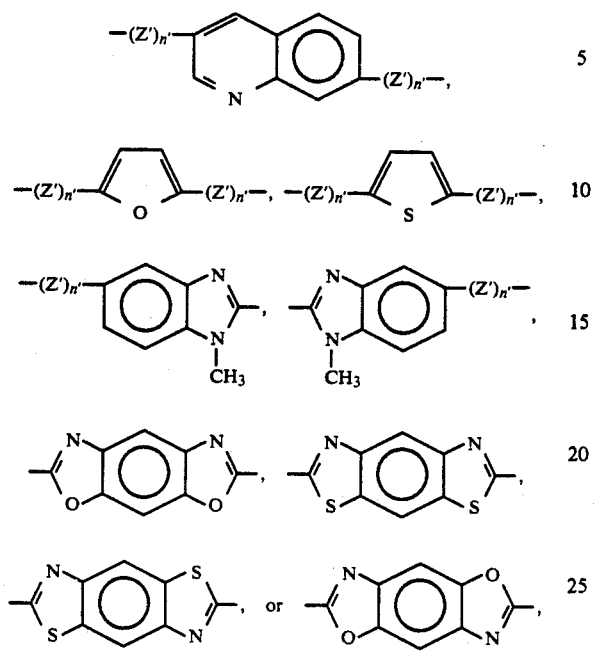

$Z^2$ is a group represented by a cyclic or bicyclic ring system containing from 5 to about 12 carbon atoms and may be cycloaliphatic, polycycloaliphatic, aromatic or a combination thereof; n is 0 to 2; each $Z'$ is independently a —CO—, —O—CO—, —CO—O—, —CO—NR$^1$—, or —NR$^1$—CO— group and each $n'$ independently has a value of zero or one; with the proviso that each $Z^1$ can al3O independently be

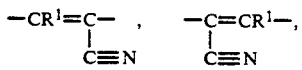

—CR$^1$=N—, —N=CR$^1$—, —CO—CR$^1$=CR$^1$—, —CR$^1$=CR$^1$—CO—, —CO—O—, and —O—CO— when $Z^2$ is not a benzene ring and when $n \neq 0$; or the following Formula II

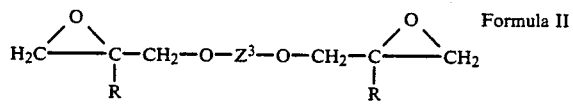

wherein $Z^3$ is

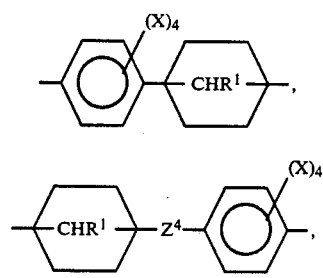

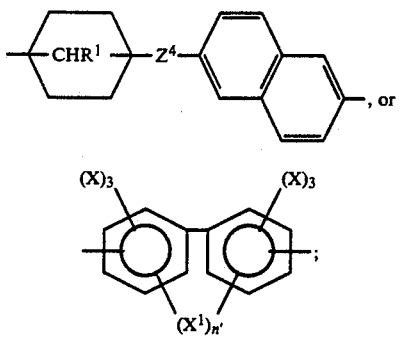

and $Z^4$ is —CO—O—, —O—CO—, —NR$^1$—CO— or —CO—NR$^1$—; $X^1$ is a divalent hydrocarbyl group having from to about 10, preferably from 1 to about 4, carbon atoms which can contain one or more heteroatoms selected from N, O, S and the like and may be saturated or unsaturated; each R and R$^1$ is independently hydrogen or an aliphatic hydrocarbon group having from 1 to about 4 carbon atoms; each X is independently hydrogen, a hydrocarbyl or hydrocarbyloxy group having suitably from 1 to about 12, more suitably from 1 to about 6, most suitably from 1 to about 4, carbon atoms, a halogen atom (preferably chlorine or bromine), —NO$_2$, or —C≡N; and $n'$ is zero or one, or any combination of any two or more of the epoxy resins represented by the aforementioned Formulas I and II; with (2) at least one compound having an average of more than one active hydrogen atom per molecule; wherein components (A1) and (A2) are employed in quantities which provide a ratio of active hydrogen atoms to epoxide groups suitably from about 0.01:1 to about 0.95:1, more suitably from about 0.05:1 to about 0.8:1, most suitably from about 0.1:1 to about 0.5:1; and (B) a curing amount of a suitable curing agent for component (A).

Another aspect of the present invention pertains to curable compositions comprising a blend of (A) at least one of the epoxy resins or monoepoxide compounds containing one or more rodlike mesogenic moieties represented by the following Formulas I or II

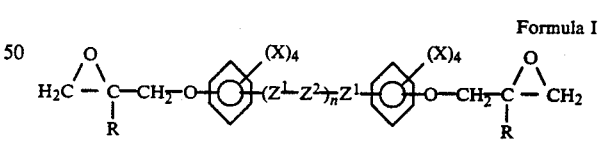

wherein at least about 80 percent of the -(Z$^1$-Z$^2$)$_n$-Z$^1$- linkages and the glycidyl ether groups are in the para position with respect to each other; each R and R$^1$ is independently hydrogen or an aliphatic hydrocarbon group having from 1 to about 4 carbon atoms; each X is independently hydrogen, a hydrocarbyl or hydrocarbyloxy group having suitably from 1 to about 12, more suitably from 1 to about 6, most suitably from 1 to about 4, carbon atoms, a halogen atom (preferably chlorine or bromine), —NO$_2$, or —C≡N; each $Z^1$ is independently —CR$^1$=CR$^1$—, —CR$^1$=CR$^1$—CR$^1$=CR$^1$—, —CR$^1$=N—N=CR$^1$—, —CR$^1$=CR$^1$—CO—O—CH$_2$—, —CR$^1$=CR$^1$—CO—O—CH$_2$—CH$_2$—, —CH$_2$—O—CO—CR$^1$=CR$^1$—, —CH$_2$—CH- $_2$—O—CO—CR$^1$=CR$^1$—, —CR$^1$=CR$^1$—CO—O—, —O—CO—CR$^1$=CR$^1$—, —CO—NR$^1$—, —NR$^1$—CO—, —CO—NR$^1$—NR$^1$—CO—, —C≡C—, —C≡C—C≡C—, —N=N—, —CO—S—, —S—CO—, —CR$^1$=N—, —N=CR$^1$—, —CO—CR$^1$=CR$^1$—, —CR$^1$=CR$^1$—CO—, —CR$^1$=CR$^1$—O—CO—CH$_2$—, —CH$_2$—CO—O—CR$^1$=CR$^1$—, —CR$^1$=CR$^1$—O—CO—CH$_2$—CH$_2$—, —CH$_2$—CH$_2$—CO—O—CR$^1$=CR$^1$—, —CH$_2$—CH$_2$—CO—O—, —O—CO—CH$_2$—CH$_2$—, —CO—O—CR$^1$=CR$^1$—, —CR$^1$=CR$^1$—O—CO—,

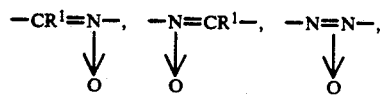

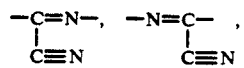

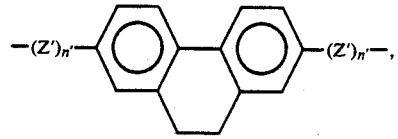

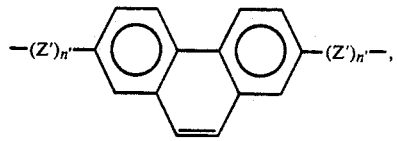

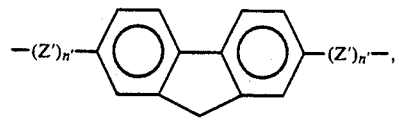

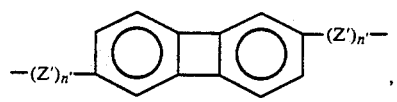

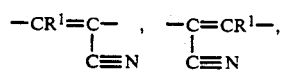

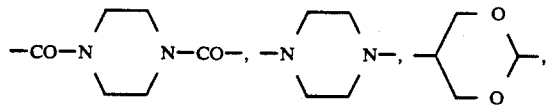

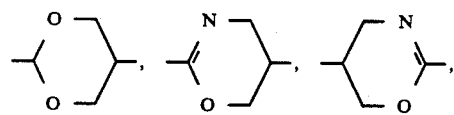

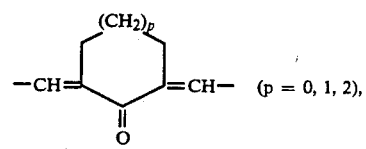

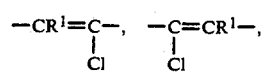

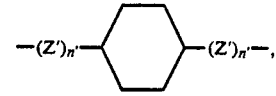

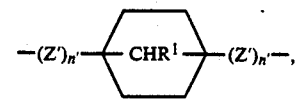

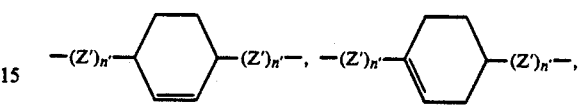

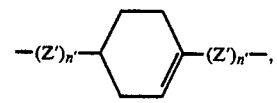

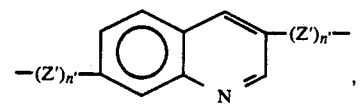

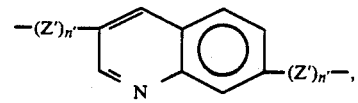

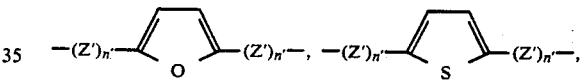

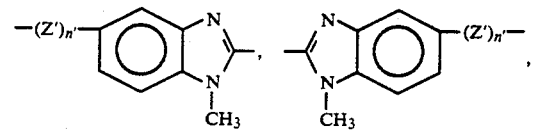

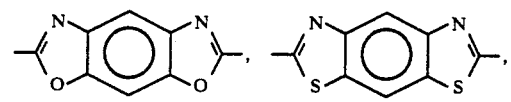

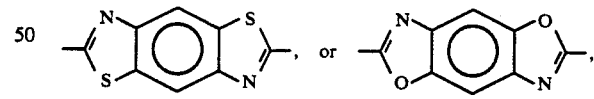

$Z^2$ is a group represented by a cyclic or bicyclic ring system containing from 5 to about 12 carbon atoms and may be cycloaliphatic, polycycloaliphatic, aromatic or a combination thereof; n is 0 to 2; each Z' is independently a —CO—, —O—CO—, —CO—O—, —CO—NR$^1$—, or —NR$^1$—CO— group and each n' independently has a value of zero or one;

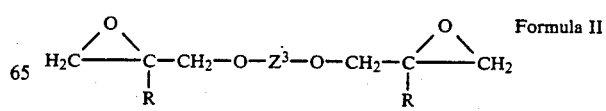

Formula II wherein $Z^3$ is

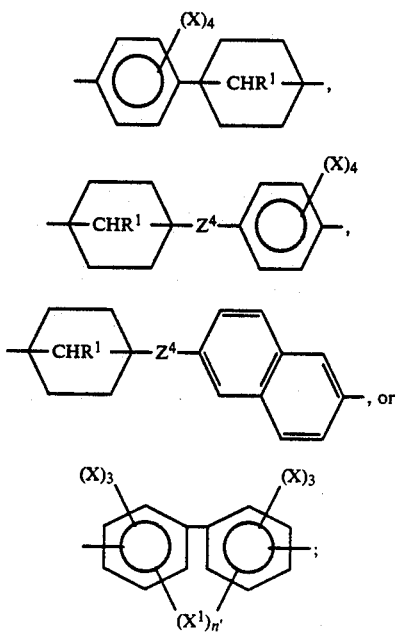

and $Z^4$ is —CO—O—, —O—CO—, —NR$^1$—CO— or —CO—NR$^1$—; $X^1$ is a divalent hydrocarbyl group having from 1 to about 10, preferably from 1 to about 4, carbon atoms which can contain one or more heteroatoms selected from N, O, S and the like and may be saturated or unsaturated; each R and $R^1$ is independently hydrogen or an aliphatic hydrocarbon group having from 1 to about 4 carbon atoms; each X is independently hydrogen, a hydrocarbyl or hydrocarbyloxy group having suitably from 1 to about 12, more suitably from 1 to about 6, most suitably from 1 to about 4, carbon atoms, a halogen atom (preferably chlorine or bromine), —NO$_2$, or —C≡N; and n' is zero or one; or by the aforementioned Formulas III or IV;

(B) at least one of the polyepoxide resins represented by Formulas V, VI, VII, VIII, IX, X or XI; and (C) a curing amount of a suitable curing agent therefor; wherein component (A) is present in an amount suitably from about 1 to about 99, more suitably from about 10 to about 80, most suitably from about 10 to about 50, percent by weight based upon the combined weight of components (A) and (B) and component (B) is present in an amount suitably from about 99 to about 1, more suitably from about 90 to about 20, most suitably from about 90 to about 50, percent by weight based upon the combined weight of components (A) and (B).

Another aspect of the present invention pertains to curable compositions comprising a blend of (A) at least one of the advanced epoxy resins containing one or more rodlike mesogenic moieties prepared by reacting (1) one or more epoxy resins represented by the following Formulas I or II Formula I

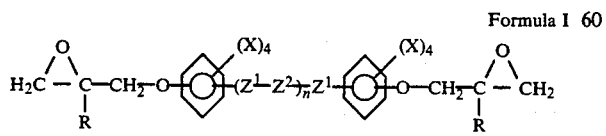

wherein at least about 80 percent of the -(Z$^1$-Z$^2$)$_n$-Z$^1$- linkages and the glycidyl ether groups are in the para position with respect to each other; each R and $R^1$ is independently hydrogen or an aliphatic hydrocarbon group having from 1 to about 4 carbon atoms; each X is independently hydrogen, a hydrocarbyl or hydrocarbyloxy group having suitably from 1 to about 12, more suitably from 1 to about 6, most suitably from 1 to about 4, carbon atoms, a halogen atom (preferably chlorine or bromine), —NO$_2$, or —C≡N; each $Z^1$ is independently —CR$^1$=CR$^1$—, —CR$^1$=CR$^1$—CR$^1$=CR$^1$—, —CR$^1$=N—N=CR$^1$—, —CR$^1$=CR$^1$—CO—O—CH$_2$—, —CR$^1$=CR$^1$—CO—O—CH$_2$—CH$_2$—, —CH$_2$—O—CO—CR$^1$=CR$^1$—, —CH$_2$—CH$_2$—O—CO—CR$^1$=CR$^1$—, —CR$^1$=CR$^1$—CO—O—, —O—CO—CR$^1$=CR$^1$—, —CO—NR$^1$—, —NR$^1$—CO—, —CO—NR$^1$—NR$^1$—CO—, —C≡C—, —C≡C—C≡C—, —N=N—, —CO—S—, —S—CO—, —CR$^1$=N—, —N=CR$^1$—, —CO—CR$^1$=CR$^1$—, —CR$^1$=CR$^1$—CO—, —CR$^1$=CR$^1$—O—CO—CH$_2$—, —CH$_2$—CO—O—CR$^1$=CR$^1$—, —CR$^1$=CR$^1$—O—CO—CH$_2$—CH$_2$—, —CH$_2$—CH$_2$—CO—O—CR$^1$=CR$^1$—, —CH$_2$—CH$_2$—CO—O—, —O—CO—CH$_2$—CH$_2$—, —CO—O—CR$^1$=CR$^1$—, —CR$^1$=CR$^1$—O—CO—,

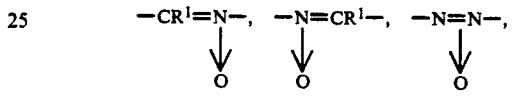

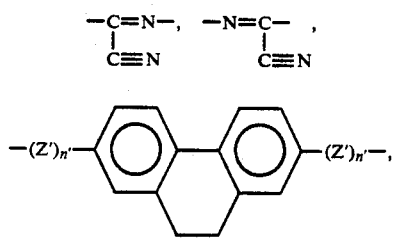

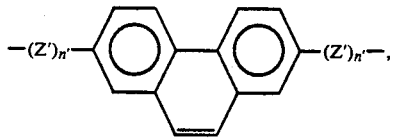

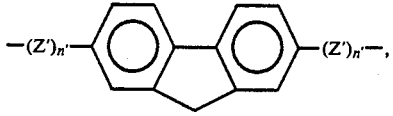

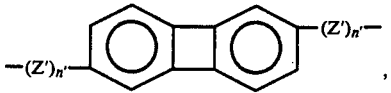

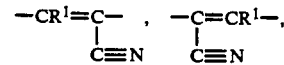

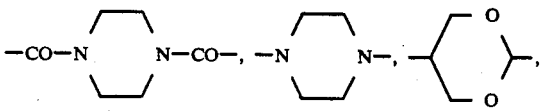

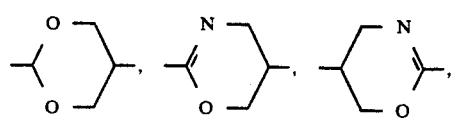

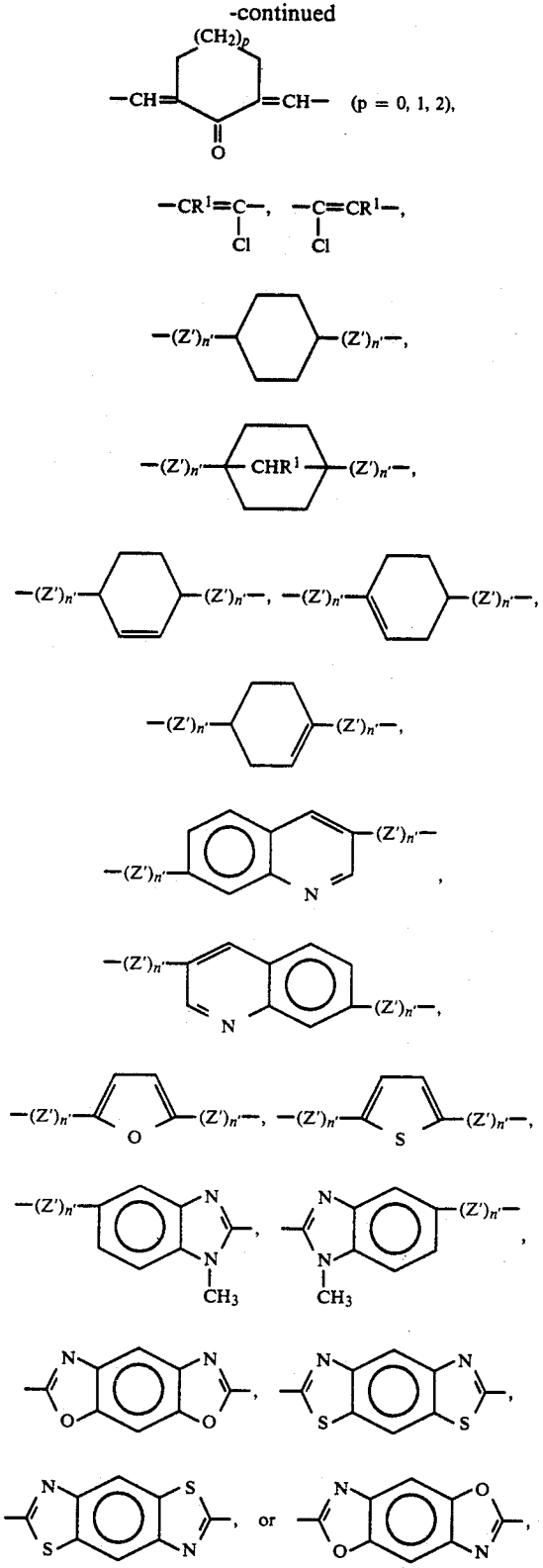

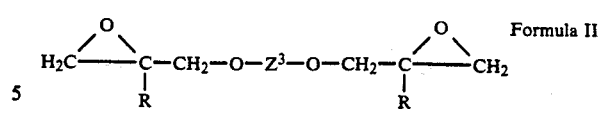

Formula II wherein $Z^3$ is

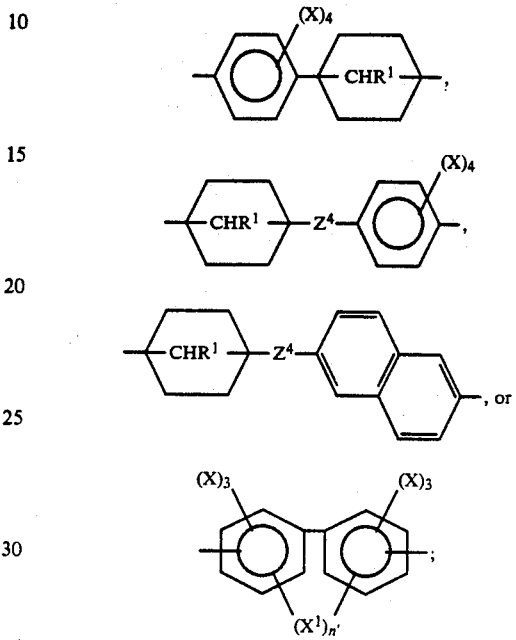

atoms and may be cycloaliphatic, polycycloaliphatic, aromatic or a combination thereof; n is 0 to 2; each Z' is independently a —CO—, —O—CO—, —CO—O—, —CO—NR$^1$—, or —NR$^1$—CO— group and each n' independently has a value of zero or one;

and $Z^4$ is —CO—O—, —O—CO—, —NR$^1$—CO— or —CO—NR$^1$—; $X^1$ is a divalent hydrocarbyl group having from 1 to about 10, preferably from 1 to about 4, carbon atoms which can contain one or more heteroatoms selected from N, O, S and the like and may be saturated or unsaturated; each R and R$^1$ is independently hydrogen or an aliphatic hydrocarbon group having from 1 to about 4 carbon atoms; each X is independently hydrogen, a hydrocarbyl or hydrocarbyloxy group having suitably from 1 to about 12, more suitably from 1 to about 6, most suitably from 1 to about 4, carbon atoms, a halogen atom (preferably chlorine or bromine), —NO$_2$, or —C≡N; and n' is zero or one; and (2) at least one compound having an average of more than one active hydrogen atom per molecule; wherein components (1) and (2) are employed in quantities which provide a ratio of active hydrogen atoms per epoxide group suitably from about 0.01:1 to about 0.95:1, more suitably from about 0.05:1 to about 0.8:1, most suitably from 0.1:1 to about 0.5:1;

(B) at least one of the polyepoxide resins represented by Formulas V, VI, VII, VIII, IX, X or XI; and (C) a curing amount of a suitable curing agent therefor; wherein component (A) is present in an amount suitably from about 1 to about 99, more suitably from about 10 to about 80, most suitably from about 10 to about 50, percent by weight based upon the combined weight of components (A) and (B) and component (B) is present in an amount suitably from about 99 to about 1, more suitably from about 90 to about 20, most suitably from about 90 to about 50, percent by weight based upon the combined weight of components (A) and (B).

A further aspect of the present invention pertains to products resulting from curing the aforementioned curable compositions.

A further aspect of the present invention pertains to products resulting from the application of an electric field, magnetic field, drawing and/or shear flow before and/or during curing or processing of the aforementioned compositions.

A further aspect of the present invention pertains to products resulting from curing a curable composition comprising (A) at least one epoxy resin containing one or more rodlike mesogenic moieties, said epoxy resin being represented by the following Formula I

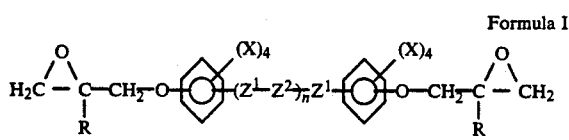

wherein at least about 80 percent of the -(Z$^1$-Z$^2$)$_n$-Z$^1$- linkages and the glycidyl ether groups are in the para position with respect to each other; each R and R$^1$ is independently hydrogen or an aliphatic hydrocarbon group having from 1 to about 4 carbon atoms; each X is independently hydrogen, a hydrocarbyl or hydrocarbyloxy group having suitably from 1 to about 12, more suitably from 1 to about 6, most suitably from 1 to about 4, carbon atoms, a halogen atom (preferably chlorine or bromine), —NO$_2$, or —C≡N; Z$^2$, Z$^1$, n and n' are as hereinbefore defined;

with the proviso that;

(a) when n=1, either one of Z$^1$ is selected from the group consisting of —CH=CH—, —N=N—, —CO—S—, —S—CO—, —CH=N—, —N=CH—, —O—CO—, —CO—O— and a direct single bond provided that the other Z$^1$ group is selected from this same group or is selected from a group selected from the group consisting of

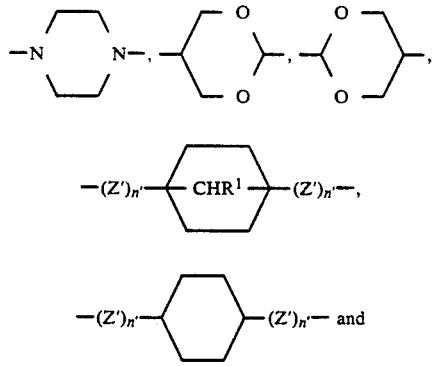

when (i) each n' is zero, or (ii) when one n'=zero and one n'=1 with Z' being —O—CO— or —CO—O— and R$^1$ is a group having only one carbon atom;

(b) when n=2, one or two Z$^1$ groups are independently selected from the group consisting of —CH=CH—, —N=N—, —CO—S—, —S—CO—, —CH=N—, —N=CH—, —O—CO—, —CO—O—, and a direct single bond, provided that the remaining Z$^1$ groups are selected from this group;

(c) when one Z$^1$ is

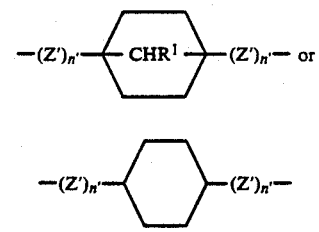

wherein (i) when each n'=1 with each Z' being —O—CO— or —CO—O—, or (ii) when one n'=1 with Z' being —O—CO— or —CO—O— and the other n'=zero resulting in the other Z' being a direct bond and R$^1$ is a group having only one carbon atom, then n must have a value of 1 or 2 and R$^1$ is a group having only one carbon atom: and (B) a curing amount of at least one suitable curing agent for component (A); and wherein said curing is conducted outside the liquid crystal transition temperature range of said epoxy resin and with the proviso that the epoxy resin and curing agent are not simultaneously the diglycidyl ether of 4,4'-dihydroxyphenylbenzoate and 4,4'-diaminophenylbenzoate, respectively.

A further aspect of the present invention pertains to products resulting from curing a curable composition comprising (A) at least one epoxy resin containing one or more rodlike mesogenic moieties said epoxy resin being represented by the following

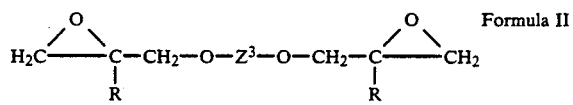

wherein Z$^3$ is

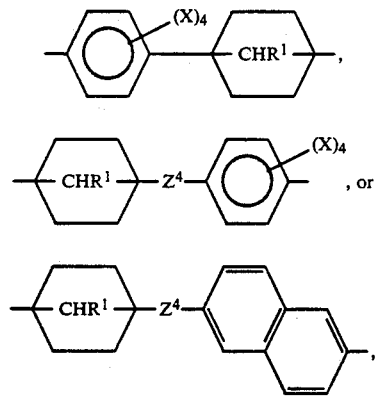

and Z$^4$ is —CO—O—, or —O—CO—; each R is independently hydrogen or an aliphatic hydrocarbon group having from 1 to about 4 carbon atoms; R$^1$ is a group having only one carbon atom; each X is independently hydrogen, a hydrocarbyl or hydrocarbyloxy group having suitably from 1 to about 12, more suitably from 1 to about 6, most suitably from 1 to about 4, carbon atoms, a halogen atom (preferably chlorine or bromine), —NO$_2$, or —C≡N; and (B) a curing amount of at least one suitable curing agent for component (A); and wherein said curing is conducted outside the liquid crystal transition temperature range of said epoxy resin.

A still further aspect of the present invention pertains to products resulting from the application of an electric field, magnetic field, drawing and/or shear flow before and/or during curing or processing of a curable composition comprising (A) at least one epoxy resin containing one or more rodlike mesogenic moieties said epoxy resin being those represented by either the following Formula I

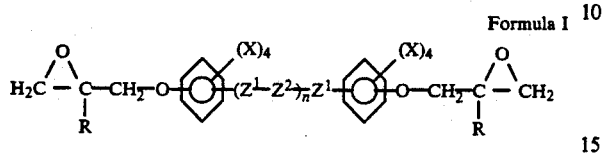

Formula I wherein at least about 80 percent of the $-(Z^1-Z^2)_n-Z^1$-linkages and the glycidyl ether groups are in the para position with respect to each other; each R and $R^1$ is independently hydrogen or an aliphatic hydrocarbon group having from 1 to about 4 carbon atoms; each X is independently hydrogen, a hydrocarbyl or hydrocarbyloxy group having suitably from 1 to about 12, more suitably from 1 to about 6, most suitably from 1 to about 4, carbon atoms, a halogen atom (preferably chlorine or bromine), $-NO_2$, or $-C\equiv N$; each $Z^1$ is independently a direct single bond, $-CR^1=CR^1-$, $-CR^1=CR^1-CR^1=CR^1-$, $-CR^1=N-N=CR^1-$, $-CR^1=CR^1-CO-O-CH_2-$, $-CR^1=CR^1-CO-O-CH_2-CH_2-$, $-CH_2-O-CO-CR^1=CR^1-$, $-CH_2-CH_2-O-CO-CR^1=CR^1-$, $-CR^1=CR^1-CO-O-$, $-O-CO-CR^1=CR^1-$, $-CO-NR^1-$, $-NR^1-CO-$, $-CO-NR^1-NR^1-CO-$, $-C\equiv C-$, $-C\equiv-C-C\equiv C-$, $-N=N-$, $-CO-S-$, $-S-CO-$, $-CR^1=N-$, $-N=CR^1-$, $-CO-CR^1=CR^1-$, $-CR^1=CR^1-CO-$, $-CR^1=CR^1-O-CO-CH_2-$, $-CH_2-CO-O-CR^1=CR^1-$, $-CR^1=CR^1-O-CO-CH_2-CH_2-$, $-CH_2-CH_2-CO-O-CR^1=CR^1-$, $-CH_2-CH_2-CO-O-$, $-O-CO-CH_2-CH_2-$, $-CO-O-CR^1=CR^1-$, $-CR^1=CR^1-O-CO-$, $-O-CO-$, $-CO-O-$,

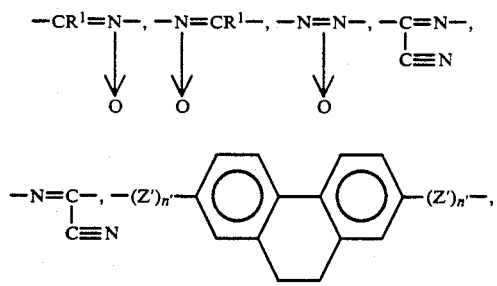

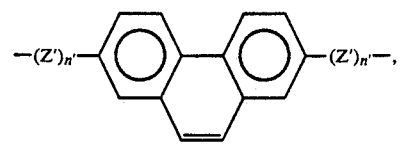

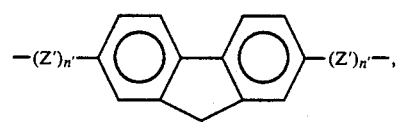

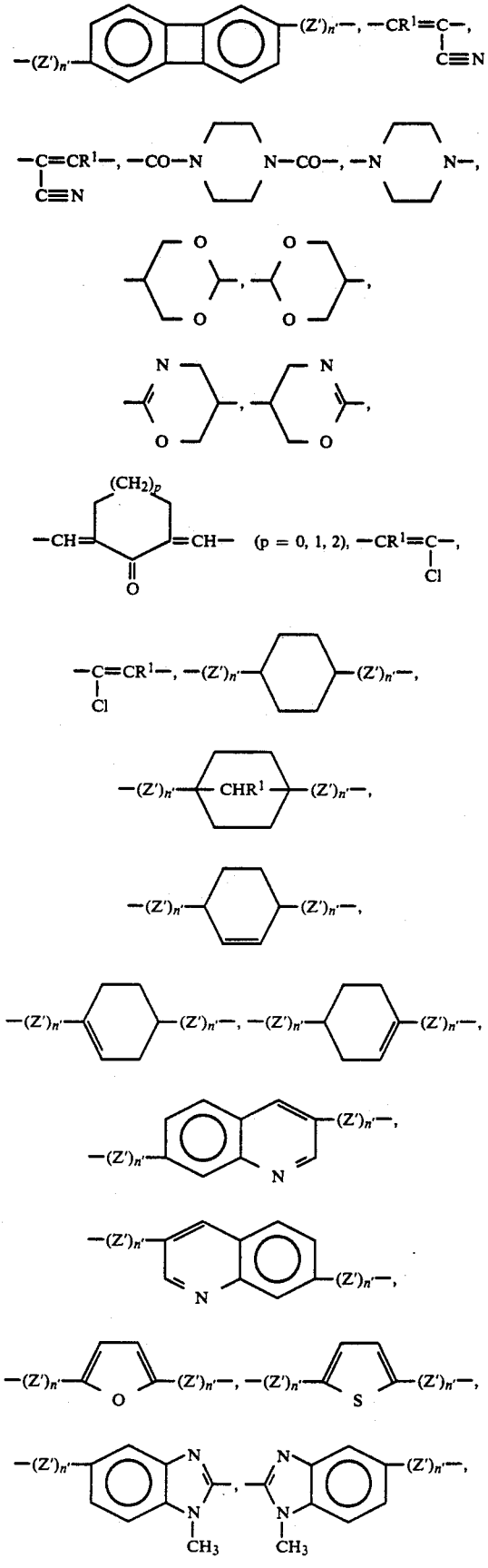

-continued

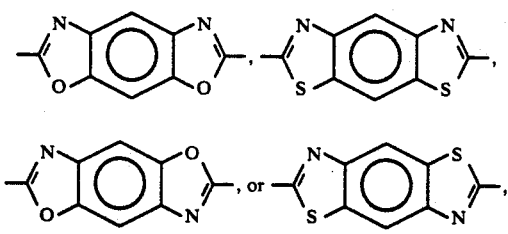

$Z^2$ is a group represented by a cyclic or bicyclic ring system containing from 5 to about 12 carbon atoms and may be cycloaliphatic, polycycloaliphatic, aromatic or a combination thereof; n is 0 to 2; each Z' is independently a —CO—, —O—CO—, —CO—O—, —CO—NR$^1$—, or —NR$^1$—CO— group and each n' independently has a value of zero or one; or the following Formula II

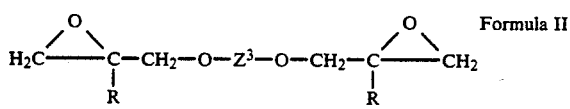

Formula II wherein $Z^3$ is

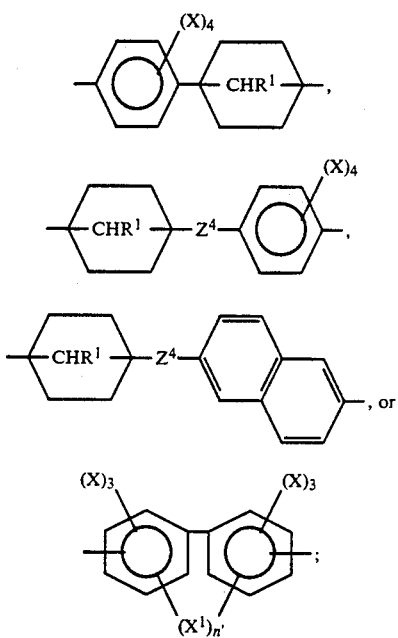

and $Z^4$ is —CO—O—, —O—CO—, —NR$^1$—CO— or —CO—NR$^1$—; $X^1$ is a divalent hydrocarbyl group having from 1 to about 10, preferably from 1 to about 4, carbon atoms which can contain one or more heteroatoms selected from N, O, S and the like and may be saturated or unsaturated; each R and R$^1$ is independently hydrogen or an aliphatic hydrocarbon group having from 1 to about 4 carbon atoms; each X is independently hydrogen, a hydrocarbyl or hydrocarbyloxy group having suitably from 1 to about 12, more suitably from 1 to about 6, most suitably from 1 to about 4, carbon atoms, a halogen atom (preferably chlorine or bromine), —NO$_2$, or —C≡N; and n' is zero or one; and (B) a curing amount of at least one suitable curing agent for component (A).

The term "mesogenic" as is used herein designates compounds containing one or more rigid rodlike structural units which have been found to favor the formation of liquid crystal phases in the case of low molar mass substances. Thus the mesogen or mesogenic moiety is that structure responsible for molecular ordering.

DETAILED DESCRIPTION OF THE INVENTION

The epoxide compositions of the present invention can be prepared by reacting the corresponding hydroxyl containing compound with an epihalohydrin by any suitable means known to those skilled in the art. Suitable such methods are disclosed by Lee and Neville in *Handbook of Epoxy Resins,* McGraw-Hill, (1967) which is incorporated herein by reference in its entirety.

Generally, the hydroxyl containing compound is reacted with an epihalohydrin in the presence of a suitable catalyst and in the presence or absence of a suitable solvent at a temperature suitably from about 0° C. to about 100° C., more suitably from about 20° C. to about 80° C., most suitably from about 20° C. to about 65° C.; at pressures suitably from about 30 mm Hg vacuum to about 100 psia., more suitably from about 30 mm Hg vacuum to about 50 psia., most suitably from about atmospheric pressure to about 20 psia.; and for a time sufficient to complete the reaction, usually from about 1 to about 12, more usually from about 1 to about 5, most usually from about 1 to about 3 hours. This initial reaction unless the catalyst is an alkali metal or alkaline earth metal hydroxide employed in stoichiometric quantities produces a halohydrin intermediate which is then reacted with a basic acting compound to convert the vicinal halohydrin groups to epoxide groups. The resultant product is a glycidyl ether compound.

Suitable epihalohydrins which can be employed to prepare the epoxide compounds of the present invention include, for example, those represented by the following Formula XII

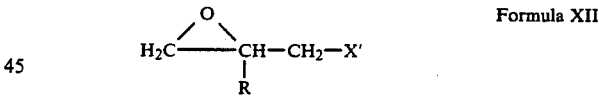

Formula XII wherein R is as previously defined: and X' is a halogen. Particularly suitable such epihalohydrins include, for example, epichlorohydrin, epibromohydrin, epiiodohydrin, methylepichlorohydrin, methylepibromohydrin, methylepiiodohydrin, combinations thereof and the like.

Suitable hydroxyl containing compounds which can be employed to prepare the epoxide compounds of the present invention include, for example, those represented by the following Formulas XIII, XIV, XV or XVI

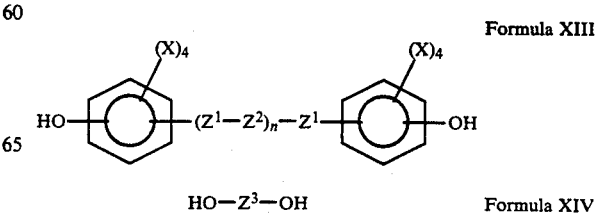

-continued

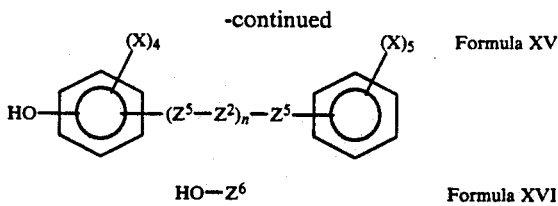
Formula XV

HO—Z⁶    Formula XVI wherein at least about 80 percent of the -(Z¹-Z²)$_n$-Z¹- or -(Z⁵-Z²)$_n$-Z⁵- linkages and the hydroxyl groups are in the para position with respect to each other; n, Z¹, Z², Z³, Z⁵, Z⁶ and X are as previously defined.

Particularly suitable hydroxyl containing compounds include, for example, 4,4'-dihydroxy-α-methylstilbene, 4,4'-dihydroxybenzanilide, 4,4'-dihydroxy-2,2'-dimethylazoxybenzene, 4,4'-dihydroxystilbene, 4,4'-dihydroxyazobenzene, 4,4'-dihydroxyazoxybenzene, 4,4'-dihydroxy-α-cyanostilbene, 4,4'-dihydroxydiphenylacetylene, N,N'-bis(4-hydroxyphenyl)terephthalamide, 4,4'-dihydroxy-3,3',5,5'-tetramethylstilbene, 4,4'-dihydroxy-3,3',5,5'-tetrabromostilbene, 4,4'-dihydroxy-3,3',5,5'-tetramethyl-α-methylstilbene, N-biphenyl-4-hydroxybenzamide, N-2-naphthyl-4-hydroxybenzamide, N-phenyl-4-hydroxybenzamide, N-(4'-hydroxyphenyl)benzamide, 4-hydroxystilbene, 4-hydroxy-α-methylstilbene, 4-hydroxyazobenzene, 4-hydroxy-α-cyanostilbene, 4-hydroxyazoxybenzene, combinations thereof and the like.

Suitable catalysts which can be employed to prepare the epoxide compounds of the present invention include, for example, ammonium halides such as, for example, benzyltrimethylammonium chloride, benzyltrimethylammonium bromide, tetrabutylammonium chloride, tetrabutylammonium bromide, tetraoctylammonium chloride, tetraoctylammonium bromide, tetramethylammonium chloride, tetramethylammonium bromide, combinations thereof and the like.

Suitable basic acting compounds which can be employed to prepare the epoxide compounds of the present invention include, for example, alkali metal or alkaline earth metal hydroxides, carbonates, bicarbonates and the like. Particularly suitable such compounds include, for example, sodium hydroxide, potassium hydroxide, lithium hydroxide, calcium hydroxide, barium hydroxide, magnesium hydroxide, manganese hydroxide, sodium carbonate, potassium carbonate, lithium carbonate, calcium carbonate, barium carbonate, magnesium carbonate, manganese carbonate, sodium bicarbonate, potassium bicarbonate, lithium bicarbonate, calcium bicarbonate, barium bicarbonate, magnesium bicarbonate, manganese bicarbonate, mixtures thereof and the like. Most preferred is sodium hydroxide or potassium hydroxide.

Suitable solvents which can be employed herein include, for example, alcohols, aliphatic hydrocarbons, aromatic hydrocarbons, glycol ethers, amides, sulfoxides, sulfones, combinations thereof and the like. Particularly suitable solvents include, for example, methanol, ethanol, isopropanol, hexane, heptane, octane, nonane, decane, toluene, xylene, ethylene glycol methyl ether, ethylene glycol ethyl ether, ethylene glycol n-butyl ether, ethylene glycol phenyl ether, propylene glycol methyl ether, propylene glycol phenyl ether, tripropylene glycol methyl ether, diethylene glycol methyl ether, diethylene glycol ethyl ether, diethylene glycol n-butyl ether, diethylene glycol phenyl ether, butylene glycol methyl ether, N,N-dimethylformamide, N-methylpyrrolidinone, N,N-dimethylacetamide, dimethylsulfoxide, sulfolane, combinations thereof and the like.

The solvent is usually employed in amounts suitably from about 5 to about 95, more suitably from about 20 to about 60, most suitably from about 30 to about 40, percent by weight based upon the combined weight of solvent and epihalohydrin.

Suitable compounds having an average of more than one active hydrogen atom per molecule which can be employed to prepare the advanced resin compositions of the present invention include, for example, bisphenols, thiobisphenols, dicarboxylic acids and compounds containing one primary amine or amide group or two secondary amine groups such as those represented by Formulas XVII or XVIII.

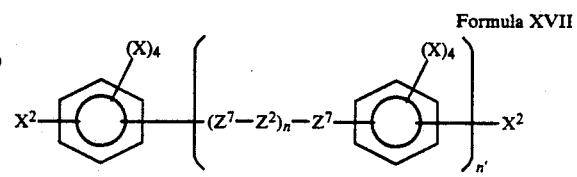
Formula XVII

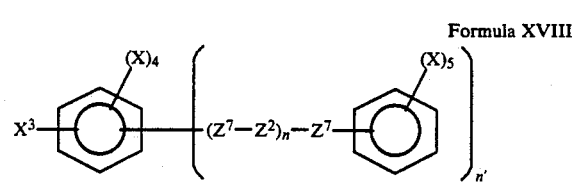
Formula XVIII wherein $X^2$ is independently a hydroxyl, carboxylic acid, —SH, or —NHR² group; R² is an alkyl group having from to about 4 carbon atoms; $X^3$ is $NH_2$—, $NH_2$—$SO_2$—, $NH_2$—CO—, or $NH_2$—$Z^8$—O—; $Z^8$ is an alkyl or cycloalkyl group having from 1 to about 12 carbon atoms; $Z^7$ can independently be a divalent hydrocarbyl group having from 1 to about 10, preferably from 1 to about 4 carbon atoms, —O—, —CO—, —SO—, —$SO_2$—, —S—, —S—S—, —CR¹=CR¹—, —CR¹=CR¹—CR¹=CR¹, —CR¹=N—N=CR¹—, CR¹=CR¹—CO—O—$CH_2$—, —CR¹=C-R¹—CO—$CH_2$—$CH_2$—, —$CH_2$—O—CO—CR¹=C-R¹—, —$CH_2$—$CH_2$—O—CO—CR¹=CR¹—, —CR¹=CR¹—CO—O—, —O—CO—CR¹=CR¹—, —N=N—, —CO—NR¹—, —NR¹—CO—, —CO—NR¹—NR¹—CO—, —C≡C—, —C≡C—C≡C—, —CO—S—, —S—CO—, —CR¹=N—, —N=CR¹—, —CO—O—, —O—CO—, —CR¹=CR¹—CO—, —CO—CR¹=CR¹—, —CR¹=CR¹—O—CO—$CH_2$—, —$CH_2$—CO—O—CR¹=CR¹—, —CR¹=C-R¹—O—CO—$CH_2$—$CH_2$—, —$CH_2$—$CH_2$—CO—O—, —O—CO—$CH_2$—$CH_2$—, —CO—O—CR¹=CR¹—, —CR¹=CR¹—O—CO—, a direct single bond,

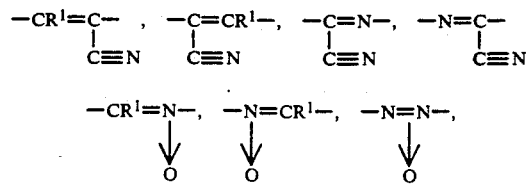

-continued

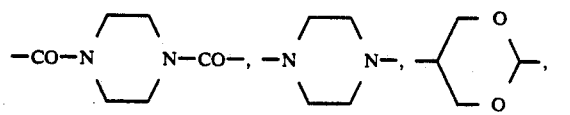

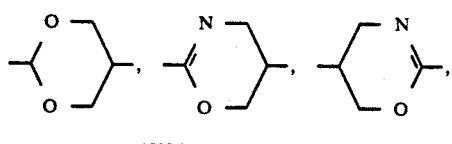

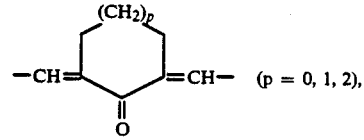

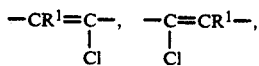

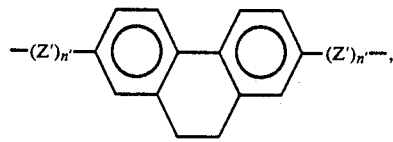

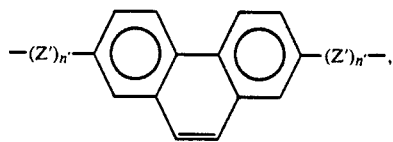

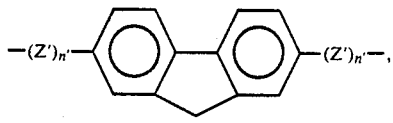

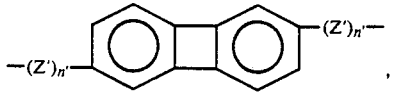

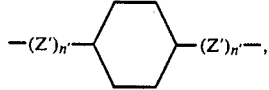

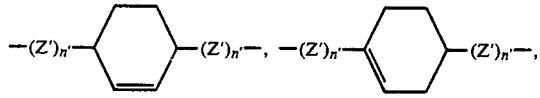

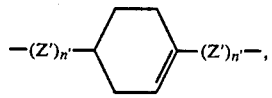

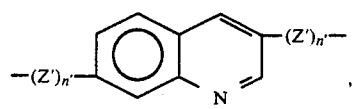

-continued

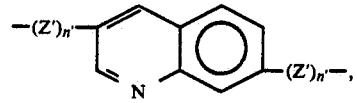

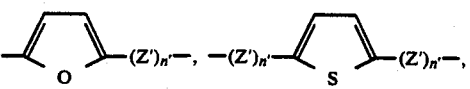

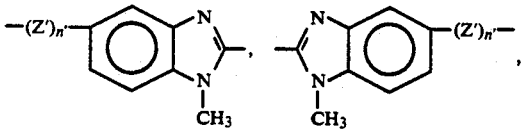

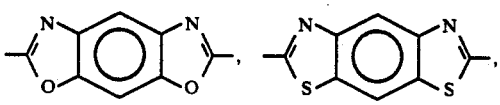

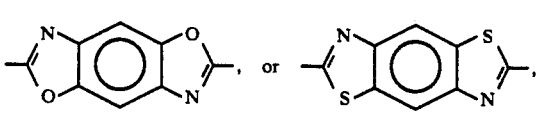

and wherein X, Z', $R^1$, $Z^2$, n and n' are as hereinbefore defined.

The advancement of the epoxy resins containing one or more rodlike mesogenic moieties with compounds having an average of more than one active hydrogen per molecule is employed to linearly chain extend the resin. This linear chain extension is required for some mesogenic-containing resin compositions in order to obtain liquid crystal character. The advancement of the rodlike mesogenic epoxy resins can also be used to increase the temperature range in which a particular resin is liquid crystalline and to control the degree of crosslinking during the final curing stage.

The epoxy resin containing one or more rodlike mesogenic moieties and the compound having an average of more than one active hydrogen atom per molecule are reacted in amounts which provide suitably from about 0.01:1 to about 0.95:1, more suitably from about 0.05:1 to about 0.9:1, most suitably from about 0.10:1 to about 0.50:1 active hydrogen atoms per epoxy group.

Particularly suitable compounds having an average of more than one active hydrogen atom per molecule which can be employed herein include hydroxyl-containing compounds, carboxylic acid-containing compounds and primary amine-containing compounds. These compounds include, for example, those represented by Formulas XVII and XVIII.

Particularly suitable hydroxyl-containing compounds include, for example, hydroquinone, bisphenol A, 4,4'-dihydroxydiphenylmethane, 4,4'-thiodiphenol, 4,4'-sulfonyldiphenol, 4,4'-dihydroxydiphenyl oxide, 4,4'-dihydroxybenzophenone, 1,1-bis(4-hydroxyphenyl)-1-phenylethane, 3,3',5,5'-tetrachorobisphenol A, 3,3'-dimethoxybisphenol A, 4,4'-dihydroxybiphenyl, 4,4'-dihydroxy-α,α'-diethylstilbene, 4,4'-dihydroxy-α-methylstilbene, 4,4'-dihydroxybenzanilide, 4,4'-dihydroxy-2,2'-dimethylazoxybenzene, 4,4'-dihydroxy-α-cyanostilbene, bis(4-hydroxyphenyl)terephthalate, N,N'-bis(4-hydroxyphenyl)terephthalamide, bis(4'-hydroxybiphenyl)terephthalate, 4,4'-dihydroxyphenylbenzoate, bis(4''-hydroxyphenyl)-1,4-benzenediimine, 4,4'''-dihydroxybiphenylbenzoate, 1,4-bis(4'-hydroxyphenyl-1'-carboxamide)benzene, 1,4-bis(4'-hydroxyphenyl-1'-carboxy)benzene, 4,4'-bis(411-hydroxyphenyl-1''-carboxy)biphenyl, mixtures thereof and the like.

Particularly suitable carboxylic acid-containing compounds include, for example, terephthalic acid, 4,4'-benzanilide dicarboxylic acid, 4,4'-phenylbenzoate dicarboxylic acid, 4,4'-stilbenedicarboxylic acid and mixtures thereof and the like.

Particularly suitable primary amine-containing compounds include, for example, aniline, 4'-sulfonamido-N-phenylbenzamide, 4'-sulfonamido-N'-phenyl-4-chlorobenzamide, 4-amino-1-phenylbenzoate, 4-amino-N-phenylbenzamide, N-phenyl-4-aminophenyl-1-carboxamide, phenyl-4-aminobenzoate, biphenyl-4-aminobenzoate, 1-phenyl-4'-aminophenylterephthalate, mixtures thereof and the like.

The advancement reaction can be conducted in the presence of a suitable advancement catalyst such as, for example, phosphines, quaternary ammonium compounds, phosphonium compounds, tertiary amines and the like. Particularly suitable catalysts include, for example, ethyltriphenylphosphonium chloride, ethyltriphenylphosphonium bromide, ethyltriphenylphosphonium iodide, ethyltriphenylphosphonium diacetate (ethyltriphenylphosphonium acetate-acetic acid complex), ethyltriphenylphosphonium phosphate, tetrabutylphosphonium chloride, tetrabutylphosphonium bromide, tetrabutylphosphonium iodide, tetrabutylphosphonium diacetate (tetrabutylphosphonium acetate-acetic acid complex), butyltriphenylphosphonium tetrabromobisphenate, butyltriphenylphosphonium bisphenate, butyltriphenylphosphonium bicarbonate, benzyltrimethylammonium chloride, tetramethylammonium hydroxide, triethylamine, tripropylamine, tributylamine, 2-methylimidazole, benzyldimethylamine, mixtures thereof and the like. Many of these catalysts are described in U.S. Pat. Nos. 3,306,872; 3,341,580; 3,379,684; 3,477,990; 3,547,881; 3,637,590; 3,843,605; 3,948,855; 3,956,237; 4,048,141; 4,093,650; 4,131,633; 4,132,706; 4,171,420; 4,177,216 and 4,366,295, all of which are incorporated herein by reference.

The amount of advancement catalyst depends, of course, upon the particular reactants and catalyst employed; however, it is usually employed in quantities of from about 0.03 to about 3, preferably from about 0.03 to about 1.5, most preferably from about 0.05 to about 1.5 percent by weight based upon the weight of the epoxy-containing compound.

The advancement reaction can be conducted at atmospheric, superatmospheric or subatmospheric pressures at temperatures of from about 20° C. to about 260° C., preferably from about 80° C. to about 240° C., more preferably from about 100° C. to about 200° C. The time required to complete the advancement reaction depends upon the temperature employed. Higher temperatures require shorter periods of time whereas lower temperatures require longer periods of time. Generally, however, times of from about 5 minutes to about 24 hours, preferably from about 30 minutes to about 8 hours, more preferably from about 30 minutes to about 3 hours are suitable.

If desired, the advancement reaction can be conducted in the presence of one or more solvents. Suitable such solvents include, for example, glycol ethers, aliphatic and aromatic hydrocarbons, aliphatic ethers, cyclic ethers, ketones, esters, amides, combinations thereof and the like. Particularly suitable solvents include, for example, toluene, benzene, xylene, methyl ethyl ketone, methyl isobutyl ketone, diethylene glycol methyl ether, dipropylene glycol methyl ether, dimethylformamide, dimethylsulfoxide, N-methylpyrrolidinone, tetrahydrofuran, propylene glycol methyl ether, combinations thereof and the like. The solvents can be employed in amounts of from about zero to about 80%, preferably from about 20% to about 60%, more preferably from about 30% to about 50% by weight based upon the weight of the reaction mixture.

When the epoxy resin containing one or more rodlike mesogenic moieties and the compound having an average of more than one active hydrogen atom per molecule are reacted in amounts which provide from about 0.96:1 to about 1.05:1 active hydrogen atoms per epoxy group, a relatively high molecular weight substantially thermoplastic resinous product is produced. These thermoplastic resin compositions contain little, if any, curable residual epoxide functionality and may even contain an active hydrogen functionality, depending upon which component is employed in excess, the epoxy resin or the active hydrogen containing compound. These phenoxy resins may thus be processed using the typical processing methods employed with conventional thermoplastic resins, such as, for example, injection molding or extrusion. Thermosetting may, however, be induced, for example, via reaction of all or a part of the backbone secondary aliphatic hydroxyl groups produced in the aforesaid advancement reaction, with a curing agent therefor. One class of suitable curing agents includes, for example, the di or polyisocyanates, as well as the blocked di or polyisocyanates which can be induced to react with the secondary hydroxyl groups providing urethane crosslinks between the resin chains. An example of a specific diisocyanate especially useful herein is 4,4'-diisocyanatodiphenylmethane. When the compound having an average of more than one active hydrogen atom per molecule used in the advancement reaction is a diphenol, the resultant resinous product is a phenoxy resin. If desired, the reaction can be conducted in the presence of a suitable catalyst such as, for example, those catalysts described herein for use in the advancement reaction.

According to the teachings found in *ENCYCLOPEDIA OF POLYMER SCIENCE AND ENGINEERING*, vol. 6, page 331, published by John Wiley and Sons, New York, New York (1986), which is incorporated herein by reference, aside from the aforementioned advancement method, a phenoxy resin may also be prepared by reaction of a 1:1 mole ratio of high purity bisphenol A and epichlorohydrin. It is therefore operable to prepare the phenoxy resins containing one or more rodlike mesogenic moieties of the present invention via reaction of one or more diphenols containing one or more rodlike mesogenic moieties with one or more epihalohydrins. A typical material would thus be the phenoxy resin produced from the reaction of epichlorohydrin and 4,4'-dihydroxy-alpha-methylstilbene using the aforementioned stoichiometric ratio. The reaction of the epihalohydrin and the bisphenol is usually conducted at a temperature of from about 0° C. to about 100° C., preferably from about 20° C. to about 80° C., more preferably from about 20° C. to about 65° C. for a time sufficient to complete the reaction, usually from about 1 to about 12, preferably from about 1 to about 5, more preferably from about 1 to about 3 hours.

The compositions of the present invention containing an average of more than one vicinal epoxy group per molecule can be cured with any suitable curing agent for curing epoxy resins such as, for example, primary and secondary polyamines, carboxylic acids and anhydrides thereof, aromatic hydroxyl containing compounds, imidazoles, guanidines, urea-aldehyde resins, melamine-aldehydes resins, alkoxylated urea-aldehyde resins, alkoxylated melamine-aldehyde resins, aliphatic amines, cycloaliphatic amines, aromatic amines, combinations thereof and the like. Particularly suitable curing agents include, for example, methylene dianiline, dicyandiamide, ethylene diamine, diethylenetriamine, triethylenetetramine, tetraethylenepentamine, urea-formaldehyde resins, melamine-formaldehyde resins, methylolated urea-formaldehyde resins, methylolated melamine-formaldehyde resins, phenol-formaldehyde novolac resins, cresol-formaldehyde novolac resins, sulfanilamide, diaminodiphenylsulfone, diethyltoluenediamine, t-butyltoluenediamine, bis-4-aminocyclohexylmethane, isophoronediamine, diaminocyclohexane, hexamethylenediamine, piperazine, aminoethylpiperazine, 2,5-dimethyl-2,5-hexanediamine, 1,12-dodecanediamine, tris-3-aminopropylamine, combinations thereof and the like.

The curing agents are employed in amounts which will effectively cure the composition; however, these amounts will depend upon the particular epoxy resin and curing agent employed. Generally, suitable amounts include, for example, from about 0.95:1 to about 1.2:1 equivalents of curing agent per equivalent of epoxy resin.

The monoepoxide compounds containing one or more rodlike mesogenic moieties of the present invention can be employed as reactive diluents for the polyepoxide resins of the present invention as well as for polyepoxide resins substantially free of rodlike mesogenic moietie(s). For other polyepoxide resins, the monoepoxide compounds provide a means of incorporating into the composition, rodlike mesogenic moieties so as to enhance properties when cured.

The rodlike mesogenic diepoxides of the present invention can also be employed for the purpose of improving the properties Of polyepoxide resins substantially free of rodlike mesogenic moieties. Generally, suitable amounts of rodlike mesogenic epoxy resins are from about 1 to about 99, more suitably from about 10 to about 80, most suitably from about 10 to about 50 weight percent based on the total weight of the combined resins. Representative of the other polyepoxide resins include, for example, the diglycidyl ethers of resorcinol, bisphenol A, 4,4'-dihydroxydiphenylmethane, 3,3',5,5'-tetrabromobisphenol A, 4,4'-thiodiphenol, 4,4'-sulfonyldiphenol, 4,4'-dihydroxydiphenyl oxide, 4,4'-dihydroxybenzophenone, 1,1-bis(4-hydroxyphenyl)-1-phenylethane, 3,3',5,5'-tetrachlorobisphenol A, 3,3'-dimethoxybisphenol A; the triglycidyl ether of tris(hydroxyphenyl)methane; the polyglycidyl ether of a phenol or substituted phetiolaldehyde condensation product (novolac); the polyglycidyl ether of a dicyclopentadiene or an oligomer thereof and phenol condensation product; the advancement reaction products of the aforesaid di- and polyglycidyl ethers with aromatic di- or polyhydroxyl- or, carboxylic acid- containing compounds including, for example, bisphenol A (4,4'-isopropylidenediphenol), o-, m-, p-dihydroxybenzene, 2,4-dimethylresorcinol, 4-chlororesorcinol, tetramethylhydroquinone, 1,1-bis(4-hydroxyphenyl)ethane, 1,1-bis(4-hydroxyphenyl)-1-phenylethane, 4,4'-dihydroxydiphenyl ether, 3,3',5,5'-tetramethyldihydroxydiphenyl ether, 3,3',5,5'-dichlorodihydroxydiphenyl ether, 4,4'-bis-(p-hydroxyphenyl isopropyl)diphenyl ether, 4,4'-bis-(p-hydroxyphenoxy)benzene, 4,4'-bis(p-hydroxyphenoxy)phenoxy)diphenyl ether, 4,4'-bis(4(4-hydroxypheoxy)phenyl sulfone)diphenyl ether, 4,4'-dihydroxydiphenyl sulfone, 4,4'-dihydroxydiphenyl sulfide, 4,4'-dihydroxydiphenyl disulfide, 2,2'-dihydroxydiphenyl sulfone, 4,4'-dihydroxydiphenyl methane, 1,1-bis(p-hydroxyphenyl)cyclohexane, 4,4'-dihydroxybenzophenone, phloroglucinol, pyrogallol, 2.2',5,5'-tetrahydroxydiphenyl sulfone, tris(hydroxyphenyl)methane, dicyclopentadiene diphenol, tricyclopentadiene diphenol; mixtures thereof and the like.

Before and/or during processing and/or curing of the epoxy resin compositions into a part, electric or magnetic fields, drawing and/or shear stresses can be applied for the purpose of orienting the liquid crystal moieties contained or developed therein which in effect improves the mechanical properties. As specific examples of these methods, Finkelmann, et al, *Macromol. Chem.*, 180, 803–806 (March 1979) induced orientation in thermotropic methacrylate copolymers containing mesogenic side chain groups decoupled from the main chain via flexible spacers in an electric field. Orientation of mesogenic side chain groups decoupled from the polymer main chain via flexible spacers in a magnetic field has been demonstrated by Roth and Kruecke, *Macromol. Chem.*, 187, 2655–2662 (November 1986). Magnetic field induced orientation of mesogenic main chain containing polymers has been demonstrated by Moore. at al, *ACS Polymeric Material Sciences and Engineering*, 52, 84–86 (April–May 1985). Magnetic and electric field orientation of low molecular weight mesogenic compounds is discussed by W. R. Krigbaum in *Polymer Liquid Crystals*, pages 275–309 (1982) published by Academic Press, Inc. All of the above are incorporated herein by reference in their entirety.

In addition to orientation by electric or magnetic fields, polymeric mesophases can be oriented by shear forces which are induced by drawing and/or flow through dies, orefices, and mold gates. A general discussion for orientation of thermotropic liquid crystal polymers by this method is given by S. K. Garg and S. Kenig in *High Modulus Polymers*, pages 71–103 (1988) published by Marcel Dekker, Inc. For the mesomorphic systems based on the epoxy resin compositions, this shear orientation can be produced by processing methods such as injection molding, extrusion, pultrusion, filament winding, filming and prepreging.

The rodlike mesogenic epoxy resins of the present invention can be blended with other materials such as solvents or diluents, fillers, pigments, dyes, flow modifiers, thickeners, reinforcing agents, mold release agents, wetting agents, stabilizers, fire retardant agents, surfactants, combinations thereof and the like.

These additives are added in functionally equivalent amounts, e.g., the pigments and/or dyes are added in quantities which will provide the composition with the desired color; however, they are suitably employed in amounts of from about zero to about 20, more suitably from about 0.5 to about 5, MOST suitably from about 0.5 to about 3 percent by weight based upon the weight of the total blended composition.

Solvents or diluents which can be employed herein include, for example, hydrocarbons, ketones, glycol ethers, aliphatic ethers, cyclic ethers, esters, amides, combinations thereof and the like. Particularly suitable solvents or diluents include, for example, toluene, benzene. xylene, methyl ethyl ketone, methyl isobutyl ketone, diethylene glycol methyl ether, dipropylene glycol methyl ether, dimethylformamide, N-methylpyrrolidinone, tetrahydrofuran, propylene glycol methyl ether, combinations thereof and the like.

The modifiers such as thickeners, flow modifiers and the like can be suitably employed in amounts of from zero to about 10, more suitable from about 0.5 to about 6, most suitably from about 0.5 to about 4 percent by weight based upon the weight of the total composition.

Reinforcing materials which can be employed herein include natural and synthetic fibers in the form of woven fabric, mats, monofilament, multifilament, unidirectional fibers, rovings, random fibers or filaments, inorganic fillers or whiskers, hollow spheres, and the like. Suitable reinforcing materials include, glass, ceramics, nylon, rayon, cotton, aramid, graphite, polyalkylene terephthalates, polyethylene, polypropylene, polyesters, combinations thereof and the like.

Suitable fillers which can be employed herein include, for example, inorganic oxides, ceramic microspheres, plastic microspheres, glass microspheres, inorganic whiskers, $CaCO_3$, combinations thereof and the like.

The fillers can be employed in amounts suitable from about zero to about 95, more suitably from about 10 to about 80, most suitable from about 40 to about 60 percent by weight based upon the weight of the total composition.

The following examples are illustrative of the present invention, but are not to be construed as to limiting its scope in any manner.

COMPARATIVE EXPERIMENT A

1. Preparation of a Neat Resin Casting of the Diglycidyl Ether of Bisphenol A

A diglycidyl ether of bisphenol A (50.00 grams) having an epoxide equivalent weight of 175.6 is combined with an equivalent amount of a curing agent, sulfanilamide (12.26 grams). This blend is heated in a 170° C. convection oven for 20 minutes to dissolve all of the sulfanilamide. This resinous mixture is then transferred to a 100° C. oven where it is allowed to cool for 20 minutes. A 70 weight percent solution of tetrabutylphosphonium acetate-acetic acid complex in methanol (0.28 grams, 4480 ppm based on the total weight of the resin mixture) is then added to promote the eventual cure. The resin is next degassed in a vacuum bell jar and then poured into an aluminum mold (dimensions=4.5"×5.0"×0.125"; 114.3 mm×127 mm×3.18 mm) which is contained in a 120° C. convection oven. After one hour at 120° C., the temperature of the oven is increased and held for one hour at 150° C. and 180° C. After one hour at 180° C., the temperature of the oven is increased to 200° C. where it is held for 1.5 hours before cooling to room temperature. At room temperature, a translucent, neat resin casting is obtained from the mold. Differential scanning calorimetry analysis for this polymer shows complete cure. The glass transition temperature, as determined by differential scanning calorimetry, is 185° C. The glass transition temperature, which is also determined by dynamic mechanical analysis, is 186° C. and is in close agreement with the value obtained by differential scanning calorimetry. The tensile storage modulus at 40° C. which is obtained from the dynamic mechanical analysis is 670 MPa (97,150 psi). The flexural strength and modulus determined for this polymer by ASTM Method D790 are 19,960 psi (137.6 MPa) and 472,000 psi (93,254.3 MPa), respectively.

2. Preparation of Cast Films of the Diglycidyl Ether of Bisphenol A

A diglycidyl ether of bisphenol A (30.00 grams) having an epoxide equivalent weight of 179.5 is combined with an equivalent amount of a curing agent, sulfanilamide (7.20 grams). This blend is heated in a 170° C. convection oven for 20 minutes to dissolve all of the sulfanilamide. This resinous mixture is then transferred to a 100° C. oven where it is allowed to cool for 20 minutes. A 70 weight percent solution of tetrabutylphosphonium acetate-acetic acid complex in methanol (0.18 grams, 4810 ppm based on the total weight of the resin mixture) is then added to promote the eventual cure. This resin is next degassed in a vacuum bell jar and then poured into a stainless steel mold (dimensions=7.5"×0.5"×0.021"; 190.5 mm×12.7 mm×0.53 mm) located in a 120° C. convection oven. The mold is then transferred to a mechanical press heated to 120° C. Pressure (approximately 2,000 psi, 13.8 MPa) is applied to this mold within 5 minutes. After one hour at 120° C., the temperature of the press is increased and held for one hour at 150° C. and 180° C. After one hour at 180° C., the temperature of the press is increased to 200° C. where it is held for 1.5 hours before cooling to room temperature. After cooling to room temperature, a translucent film is obtained from the mold. The glass transition temperature for this polymer is 180° C. as determined by thermal mechanical analysis. The average tensile strength and modulus for 5 castings prepared using this procedure are 8,803 psi (60.7 MPa) (standard deviation=860 psi, 5.9 MPa) and 515,000 psi (3,550.8 MPa) (standard deviation=9,000 psi, 62 MPa), respectively.

3. Preparation of a Neat Resin Casting of the Diglycidyl Ether of Bisphenol A and Measurement of Chemical Resistance A diglycidyl ether of bisphenol A (50.00 grams) having an epoxide equivalent weight of 175.6 is combined with an equivalent amount of a curing agent, sulfanilamide (12.26 grams). This blend is heated in a 170° C. convection oven for 20 minutes to dissolve all of the sulfanilamide. This resinous mixture is then transferred to a 100° C. oven where it is allowed to cool for 30 minutes. A 70 weight percent solution of tetrabutylphosphonium acetate-acetic acid complex in methanol (0.28 grams, 4480 ppm based on the total weight of the resin mixture) is then added to promote the eventual cure. The resin is next degassed in a vacuum bell jar and then poured into an aluminum mold (dimensions=4.511×5.011×0.125"; 114.3 mm×127 mm×3.18 mm) which is preheated in a 120° C. convection oven. After 1.5 hours at 120° C., the temperature of the oven is increased and held one hour at 150° C. and 180° C. After one hour at 180° C., the temperature of the oven is increased to 200° C. where it is held for 2 hours before cooling to room temperature. At room temperature, a translucent neat resin casting is obtained from the mold. Differential scanning calorimetry analysis for this polymer showed complete cure. The glass transition temperature, as determined by differential scanning calorimetry is 188° C. From the casting obtained, test coupons which are approximately 0.5" wide by 1.5" long (12.7 mm×38.1 mm) are cut and individually weighed. These coupons are separately immersed in methylene chloride, methylethyl ketone, dimethylformamide and bleach, then maintained therein at room temperature (approximately 23° C.). After immersion for a measured time, the coupons are removed from the chemical, wiped dry and then weighed. For these neat resin coupons of the diglycidyl ether of bisphenol A cured with sulfanilamide, the percent weight gains are 26.6 after 30 days in methylene chloride, 4.1 after 60 days in methylethyl ketone, 5.7 after 30 days in dimethylformamide and 1.0 after 30 days in bleach. The results are reported in Table IV.

4. Preparation of an Injection Molded, Graphite Composite of the Diglycidyl Ether of Bisphenol A A diglycidyl ether of bisphenol A (4.95 grams) having an epoxide equivalent weight of 179.5 is placed in a 160° C. oven. After the resin vias been in the oven for 8 minutes, an equivalent amount of a curing agent. sulfanilamide (1.187 grams), is added. This mixture is periodically stirred over the next 10 minutes to dissolve all the sulfanilamide into to the resin. Chopped graphite fibers (1.083 grams; ¼ inch, 6.35 mm, long) are then added. The graphite fibers used are obtained from Fortafil Fibers, Inc. and the manufacturer's designation for this product is Fortafil ® 3 (c) ¼ 07. After adding the graphite fibers (15 weight percent based on total components), they are mixed with the resin over the next 5 minutes to produce a blend. This blend is next degassed using a vacuum bell jar and then transferred to the reservoir of an injection molder which is temperature controlled at 120° C. After 20 minutes, heating of the molder reservoir is discontinued. When the molder reservoir has cooled to 100° C., the mixture is injected through a ⅛"×3/32" (3–175 mm×2.38 mm) rectangular orifice into a mold (dimensions=3"×0.511×0.12511; 76.2 mm×12.7 mm×3.175 mm) which is preheated to 85° C. This mold is then immediately transferred to an 85° C. oven. After 14.5 hours at 85° C., the oven temperature is increased to 230° C. over a 7 hour period. The oven temperature is then maintained at 230° C. for 4 hours before cooling to room temperature. At room temperature a graphite composite of the diglycidyl ether of bisphenol A cured with sulfanilamide is obtained from the mold. The flexural strength and modulus for this composite are 21,450 psi (147.9 MPa) and 1,179,000 Psi (8,129 MPa), respectively. Differential scanning calorimetry is performed at a heating rate of 10° C. per minute for a sample of the composite (approximately 20 milligrams). This analysis showed a glass transition temperature of 190° C. The results are reported in Table V.

COMPARATIVE EXPERIMENT B

I. Preparation of a Solvent Borne Coating of the Phenoxy Resin of 4,4'-Isopropylidenediphenol and the Diglycidyl ether of 4,4'-Isopropylidenediphenol.

Cyclohexanone (66.7% weight, 29.7 grams) and a commercial grade phenoxy resin prepared from 4,4'-isopropylidenediphenol and the diglycidyl ether of 4,4'-isopropylidenediphenol (33.3% weight, 14.82 grams) is combined to form a solution. This solution is applied to the surface of a 41"×12"×0.3211 (101.6 mm×304.8 mm×8.128 mm) unpolished cold rolled steel panel, which had been washed with methylene chloride, using a number 40 drawdown bar. The coated panel is allowed to dry for twelve hours at room temperature (25°C.) to provide a smooth transparent coating which is free of flaws. Further drying at 100° C. is completed for eight hours, then a sample of the coating is scraped off and examined via crosspolarized light microscopy demonstrating a total lack of birefringence. A portion of the 1 mil thick coated panel is tested for flexibility via the T-bend test using a standard method (ASTM D 4145-83). The temperature at which the specimens are bent is 25° C., with all bends made perpendicular to the direction of the coating drawdown. After the application and removal of the specified pressure sensitive tape to the bent surface, the coating in the bend region is treated for 15 seconds with acidified copper sulfate. After rinsing to remove the acidified copper sulfate, the blotted surface is examined via optical microscopy for defects. The coating failed 0T as evidenced by the penetration of acidified copper sulfate to etch the metal surface, sometimes passed 1T, but consistently passed 2T (no penetration of acidified copper sulfate).

EXAMPLE 1

A. Synthesis of 4,4'-Dihydroxy-alpha-methylstilbene

Phenol (188.22 grams, 2.0 moles) and chloroacetone (102.81 grams. 1.0 mole as chloroacetone) are added to a reactor and cooled to −10° C. with stirring. The chloroacetone used is a technical grade containing 90% chloroacetone. 2.5% acetone, 6.5% 1,1-dichoroacetone and 1.0% 1,3-dichloroacetone. Concentrated sulfuric acid (98.08 grams, 1.0 mole) is added dropwise to the stirred solution over a one hour period in order to maintain the reaction temperature between −10° C. and −11° C. After two hours of post reaction at the −10° C. temperature, the viscous orange oil product is mixed with 500 milliliters of iced deionized water. The oil product is separated then washed with a second 500 milliliter portion of chilled deionized water. After separation, the recovered oil product is added to a 2-liter beaker along with 250 milliliters of ethanol and stirred to provide a solution. Deionized water (250 milliliters) is added to the stirred solution and heating commenced. As the temperature of the mixture increases, the stirred mixture begins to clear. Each time clearing is observed, sufficient deionized water is added to induce cloudiness, followed by continuation of the mixing and heating. Once the temperature reaches 90° C., a massive precipitation of white crystalline plates occurs. At this time, heating and stirring ceases and the mixture is chilled to 5° C. and held therein for 12 hours. The crystalline product is recovered by filtration, washed with two 150 milliliter portions of deionized water, then dried at 90° C. and 5 mm Hg to a constant weight of 103 grams. Nuclear magnetic resonance spectroscopy and infrared spectrophotometric analysis confirms the product structure for 4,4'-dihydroxy-α-methylstilbene.

B. Epoxidation of 4,4'-Dihydroxy-α-methylstilbene 4,4'-dihydroxy-CL-methylstilbene (113.13 grams, 1.0 hydroxyl equivalent) prepared using the method of A above, epichlorohydrin (462.65 grams, 5 moles), deionized water (40.23 grams, 8.0 percent by weight of the epichlorohydrin used) and isopropanol (249.12 grams, 35 percent by weight of the epichlorohydrin used) are added to a reactor and heated to 55° C. with stirring under a nitrogen atmosphere. Once the 55° C. reaction temperature is achieved, sodium hydroxide (36.0 grams, 0.90 mole) dissolved in deionized water (144 grams) is added dropwise to the reactor over a 40 minute period in order to maintain a reaction temperature between 55° and 59° C. Ten minutes after completion of the aqueous sodium hydroxide addition, the stirring is stopped and the aqueous layer which separates from the reaction mixture is pipetted off and discarded. Stirring is resumed and after a total of twenty minutes following completion of the initial aqueous sodium hydroxide addition, a second solution of sodium hydroxide (16.0 grams, 0.40 mole) dissolved in deionized water (64 grams) is added to the reactor over a twenty minute period so as to maintain the 55° C. reaction temperature. Fifteen minutes after completion of the aqueous sodium hydroxide addition, the recovered reaction mixture is added to a separatory funnel and washed with 750 milliliters of deionized water. The separated organic layer is washed a second time (750 milliliters deionized water), recovered and then rotary evaporated under vacuum for 45 minutes at 110° C. then 30 minutes at 130° C. The product is recovered (166.5 grams) as a crystalline off-white solid with an epoxide equivalent weight of 181.46.

C. Characterization of Liquid Crystallinity in the Diglycidyl Ether of 4,4'-Dihydroxy-α-methylstilbene A portion (10.84 milligrams) of the diglycidyl ether of 4,4'-dihydroxy-alpha-methylstilbene from B above is analyzed by differential scanning calorimetry using a heating rate of 10° C. per minute and a temperature range of 30° C. to 150° C. The results are reported in Table I.

TABLE I

DIFFERENTIAL SCANNING CALORIMETRY ANALYSIS OF THE DIGLYCIDYL ETHER OF 4,4'-DIHYDROXY-α-METHYLSTILBENE

| Cycle Designation | Observed Transition Temperatures (°C.) midpoint/range | Enthalpy (J/g) | Comments |
|---|---|---|---|
| First heat (30 to 150° C.) | 73/55–84 | 6.3 | — |
| | 122/84–130 | 41.8 | — |
| First cooling (150 to 30° C.) | —/81–52 | — | 2 unresolved broad, flat peaks |
| Second heat (30 to 150° C.) | 84/48–92 (shoulder at 69) | 31.4 | — |
| | 124/108–132 | 3.6 | — |
| Second cooling (150 to 30° C.) | —/81–52 | — | 2 unresolved broad, flat peaks |

Analysis of the diglycidyl ether via polarized light microscopy is completed using a microscope equipped with a programmable hot stage using a heating rate of 20° C. per minute. The results are reported in Table II.

TABLE II

POLARIZED LIGHT MICROSCOPY ANALYSIS OF THE DIGLYCIDYL ETHER OF 4,4'-DIHYDROXY-α-METHYLSTILBENE

| Cycle Designation | Observed Transition Temperatures (°C.) | Comments |
|---|---|---|
| First heat | 190 | First fluidity noted. |
| | 137 | Isotropization completed. |
| First cooling | 91 | First mobile nematic droplets observed. |
| | 51 | First crystallization noted. |
| Second heat | 63 | First fluidity noted. |
| | 78 | Flows to nematic texture. |
| | 86 | Isotropization completed but minor crystalline fraction still present. |
| | 133 | All crystalline fraction melted. |
| Second cooling | 91 | First mobile nematic droplets observed. |
| | 51 | First crystallization noted. |

The diglycidyl ether is a monotropic liquid crystal with a nematic texture. Two fractions are present: the higher melting crystalline fraction becomes liquid crystalline at 91° C. (microscopic observation) followed by the development of liquid crystallinity in the second, lower melting fraction. This accounts for the broadness and overlapping observed in the cooling cycles by differential scanning calorimetry.

D. Preparation of a Neat Resin Casting of the Diglycidyl Ether of 4,4'-Dihydroxy-α-methylstilbene A diglycidyl ether of 4,4'-dihydroxy-α-methylstilbene (36.56 grams, epoxide equivalent weight of 182.0) prepared using the same method as in B is melted in a 160° C. convection oven. An equivalent amount of a curing agent, sulfanilamide (8.65 grams), is then added to the resin. After all of the sulfanilamide has dissolved (approximately 20 minutes), the mixture is then degassed in a vacuum bell jar and poured into an aluminum mold (dimensions=4.511×5.011×0.125"; 114.3 mm×127 mm×3.18 mm) located in a 100° C. oven. After two hours at 100° C., the temperature of the oven is increased and held for one hour at the following temperatures: 120° C., 140° C., 160° C., 180° C., 200° C. and 220° C. Upon cooling to room temperature, an opaque, cream colored casting is obtained from the mold. Differential scanning calorimetry analysis of this polymer shows no discernable transitions or exothermic activity to 280° C. The apparent glass transition temperature for this polymer, as determined by dynamic mechanical analysis, is 260° C. which is 74° C. higher than that obtained for the diglycidyl ether of bisphenol A in Comparative Experiment A-1. The dynamic mechanical analysis also gives a tensile storage modulus of 950 MPa (137,750 psi) at 40° C. for this polymer which is 40 percent higher than that obtained for the diglycidyl ether of bisphenol A. The flexural strength and modulus obtained for this casting using ASTM Method D790 are 18,900 psi (130.3 MPa) and 493,000 psi (3,399.1 MPa), respectively. These flexural properties are comparable to those obtained for the diglycidyl ether of bisphenol A of Comparative Experiment A-1. The results are reported in Table III.

TABLE III

PROPERTIES OF NEAT RESIN CASTINGS

| PROPERTY | DIGLYCIDYL ETHER OF BISPHENOL A (Comparative Experiment A-1) | DIGLYCIDYL ETHER OF 4,4'-DIHYDROXY-α-METHYL-STILBENE (Example 1-D) |
|---|---|---|
| Glass Transition Temperature, °C. (Dynamic Mechanical Analysis) | 186 | 260 (apparent) |
| Tensile Storage Modulus, MPa (Dynamic Mechanical Analysis) | 670 (97,150 psi) | 950 (137,750 psi) |
| Flexural Strength, | 19,960 | 18,900 |

TABLE III-continued
PROPERTIES OF NEAT RESIN CASTINGS

| PROPERTY | DIGLYCIDYL ETHER OF BISPHENOL A (Comparative Experiment A-1) | DIGLYCIDYL ETHER OF 4,4'-DIHYDROXY-α-METHYL-STILBENE (Example 1-D) |
|---|---|---|
| psi | (137.6 MPa) | (130.3 MPa) |
| Flexural Modulus, psi | 472,000 (3,254.3 MPa) | 493,000 (3,399.1 MPa) |

In addition to the above analysis, a sample of the resinous mixture of the diglycidyl ether of 4,4'-dihydroxy-a-methylstilbene and sulfanilamide which is used to prepare this casting is viewed under an optical microscope (70X magnification) using a cross polarized light source. This sample is heated to 100° C. and held at this temperature to duplicate the initial curing conditions of the casting. After 30 minutes at 100° C., a nematic liquid crystalline texture begins to develop. At this stage of resin advancement, shear pressure is applied by moving the microscope slide cover under which the sample is contained. With the application of this shear pressure, birefringent, fibrous domains are observed to form and orient in one direction.

E. Preparation of a Neat Resin Casting of the Diglycidyl Ether of 4,4'- Dihydroxy-α-Methylstilbene and Measurement of Chemical Resistance A diglycidyl ether of 4,4'-dihydroxy-α-methylstilbene (19.28 grams, epoxide equivalent weight of 179.2) prepared using the same method as in B is melted in a 160° C. convection oven. After melt of this resin has occurred, an equivalent amount of a curing agent, sulfanilamide (4.65 grams), is added. This mixture is periodically stirred over the next 10 minutes to dissolve all the sulfanilamide into the resin. The mixture is then degassed in a vacuum bell jar and poured into an aluminum mold (dimensions=3"×3"×0.125"; 76.2 mm×76.2 mm×3.18 mm) preheated in a 120° C. oven. After two hours at 120° C., the temperature of the oven is increased and held for one hour at the following temperatures: 150° C., 180° C. and 200° C. After one hour at 200° C., the temperature of the oven is increased to 225° C. where it is held for 2 hours before cooling to room temperature. Upon cooling to room temperature, an opaque, cream colored casting is obtained from the mold. Differential scanning calorimetry analysis of this polymer showed no discernable transitions or exothermic activity to 270° C. From the casting obtained, test coupons which are approximately 0.5" wide by 1.5" long (12.7 mm×38.1 mm) are cut and individually weighed. These coupons are separately immersed in methylene chloride, methylethyl ketone, dimethylformamide and bleach, then maintained therein at room temperature (approximately 23° C. After immersion for a measured time, the coupons are removed from the chemical, wiped dry and then weighed. For these neat resin coupons of the diglycidyl ether of 4,4'-dihydroxy-α-methylstillbene cured with sulfanilamide, the percent weight gains are 0.56 after 30 days in methylene chloride, 0.02 after 60 days in methylethyl ketone, 0.67 after 30 days in dimethylformamide and 0.25 after 30 days in bleach. The results are reported in Table IV.

TABLE IV
SOLVENT ABSORPTION FOR NEAT RESIN CASTINGS

| | Diglycidyl Ether of Bisphenol A (Comparative Experiment A-3)* | Diglycidyl ether of 4,4'-Dihydroxy-α-methylstilbene (Example 1-E) |
|---|---|---|
| Percent Weight Gain After 30 Days Immersion in Methylene Chloride | 26.6 | 0.56 |
| Percent Weight Gain After 60 Days Immersion in Methylethyl Ketone | 4.17 | 0.02 |
| Percent Weight Gain After 30 Days Immersion in Dimethylformamide | 5.7 | 0.67 |
| Percent Weight Gain After 30 Days Immersion in Bleach | 1.0 | 0.25 |

*Not an example of the present invention.

F. Preparation of an Injection Molded, Graphite Composite of the Diglycidyl Ether of 4,4'-Dihydroxy-α-methylstilbene A diglycidyl ether of 4,4'-dihydroxy-α-methylstilbene (4.95 grams, epoxide equivalent weight of 177.25) prepared using the same method as in B is placed in a 160°C. oven. After melt of this resin has occurred (approximately 8 minutes), an equivalent amount of a curing agent, sulfanilamide (1.202 grams), is added. This mixture is periodically stirred over the next 10 minutes to dissolve all the sulfanilamide into the resin. Chopped graphite fibers (1.086 grams; 1/4 inch long) are then added. The graphite fibers used are obtained from Fortafil Fibers, Inc., and the manufacturer's designation for this product if Fortafil ® 3 (c) ¼ 0.7. After adding the graphite fibers (15 weight percent based on total components), they are mixed with the resin over the next 5 minutes to produce a blend. This blend is next degassed using a vacuum bell jar and then transferred to the reservoir of in injection molder which is temperature controlled at 120° C. After 20 minutes, heating of the molder reservoir is discontinued. When the molder reservoir has cooled to 100° C., the mixture is injected through a ⅛"×3/32" (3-175 mm×2.38 mm) rectangular orifice into a mold (dimensions=3"×0.511×0.12511; 76.2 mm×12.7 mm×3.18 mm ) which is preheated to 85° C. This mold is then immediately transferred to an 85° C. oven. After 17 hours at 85° C., the temperature is increased to 230° C. over a 7 hour period. The oven temperature is then maintained at 230° C. for 6 hours before cooling to room temperature. At room temperature a graphite composite of the diglycidyl ether of 4,4'-dihydroxy-α-methylstilbene cured with sulfanilamide is obtained from the mold. The flexural strength and modulus for this composite are 27,740 psi (191.3 MPa) and 1,719,000 Psi (11,852.2 MPa), respectively. Differential scanning calorimetry is performed at a heating rate of 10° C. per minute for a sample of the composite (approximately 20 milligrams). This analysis shows no discernable glass transition temperature to 300° C. The results are reported in Table V.

TABLE V
PROPERTIES FOR INJECTION MOLDED, GRAPHITE COMPOSITES

|  | Diglycidyl Ether of Bisphenol A (Comparative Experiment A-4)* | Diglycidyl ether of 4,4'-Dihydroxy-α-methylstilbene (Example 1-F) |
|---|---|---|
| Glass Transition Temperature, °C. (Differential Scanning Calorimetry) | 190 | None Detected |
| Flexural Strength, psi | 21,450 (147.9 MPa) | 27,740 (191.3 MPa) |
| Flexural Modulus, psi | 1,179,000 (8,129 MPa) | 1,719,000 (11,852.2 MPa) |

*Not an example of the present invention.

G. Preparation of a Cured Resin Composition Based on a Mixture of the Diglycidyl ether of 4,4'-Dihydroxy-α-methylstilbene and the Diglycidyl Ether of Bisphenol The diglycidyl ether of 4,4'-dihydroxy-α-methylstilbene (4.9129 grams, epoxide equivalent weight=179.1) prepared using the same method as in B is melted in a 160° C. convection oven. After the resin has melted, an equivalent amount of curing agent, sulfanilamide (1.1809 grams), is added. This blend is periodically stirred over the the next 15 minutes to dissolve all the sulfanilamide. After the sulfanilamide has dissolved, the mixture is removed from the oven and cooled to room temperature. At room temperature, part of this is material (0.2875 grams) is added to an aluminum cup containing 0.2875 grams of a mixture consisting of a diglycidyl ether of bisphenol A (epoxide equivalent weight=175.6) and an equivalent amount of dissolved curing agent (sulfanilamide). The aluminum cup containing the blend of the diglycidyl ether of 4,4'-dihydroxy-α-methylstilbene and the diglycidyl ether of bisphenol A is then placed in a 120° C. convection oven. Another aluminum cup containing 0.46 grams of a control (a mixture of the diglycidyl ether of bisphenol A, an equivalent amount of sulfanilamide and 4480 PPM of tetrabutylphosphonium acetate-acetic acid complex (70 percent solids in methanol) prepared using the same procedure as in Comparative Experiment A-1) is also placed in the 120° C. oven at the same time. In the oven, these two resin systems are stirred during the first 10 minutes and then allowed to gel. After 3 hours at 120° C., the oven temperature is increased and held for one hour at the following temperatures: 150° C., 180° C. and 200° C. After 1 hour at 200° C., the oven temperature is increased to 225° C. where it is held for 2 hours before cooling to room temperature. At room temperature, the two cured resin compositions are removed from the aluminum cups and differential scanning calorimetry analysis is performed for these polymers to determine the glass transition temperature. The glass transition temperature for the control, the diglycidyl ether of bisphenol A cured with sulfanilamide, is 185° C. which reproduces the value obtained in Comparative Experiment A-1. The glass transition temperature for the mixture of the diglycidyl ether of 4,4'-dihydroxy-α-methylstilbene and the diglycidyl ether of bisphenol A cured with sulfanilamide is 211° C. which represents a 26° C. improvement over the control.

EXAMPLE 2

A. Synthesis of 4,4'-Dihydroxybenzanilide

One hundred grams of 4,4'-dihydroxybenzophenone (0.467 mole) is added to 300 milliliters of ethanol in a stirred, 1-liter Erlenmeyer flask. After the 4,4'-dihydroxybenzophenone has dissolved, a solution consisting of 48.6 grams of hydroxylamine hydrochloride (0.699 mole) and 57.4 grams of sodium acetate (0.700 mole) in 70 milliliters of deionized water is added followed by an additional 100 milliliters of ethanol. This mixture is stirred and heated on a hot plate to a gentle refluxing condition (75° C.). After heating for 4 hours, the solution is allowed to cool to room temperature with stirring and then filtered. One hundred milliliters of ethanol is used to wash the filter cake. The total filtrant obtained (600.4 grams) is then concentrated to a weight of 219.2 grams by evaporation of the ethanol and water. This solution is then placed in a stirred 1-liter Erlenmeyer flask to which 600 milliliters of deionized water is added. With the addition of the deionized water, a white precipitate is formed. After 30 minutes of stirring, this solution is filtered. The solids obtained weigh 98.22 grams after drying. Sixty-six grams of this material (4,4'-dihydroxybenzophenone oxime, 0.288 mole) is added to 330 milliliters of glacial acetic acid in a 500 milliliter round bottom flask equipped with a stirrer, water cooled condenser, nitrogen purge and heating mantle. A catalytic amount of toluenesulfonic acid (1.85 grams, 0.027 mole) is next added and the reaction mixture is then heated to 83° C. After heating for approximately 2 hours, a precipitate is formed which is stirred for an additional 2 hours at 87° C. Twenty-five milliliters of deionized water is next added and after 30 minutes, the contents of the reaction flask are transferred to a stirred, 1-liter Erlenmeyer flask. Immediately following this transfer, 400 milliliters of deionized water is added. This solution is stirred for 45 minutes and then filtered. The filter cake obtained is washed with 800 milliliters of deionized water and then dried. The resultant solids, which are a light beige color, weigh 54.82 grams. Fourier transform infrared analysis of this product shows absorbances which are indicative of the structure for 4,4'-dihydroxybenzanilide. Differential scanning calorimetry analysis shows a sharp melt endotherm at 273° C. for the 4,4'-dihydroxybenzanilide thus obtained.

B. Epoxidation of 4,4'-Dihydroxybenzanilide 4,4'-dihydroxybenzanilide (99.6 grams, 0.434 mole) prepared from the method given in A, epichlorohydrin (804.57 grams, 8.70 moles), deionized water (69.96 grams, 8.0 percent by weight of the epichlorohydrin used) and isopropanol (433.23 grams, 35 percent by weight of the epichlorohydrin used) are added to a round bottom flask and heated to 65° C. with stirring under a nitrogen atmosphere. After the temperature has reached 65° C., sodium hydroxide (31.31 grams, 0.78 mole) dissolved in deionized water (125.25 grams) is added dropwise over a one hour period so as to maintain the reaction temperature at 65° C. Fifteen minutes after completion of the aqueous sodium hydroxide addition, the stirring is stopped and the aqueous layer which separated from the reaction mixture is removed and discarded. Stirring is then resumed and a second solution of sodium hydroxide (13.92 grams, 0.35 mole) dissolved in deionized water (55.66 grams) is added over a 30 minute period so as to maintain the reaction temperature at 65° C. Fifteen minutes after completion of the second aqueous sodium hydroxide addition, stirring and heating are stopped and the reaction mixture is transferred to a separatory funnel. The aqueous layer which separated from the reaction mixture is removed and discarded. As the remaining organic layer cools to room temperature, sufficient methylene chloride is added to keep the epoxy resin dissolved in solution. The cooled organic layer obtained is then washed four times with deionized water. The volume of deionized water used during each wash is approximately one half that of the organic layer. The washed organic layer is then rotary evaporated under vacuum at 125° C. The final product obtained after drying is an off-white crystalline solid (142.03 grams, yield=95.8% based on 4,4'-dihydroxybenzanilide) which has a melting point of 180°-185° C. and an epoxide equivalent weight of 178.0.

C. Characterization of the Diglycidyl Ether of 4,4'-Dihydroxybenzanilide for Liquid Crystal Character A sample of the diglycidyl ether of 4,4'-dihydroxybenzanilide prepared in B is heated on a hot stage under an optical microscope (70X magnification) using a cross polarized light source. Melting and clearing to an isotropic state is observed between 179°-185° C. Upon cooling from 185° C., the development of a birefringent phase is first observed at 165° C. which is completed at 160° C. In this temperature range, the resin is still fluid. On further cooling, the resin is observed to crystallize at approximately 150° C.

Differential scanning calorimetry analysis of the diglycidyl ether of 4,4'-dihydroxybenzanilide at a heating rate of 20° C. per minute shows a small endotherm (14 joules/gram) between 150°-170° C. followed by a melt endotherm at 183° C. On cooling at 20° C. per minute, a small broad exotherm is observed between 180° and 148° C. followed by a larger exotherm beginning at 148° C. (−50 joules/gram). These observed transitions change with repeated heating and cooling which is attributed to the slow self-cure of the diglycidyl ether of 4,4'-dihydroxybenzanilide at these temperatures.

To determine the characteristics of the diglycidyl ether of 4,4'-dihydroxybenzanilide when chain extended, 0.2504 grams of this resin containing 6000 ppm tetrabutylphosponium acetate-acetic acid complex (70 percent in methanol) is combined and mixed with 0.67 equivalent of 4,4'-dihydroxybenzanilide (0.1083 gram). This mixture is placed between two glass plates and then heated to 250° C. where an isotropic film is produced. Upon cooling, a birefringent schlieren type texture is observed for this film when viewed under an optical microscope (70× magnification) using a cross polarized light source. These results indicate that a liquid crystal glass can be produced through the advancement and/or cure of the diglycidyl ether of 4,4'-dihydroxybenzanilide.

D. Preparation of Cast Films of the Diglycidyl Ether of 4,4'-Dihydroxybenzanilide Part of the diglycidyl ether of 4,4'-dihydroxybenzanilide prepared from B (4.3925 grams) is combined and mixed with an equivalent amount of a curing agent, sulfanilamide (1.0624 grams). This blend of solids is then placed in a 175° C. convection oven. After melt has occurred (approximately 10 minutes) the resinous mixture is poured into a mold (dimensions=7.5"×0.5"×0.021"; 190.5 mm×12.7 mm×0.53 mm) also located in the same convection oven. This mold is then placed in a mechanical press heated to 130° C. Pressure (approximately 2,000 psi, 13.8 MPa) is then applied to the mold within 5 minutes. After 1.5 hours at 130° C., the temperature of the press is increased and held for one hour at the following temperatures: 160° C., 180° C. and 200° C. After one hour at 200° C., the temperature of the press is raised to 225° C. where it is held for two hours before it is allowed to cool to room temperature. After cooling to room temperature an opaque casting is obtained from the mold. The flash from this casting, which results from excess resin being squeezed from the mold, exhibits a birefringent texture which is oriented in the direction of its flow formation. The apparent glass transition temperature for this polymer is 245° C. as determined by thermal mechanical analysis which is 65° C. higher than that obtained for the diglycidyl ether of bisphenol A in Comparative Experiment A-2. The average tensile strength and modulus for two cast films prepared using this procedure are 12,450 psi (85.8 MPa) (standard deviation=1,460 psi, 10.1 MPa) and 635,000 psi (4,378.2 MPa) (standard deviation=3,500 psi, 24.1 MPa), respectively. These values represent a 41 and 23 percent improvement for these respective properties when compared to those obtained for the diglycidyl ether of bisphenol A in Comparative Experiment A-2. The results are reported in Table VI.

TABLE VI

| | PROPERTIES FOR CAST FILMS | |
|---|---|---|
| PROPERTY | DIGLYCIDYL ETHER OF BISPHENOL A (Comparative Experiment A-2) | DIGLYCIDYL ETHER OF 4,4'-DIHYDROXY-BENZANILIDE (Example 2-D) |
| Glass Transition Temperature, °C. (Thermal Mechanical Analysis) | 180 | 245 (apparent) |
| Tensile Strength, psi | 8,803 (60.7 MPa) | 12,450 (85.8 MPa) |
| Tensile Modulus, psi | 515,000 3,550.8 MPa) | 635,000 4,378.2 MPa) |

EXAMPLE 3

A. Synthesis of 4,4'-Dihydroxy-2,2'-Dimethylazoxybenzene

3-Methyl-4-nitrophenol (15.3 grams, 0.10 mole) in anhydrous tetrahydrofuran (100 milliliters) is added dropwise to a vigorously stirred, refluxing suspension of excess lithium aluminum hydride (6.0 grams) in anhydrous tetrahydrofuran (100 milliliters). After completion of the addition, reflux is maintained for an additional 24 hours. The recovered mixture is poured over crushed ice then extracted with diethyl ether. The ether extract is dried over anhydrous magnesium sulfate followed by rotary evaporation under vacuum to provide a wine red solid identified as 4,4'-dihydroxy-2,2'-dimethylazobenzene by nuclear magnetic resonance spectroscopy. Oxidation of the recovered azo compound is accomplished by dissolution in tetrahydrofuran followed by addition of a 10 mole percent excess of 32% peracetic acid at 25° C. Two hours after addition of the peracetic acid, the solution is poured into a mixture of saturated sodium bisulfite (50 milliliters) and saturated sodium bicarbonate (50 milliliters). The precipitated solid is filtered from the aqueous mixture then recrystallized from deionized water to provide 4,4'-dihydroxy-2,2'-dimethylazoxybenzene (11.0 grams).

B. Epoxidation of 4,4'-Dihydroxy-2,2'-Dimethylazoxybenzene 4,4'Dihydroxy-2,2'-dimethylazoxybenzene (9.0 grams, 0.07 hydroxyl equivalent), epichlorohydrin (64.5 grams, 0.7 mole), deionized water (2.8 grams, 8.0 percent by weight of the epichlorohydrin used) and isopropanol (17.4 grams, 35 percent by weight of the epichlorohydrin used) are added to a reactor and heated to 55° C. with stirring under a nitrogen atmosphere. Once the 55° C. reaction temperature is achieved, sodium hydroxide (2.51 grams, 0.063 mole) dissolved in deionized water (10.0 grams) is added dropwise to the reactor over a 40 minute period in order to maintain the reaction temperature at 55° C. Ten minutes after completion of the aqueous sodium hydroxide addition, the stirring is stopped and the aqueous layer which separated from the reaction mixture is pipetted off and discarded. Stirring is resumed and after a total of twelve minutes following completion of the initial aqueous sodium hydroxide addition, a second solution of sodium hydroxide (1.12 grams, 0.028 mole) dissolved in deionized water (4.5 grams) is added to the reactor over a twenty minute period in order to maintain the 55° C. reaction temperature. Fifteen minutes after completion of the aqueous sodium hydroxide addition, the recovered reaction mixture is added to a separatory funnel and washed with 300 milliliters of deionized water. The separated organic layer is washed a second time (300 milliliters deionized water), recovered and then rotary evaporated under vacuum for 60 minutes at 100° C. The product is recovered as a crystalline mustard yellow colored solid with an epoxide equivalent weight of 202.26 (uncorrected).

C. Characterization of the Diglycidyl Ether of 4,4'-Dihydroxy-2,2'-Dimethylazoxybenzene for Liquid Crystal Character A sample of the diglycidyl ether of 4,4'-dihydroxy-2,2'-dimethylazoxybenzene prepared in B is heated on a hot stage and viewed under an optical microscope (70X magnification) using a cross polarized light source. Softening of this resin is first observed at 50° C. On further heating, a melt is obtained at 86° C. which contains birefringent particles. These birefringent particles begin to disappear at 96° C. and a totally isotropic melt is observed at 102° C. On cooling the resin from 102° C. to room temperature, no liquid crystal textures are observed.

The diglycidyl ether of 4,4'-dihydroxy-2,2'-dimethylazoxybenzene prepared from B (0.1200 gram) is combined and mixed with an equivalent amount of sulfanilamide (0.0255 gram). Sulfanilamide is chosen in this analysis as it is an epoxy curing agent which promotes a degree of linear advancement before final crosslinking. A sample of this curable composition is heated on a hot stage and viewed under an optical microscope (70X magnification) using a cross polarized light source. At 170° C., an isotropic melt is obtained which sets after approximately 15 minutes at this temperature. After one hour at 170° C., the temperature is increased to 200° C. where it is held for 40 minutes before cooling to room temperature. Upon cooling to room temperature, a birefringent schlieren type pattern is observed which indicates the formation of a polymer which is a liquid crystalline glass.

EXAMPLE 4

A. Synthesis of 4,4'-Dihydroxy-alpha-methylstilbene

Phenol (376.44 grams, 4.0 moles), chloroacetone (192.77 grams, 2.0 moles as chloroacetone) and methylene chloride (300 grams) is added to a reactor and cooled to −100° C. with stirring. The chloroacetone used is a commercial grade containing 96% chloroacetone. Concentrated sulfuric acid (196.16 grams, 2.0 mole) is added dropwise to the stirred solution over a thirty seven minute period so as to maintain the reaction temperature between −10° and −11° C. After 143 minutes of post reaction between a −10° to −11° C. temperature range, the viscous, orange colored oil product was mixed with iced deionized water (500 milliliters). The oil product is separated then washed with a second portion (500 milliliters) of deionized water. After separation, the recovered oil product is added to a 2 liter beaker along with ethanol (250 milliliters) and stirred to provide a solution. Deionized water (250 milliliters) is added to the stirred solution and heating commences. As the temperature of the mixture increases, the stirred mixture begins to clear. Each time clearing is observed, sufficient deionized water is added to induce cloudiness, followed by continuation of the mixing and heating. Once the temperature reaches 70° C., a massive precipitation of white crystalline plates occurs and is followed by immediate coalescence of the precipitated product to an oil. The oil layer is recovered by decantation of the water layer and ethanol (250 milliliters) is added. Deionized water is again added to the stirred solution as heating commences, in the amount sufficient to induce cloudiness each time clearing is observed. Once the temperature reaches 90° C., a massive precipitation of white crystalline plates again occurs. At this time, stirring is stopped and the crystalline product is chilled to 4° C. and held therein for 12 hours. The crystalline product is recovered by filtration of the chilled crystalline slurry and combined with deionized water (800 milliliters), then stirred with heating to 90° C. After maintaining the stirred slurry at 90° C. for five minutes, the crystalline product is recovered by filtration. The crystalline product is again combined with deionized water (800 milliliters), then stirred with heating to 90° C. After maintaining the stirred slurry at 90° C. for five minutes, the crystalline product is recovered by filtration and then dried in a vacuum oven at 100° C. and 5 mm Hg to a constant weight of 190.0 grams of light tan colored crystalline solid. Proton magnetic resonance spectroscopy and infrared spectrophotometric analysis confirmed the product structure.

B. Epoxidation of 4,4-Dihydroxy-alpha-methylstilbene 4,4'-Dihydroxy-alpha-methylstilbene (152.73 grams, 1.35 hydroxyl equivalents) from A above, epichlorohydrin (624.58 grams, 6.75 moles), deionized water (54.31 grams, 8.0 percent by weight of the epichlorohyrin used) and isopropanol (336.31 grams, 35 percent by weight of the epichlorohydrin used) is added to a reactor and heated to 55° C. with stirring under a nitrogen atmosphere. Once the 55° C. reaction temperature is achieved, sodium hydroxide (48.6 grams, 1.22 moles) dissolves in deionized water (194.4 grams) is added dropwise to the reactor over a 45 minute period so as to maintain reaction temperature between 55° and 59° C.

Ten minutes after completion of the aqueous sodium hydroxide addition, the stirring is stopped and the aqueous layer which separated from the reaction mixture is pipetted off and discarded. Stirring is resumed and after a total of twenty minutes following completion of the initial aqueous sodium hydroxide addition, a second solution of sodium hydroxide (21.6 grams, 0.54 mole) dissolved in deionized water (86.4 grams) is added to the reactor over a twenty minute period so as to maintain the 55° C. reaction temperature. Fifteen minutes after completion of the aqueous sodium hydroxide addition, the recovered reaction mixture is added to a separatory funnel and washed with 750 milliliters of deionized water. The separated organic layer is washed a second time (750 milliliters deionized water), recovered and then rotary evaporated under vacuum for 45 minutes at 110° C. then 30 minutes at 130° C. The product is recovered (218.6 grams) as a crystalline solid with an epoxide equivalent weight of 183.33.

C. Characterization of Liquid Crystallinity in the Diglycidyl Ether of 4,4'-Dihydroxy-alpha-methylstilbene A portion (13.12 milligrams) of the diglycidyl ether of 4,4'-dihydroxy-alpha-methylstilbene from B above is analyzed by differential scanning calorimetry using a heating rate of 10° C. per minute and a temperature range of 30° to 150° C. The results are reported in Table VII:

TABLE VII

| Cycle Designation | Observed Transition Temperatures (°C.) midpoint/range | Enthalpy (J/g) | Comments |
|---|---|---|---|
| First heating (30 to 150° C.) | 127/101–138 | 72.7 | single endotherm |
| First cooling (150 to 30° C.) | 89/92–78 | 1.8 | single endotherm |
|  | 44/54–36 | 21.2 | single endotherm |
| Second heating (30 to 150° C.) | 82/72–96 | 26.0 | single endotherm |
|  | 126/96–138 | 61.9 | single endotherm |
| Second cooling (150 to 30° C. | 89/92–73 | 3.0 | single endotherm |
|  | 44/54–36 | 21.8 | single endotherm |

Analysis of the diglycidyl ether via crosspolarized light microscopy was completed using a microscope equipped with a programmable hot stage using a heating rate of 10° C. per minute. The results are reported in Table VIII:

TABLE VIII

| Cycle Designation | Observed Transition Temperatures (°0) | Comments |
|---|---|---|
| First heating (25 to 136° C.) | 30 | Birefringent crystalline solid. |
|  | 107 | First fluidity noted, birefringent crystals moving in an isotropic fluid. |
|  | 135 | Isotropization completed. |
| First cooling (136 to 30° C.) | 94 | First mobile nematic droplets observed |
|  | 56.5 | Crystallizes. |
| Second heating (30 to 136° C.) | 77 | First fluidity noted, birefringent crystals moving in an isotropic fluid. |
|  | 132 | Isotropization completed. |
| Second cooling (129 to 30° C.) |  | droplets observed. |
|  | 57 | Crystallizes. |

The diglycidyl ether is a monotropic liquid crystal with a nematic texture. The nematic fluid gives opalescence when stirred between the 94° and 56.5° C. temperatures of the first cooling cycle.

D. Characterization of Liquid Crystallinity in the Phenoxy Resin Prepared via in situ Reaction of 4,4'-Dihydroxy-alpha-methylstilbene and the Diglycidyl Ether of 4,4'-Dihydroxy-alpha-methylstilbene A diglycidyl ether of 4,4'-dihydroxy-alpha-methylstilbene (0.25 gram, 0.0014 epoxide equivalent) prepared using the method of B above and having an epoxide equivalent weight of 176.81, 4,4'-dihydroxy-alpha-methylstilbene (0.16 gram, 0.0014 hydroxyl equivalent) prepared using the method of A above and acetone (20 milliliters) to which tetrabutylphosphonium acetate-acetic acid complex (70% solids in methanol) (0.0075 gram) has been added is mixed to provide a solution. The resultant solution is evaporated to provide a dry solid which is then ground to a fine homogeneous powder. A portion of the powder on a microscope slide is analyzed via crosspolarized light microscopy using a microscope equipped with a programmable hot stage and using a heating rate of 10° C. per minute to 131° C. then held therein. At 131° C., a totally isotropic fluid forms. After one minute at 131° C., a birefringent phase with a rodlike appearance is observed. After two minutes at 131° C., the birefringent, rodlike appearance increases and stir opalescence is present. After five minutes at 131° C., the product becomes an opaque, birefringent solid. Heating of the opaque, birefringent solid to 250° C. produces no further changes in its appearance. Upon cooling to 25° C., the solid product retains its opaque and birefringent appearance.

E. Preparation of Phenoxy Resin of 4,4'Dihydroxy-alpha-methylstilbene and the Diglycidyl Ether of 4,4'-Dihydroxy-alpha-methylstilbene and a Solvent Borne Coating thereof A portion (5.6566 grams, 0.05 hydroxyl equivalent) of 4,4'-dihydroxy-alpha-methylstilbene from A above, a portion (9.1666 grams, 0.05 epoxide equivalent) of the diglycidyl ether of 4,4'-dihydroxy-alpha-methylstilbene from B above and cyclohexanone (50.0 grams) is added to a reactor and heated with stirring under a nitrogen atmosphere to provide a 90° C. solution. Once the 90° C. reaction temperature is achieved, ethyltriphenylphosphonium acetate-acetic acid complex (70% solids in methanol) (0.0297 gram, 0.20% wt. of the diphenol and diglycidyl ether reactants used) is added to the reactor and heating continues to 130° C. After eight hours at the 130° C. temperature, the reaction product is recovered as a transparent, viscous solution. Cyclohexanone is evaporated from the product solution to provide 33.3% by weight phenoxy resin (14.82 grams) in 66.7% weight cyclohexanone (29.7 grams). This solution is applied to the surface of a 4×12×0.32 inch (101.6 mm×304.8 mm×8.128 mm) unpolished cold rolled steel panel, which has been washed with methylene chloride, using a number 40 drawdown bar. The coated panel is allowed to dry for twelve hours at room temperature (25° C.) to provide a smooth opaque coating which is free of flaws. Further drying at 100° C. is completed for eight hours, then a sample of the coating is scraped off and examined via crosspolarized light microscopy demonstrating birefringence. A portion of the 1 mil thick coated panel is tested for flexibility via the T-bend test using a standard method (ASTM D 4145-83). The temperature at which the specimens are bent is 25° C. with all bends made perpendicular to the direction of the coating drawdown. After the application and removal of the specified pressure sensitive tape to the bent surface, the coating in the bend region is treated for 15 seconds with acidified copper sulfate. After rinsing to remove the acidified copper sulfate, the blotted surface is examined via optical microscopy for defects. The coating failed TO as evidenced by the penetration of acidified copper sulfate to etch the metal surface, but consistently passed 1T (no penetration of acidified copper sulfate).

EXAMPLE 5

A. Synthesis of 41-Hydroxyphenyl-4-hydroxybenzoate

Hydroquinone (286.0 grams, 2.6 mole), p-hydroxybenzoic acid (179.4 grams, 1.3 mole), diethylbenzene (52 grams) and p-toluenesulfonic acid (0.64 gram) is added to a one liter glass resin kettle reactor and heated to 200° C. with stirring under a nitrogen atmosphere flowing at a rate of one liter per minute. The reactant slurry becomes an amber colored solution once the reaction temperature reaches 165° C. Water and diethylbenzene azeotropically distilled from the reactor is collected in a Dean Stark trap interspersed between the reactor and a chilled water condenser. After 45 minutes at the 200° C. reaction temperature, distillation has ceased, and the reaction product is poured into an aluminum foil tray. The resultant solid product is ground to a fine powder then is stirred in methanol (1200 milliliters) and brought to a boil. After boiling for 15 minutes, the slurry is filtered while still hot. Deionized water (6 liters) is added to the recovered methanol solution and the resultant white precipitate recovered by filtration. The precipitate is redissolved in stirred, boiling methanol (1200 milliliters) then reprecipitated via the addition of deionized water (6 liters). The resultant white precipitate recovered by filtration is redissolved in stirred, boiling methanol (1000 milliliters) then the solution cooled to room temperature (25° C.) and filtered. Reprecipitation is completed by addition of the filtered solution to deionized water (5 liters). The white precipitate is recovered by filtration then dried under vacuum for 12 hours at 90° C. to a constant weight of 125.1 grams. Fourier transform infrared spectrophotometric analysis of a potassium chloride pellet of the product and high pressure liquid chromatographic analysis confirms the product structure for 4'-hydroxyphenyl-4-hydroxybenzoate. Differential scanning calorimetry of a portion of the product (17 milligrams) heated at 10° C. per minute under nitrogen flowing at 35 cubic centimeters per minute reveals a sharp melting point endotherm with a minimum at 246.8° C.

B. Epoxidation of 4'Hydroxyphenyl-4-hydroxybenzoate

4'-Hydroxyphenyl-4-hydroxybenzoate (41.44 grams, 0.18 mole) from A above, epichlorohydrin (499.66 grams, 5.4 mole) and tetrabutylammonium chloride (0.725 gram, 1.75% wt. of the diphenol reactant used) is added to a one liter glass round bottom reactor and heated to 60° C. with magnetically driven stirring under a nitrogen atmosphere flowing at a rate of one liter per minute. The reactant slurry becomes a hazy, amber colored solution after eight hours at the 60° C. reaction temperature. After 23 hours at 60° C., high pressure liquid chromatographic analysis of a portion of the light amber colored solution demonstrates greater than 99.5 area % conversion of the diphenol to reaction product. At this time, a water separator is interspersed between the reactor and the chilled ($-2.5°$ C.) glycol condenser and an addition funnel containing sodium hydroxide (16.2 grams, 0.405 mole) dissolved in deionized water (19.8, 55 % wt. of the solution) and a vacuum line is added to the reactor. The nitrogen purge is shut off simultaneous with initiation of the vacuum. The vacuum and reaction temperature are equilibrated at 90 mm Hg and 60° C., respectively and such that a vigorous reflux is maintained with continuous return of dry epichlorohydrin from the water separator to the reactor. After equilibration, dropwise addition of the aqueous sodium hydroxide commences accompanied by a gradual reduction in vacuum and reaction temperature. After 80 minutes, addition of the aqueous sodium hydroxide is complete and vacuum and reaction temperature are at 70 mm Hg and 56° C., respectively. After an additional 3 hours at the 70 mm Hg vacuum and 56° C. reaction temperature, heating ceases and the product slurry is cooled to 50° C. The recovered slurry is filtered under a nitrogen atmosphere and the resultant light amber colored solution rotary evaporated under a vacuum (2 mm Hg final conditions) at 50° C. for 30 minutes. The viscous oil product (57.6 grams) is dissolved in acetonitrile (36 milliliters) then with stirring under a nitrogen atmosphere, anhydrous methanol (180 milliliters) is added. After chilling for 12 hours at 0° C., the product solidifies to a crystalline mass which is filtered after warming to room temperature (24° C.). The recovered solid is recrystallized from a solution prepared by addition of isopropanol (25 milliliters) and acetonitrile (25 milliliters). After filtration the white crystalline product is dried under vacuum to a constant weight of 19.3 grams. Titration of a portion of the product reveals an epoxide equivalent weight of 177.25. Fourier transform infrared spectrophotometric analysis of a neat film of the product on a sodium chloride plate confirms the product structure for the diglycidyl ether of 4'-hydroxyphenyl-4-hydroxyphenylbenzoate (ester carbonyl absorbance at 1729 cm$^{-1}$, epoxide —C—O— stretching absorbance at 852 and 912 cm$^{-1}$).

C. Characterization of Liquid Crystallinity in the Diglycidyl Ether of 4'-Hydroxyphenyl-4-hydroxybenzoate Analysis of the diglycidyl ether of 4'-hydroxyphenyl-4-hydroxybenzoate via crosspolarized light microscopy is completed using a microscope equipped with a programmable hot stage using a heating rate of 20° C. per minute. The results are reported in Table IX.

TABLE IX

CROSSPOLARIZED LIGHT MICROSCOPY ANALYSIS OF THE DIGLYCIDYL ETHER OF 4'-HYDROXYPHENYL-4-HYDROXYBENZOATE

| Cycle Designation | Observed Transition Temperatures (°C.) | Comments |
|---|---|---|
| First heating (25 to 118° C.) | 30 | Birefringent crystalline solid. |

TABLE IX-continued
CROSSPOLARIZED LIGHT MICROSCOPY ANALYSIS OF THE DIGLYCIDYL ETHER OF 4'-HYDROXYPHENYL-4-HYDROXYBENZOATE

| Cycle Designation | Observed Transition Temperatures (°C.) | Comments |
| --- | --- | --- |
| | 95 | Softening noted. |
| | 105 | First fluidity noted. |
| | 118 | Isotropization completed. |
| First cooling (118 to 30° C.) | 72 | First mobile nematic texture formed. |
| | 59 | First crystallization noted. |

The diglycidyl ether is a monotropic liquid crystal with a nematic texture.

D. Preparation of Phenolic Cured Casting of the Diglycidyl Ether of 4'-Hydroxyphenyl-4-hydroxybenzoate and 4'-Hydroxyphenyl-4-hydroxybenzoate A portion (0.3497 gram, 0.00197 epoxide equivalent) of the diglycidyl ether of 4'-hydroxyphenyl-4-hydroxybenzoate from B above and a portion of 4'-hydroxyphenyl-4-hydroxybenzoate (0.2271 gram, 0.00197 hydroxyl equivalent) from A above are dissolved in acetone (30 milliliters) containing tetrabutylphosphonium acetate-acetic acid complex (70 percent in methanol) (0.0018 grams, 0.37 phr based on the diglycidyl ether reactant used). After mixing the solution for 10 minutes, a homogeneous powder mixture is recovered by evaporation of the acetone solvent under vacuum at 40° C. Differential scanning calorimetry analysis of a portion (11.9 milligrams) of the powder heated at 10° C. per minute under nitrogen flowing at 35 cubic centimeters per minute reveals an exotherm (182 joules per gram) between 125° C. to 174° C. A portion of the powder is placed between two glass plates and heated at 20° C. per minute to 160° C. at which point an isotropic melt is observed via optical microscopy (70× magnification) under crosspolarized light. Following formation of the isotropic melt, a nematic liquid crystalline morphology and stir opalescence are produced by holding the resin at the 160° C. temperature for 6 minutes. After formation of the liquid crystal phase, the resin is cooled from 160° C. at 10° C. per minute. At 140° C., shear is applied to the resin by moving the glass coverslip across the top of the resin. As a result of the application of shear, uniaxial orientation of the liquid crystal domains is visually observable. On further cooling, the resin remained fluid to 110° C. and then became an opaque semi-solid which exhibited a high level of birefringence.

For the preparation of a cured casting, the remaining powder is transferred to an aluminum cup. The aluminum cup is placed in an oven which has been preheated to 160° C. and the powder is observed to melt to an opaque liquid which exhibited stir opalescence. After 12 minutes at 160° C., the oven temperature is reduced to 110° C. and maintained therein for 12 hours before cooling to room temperature (22° C.). After cooling to room temperature, an opaque casting is recovered from the aluminum cup. This casting exhibits a high level of birefringence when viewed by optical microscopy (70× magnification) under crosspolarized light. Differential scanning calorimetry of a portion of the casting using the aforementioned conditions reveales a glass transition temperature of 90.2° C. This glass transition temperature is increased to 95.4° C. by postcuring the casting at 160° C. for six hours. The postcured casting is opaque and exhibits a high level of birefringence.

EXAMPLE 6

A. Characterization of the Diglycidyl Ether of 4,4'-Dihydroxybiphenyl for Liquid Crystal Character A sample of a diglycidyl ether of 4,4'-dihydroxybiphenyl is heated on a hot stage at 10° C. per minute and viewed under an optical microscope (70X magnification) using a crosspolarized light source. Fluidity of this resin is first observed at 160° C. and at this temperature some crystals are still present. On further heating an isotropic melt is obtained at 169° C. On cooling the resin from 175° C. to room temperature at 10° C. per minute, no liquid crystal textures are observed. At 152° C. the resin crystallizes to a solid.

B. Preparation of an Oriented Film of the Diglycidyl Ether of 4,4'-Dihydroxybiphenyl During Cure A diglycidyl ether of 4,4'-dihydroxybiphenyl (0.5721 grams, 0.00371 epoxide equivalents( and sulfanilamide (0.1500 grams, 0.00371 amine equivalents) are combined and ground together to form a homogeneous powder mixture. Differential scanning calorimetry analysis of a portion (12.7 milligrams) of the powder heated at 10° C. per minute under nitrogen flowing at 35 cubic centimeters per minute reveals a cure exotherm (348 joules per gram) between 150° C. and 250° C. A portion of the powder is placed between two glass plates and heated on a hot stage to 170° C. At 170° C. an isotropic melt is observed via optical microscopy (70× magnification) under crosspolarized light. After holding the resin at 170° C. for seven minutes, a smectic liquid crystal texture (focal conical domains) is produced. At this point shear is applied to the resin by moving one of the glass plates across the top of the resin. As a result of the application of shear, uniaxial orientation of the liquid crystal domains is Visually observable at 70× magnification under crosspolarized light. This oriented morphology is maintained with continued cure of the resin.

What is claimed is:

1. A curable composition comprising (I) an advanced epoxy resin composition prepared by reacting
   (A) one or more epoxy resins containing one or more rodlike mesogenic moieties, said epoxy resin being those represented by either the following Formula I

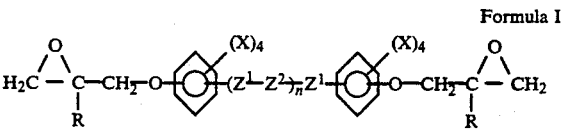

Formula I wherein at least about 80 percent of the -(Z$^1$-Z$^2$)$_n$-Z$^1$- linkages and the glycidyl ether groups are in the para position with respect to each other; each R and R$^1$ is independently hydrogen or an aliphatic hydrocarbon group having from 1 to about 4 carbon atoms; each X is independently hydrogen, a hydrocarbyl or hydrocarbyloxy group having from 1 to about 12 carbon atoms, a halogen atom, —NO$_2$, or —C≡N; each Z$^1$ is independently —CR$^1$=CR$^1$—, —CR$^1$=CR$^1$—CR$^1$=CR$^1$—, —CR$^1$=N—N=CR$^1$—, —CR$^1$=C-R$^1$—CO—O—CH$_2$—, —CR$^1$=C-R$^1$—CO—O—CH$_2$—CH$_2$—, —CH- $_2$—O—CO—CR$^1$=CR$^1$—, —CH$_2$—CH$_2$—O—CO—CR$^1$=CR$^1$—, —CR$^1$=CR$^1$—CO—O—, —O—CO—CR$^1$=CR$^1$—, —CO—NR$^1$—, —NR$^1$—CO—, —CO—NR$^1$—NR$^1$—CO—, —C≡C—, —C≡C—C≡C—, —N=N—, —CO—S—, —S—CO—, —CR$^1$=CR$^1$—O—CO—CH$_2$—, —CH$_2$—CO—O—CR$^1$=CR$^1$—, —CR$^1$=CR$^1$—O—CO—CH$_2$—CH$_2$—, —CH$_2$—CH$_2$—CO—O—CR$^1$=CR$^1$—, —CH$_2$—CH$_2$—CO—O—, —O—CO—CH$_2$—CH$_2$—, —CO—O—CR$^1$=CR$^1$—, —CR$^1$=CR$^1$—O—CO—, a direct single bond when n≧1,

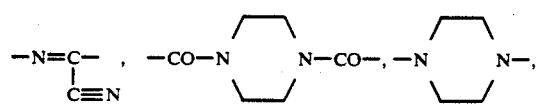

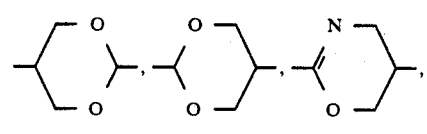

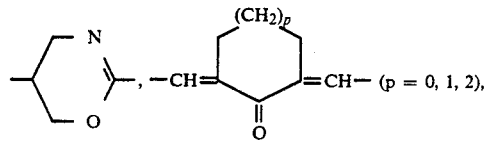

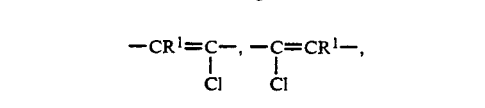

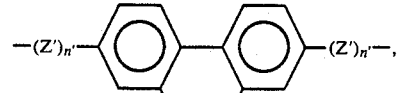

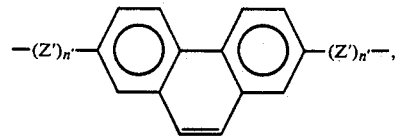

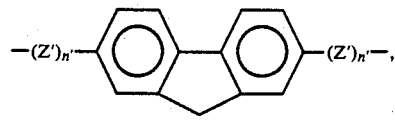

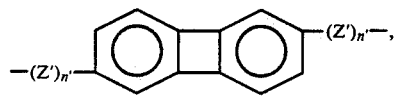

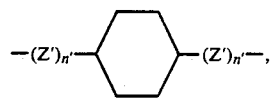

-continued

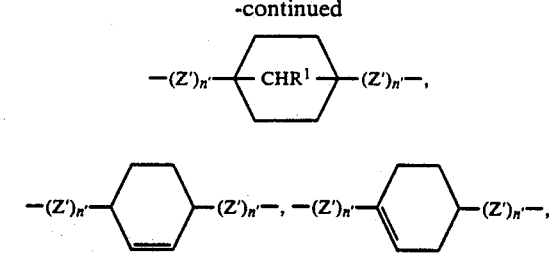

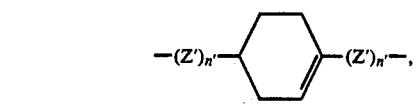

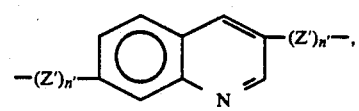

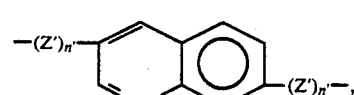

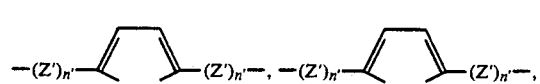

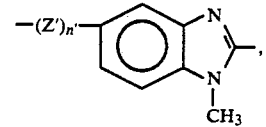

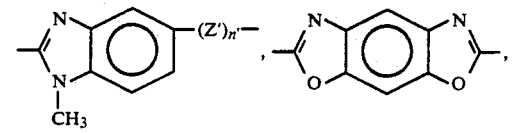

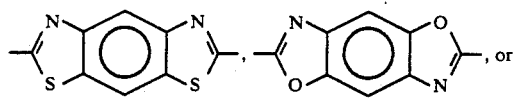

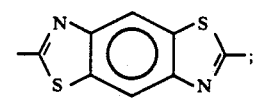

$Z^2$ is a group represented by a cyclic or bicyclic ring system containing from 5 to about 12 carbon atoms and is cycloaliphatic, polycycloaliphatic, aromatic or a combination thereof; n is 0 to 2; each $Z'$ is independently a —CO—, —O—CO—, —CO—O—, —CO—NR$^1$—, or —NR$^1$—CO— group and each n' independently has a value of zero or one;

with the proviso that each $Z^1$ can also independently be

—CR$^1$=C—, —C=CR$^1$—,
    |         |
   C≡N     C≡N

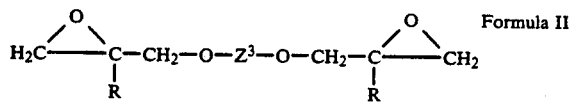
—CR¹=N—, —N=CR¹—, —CO—CR¹=CR¹—, —CR¹=CR¹—CO—, —CO—O—, and —O—CO— when Z² is not a benzene ring and when n≠0;

or the following Formula II

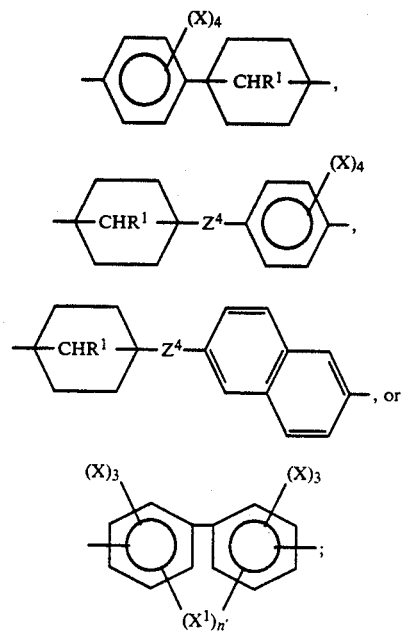

Formula II wherein Z³ is and Z⁴ is —CO—O—, —O—CO—, —NR¹—CO— or —CO—NR¹—; X¹ is a divalent is a divalent hydrocarbyl group having from 1 to about 10 carbon atoms which can contain one or more heteroatoms selected from N, O or S and is saturated or unsaturated; each R and R¹ is independently hydrogen or an aliphatic hydrocarbon group having from 1 to about 4 carbon atoms; each X is independently hydrogen, a hydrocarbyl or hydrocarbyloxy group having from 1 to about 12 carbon atoms, a halogen atom, —NO₂, or —C≡N; and n' is zero or one; or any combination of any two or more epoxy resins represented by the aforementioned Formulas I or II; with (B) at least one compound having an average of more than one active hydrogen atom per molecule selected from the group consisting of bisphenols, thiobisphenols, dicarboxylic acids and compounds containing one primary amine or amide group or two secondary amine groups; and wherein (a) components (A) and (B) are employed in quantities which provide a ratio of active hydrogen atoms per epoxide group of from about 0.01:1 to about 0.95:1; and (b) the reactants are meltable or soluble under conditions necessary for their derivatization or further reaction; and (II) a curing quantity of at least one curing agent therefor.

2. A curable composition of claim 1 wherein
(a) when component (A) is an epoxy resin represented by Formula I, in which X is a hydrocarbyl or hydrocarbyloxy group, it has from 1 to about 6 carbon atoms and when it is a halogen atom, it is chlorine or bromine;
(b) when component (A) is an epoxy resin represented by Formula II, in which X is a hydrocarbyl or hydrocarbyloxy group, it has from 1 to about 6 carbon atoms and when it is a halogen atom, it is chlorine or bromine;
(c) component (B) is a compound represented by the following Formulas XVII or XVIII

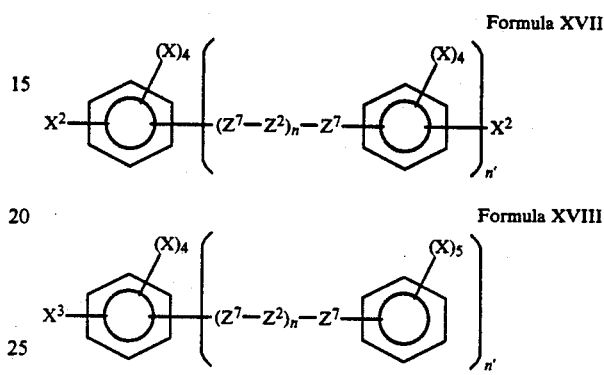

wherein X² is independently a hydroxyl, carboxylic acid, —SH, or —NHR² group; R² is an alkyl group having from 1 to about 4 carbon atoms; X³ is NH₂—, NH₂—SO₂—, NH₂—CO—, or NH₂—Z⁸—O—; Z⁸ is an alkyl or cycloalkyl group having from 1 to about 12 carbon atoms; Z⁷ can independently be a divalent hydrocarbyl group having from 1 to about 10 carbon atoms, —O—, —CO—, —SO—, —SO₂—, —S—, —S—S—, —CR¹=CR¹—, —CR¹=CR¹—CR¹=CR¹—, —CR¹=N—N=CR¹—, —CR¹=CR¹—CO—O—CH₂—, —CR¹=CR¹—CO—CH₂—CH₂—, —CH₂—O—CO—CR¹=CR¹—, —CH₂—CH₂—O—CO—CR¹=CR¹—, —CR¹=CR¹—CO—O—, —O—CO—CR¹=CR¹—, —N≡N—, —CO—NR¹—, —NR¹—CO—, —CO—NR¹—NR¹—CO—, —C≡C—, —C≡C—C≡C—, —CO—S—, —S—CO—, —CR¹=N—, —N=CR¹—, —CO—O—, —O—CO—, —CR¹=CR¹—CO—, —CO—CR¹=CR¹—, —CR¹=CR¹—O—CO—CH₂—, —CH₂—CO—O—CR¹=CR¹—, —CR¹=CR¹—O—CO—CH₂—CH₂—, —CH₂—CH₂—CO—O—CR¹=CR¹—, —CH₂—CH₂—CO—O—, —O—CO—CH₂—CH₂—, —CO—O—CR¹=CR¹—, —CR¹=CR¹—O—CO—, a direct single bond,

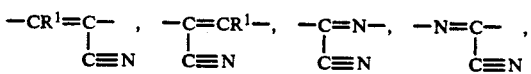

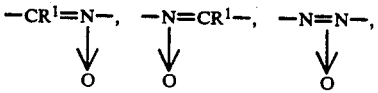

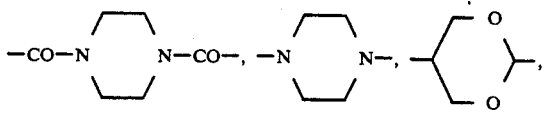

-continued

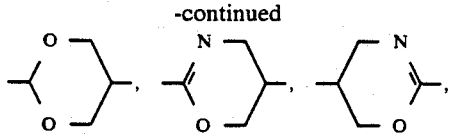

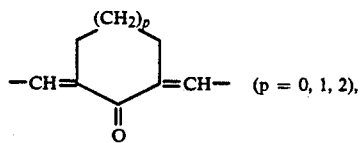 (p = 0, 1, 2),

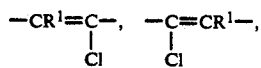

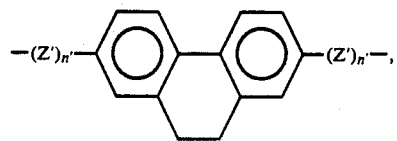

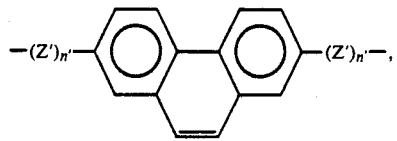

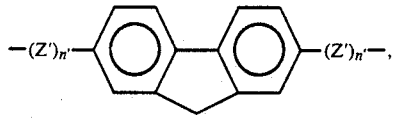

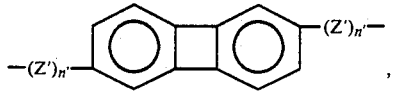

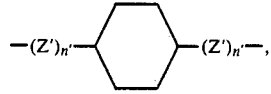

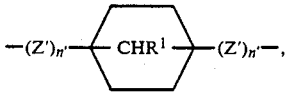

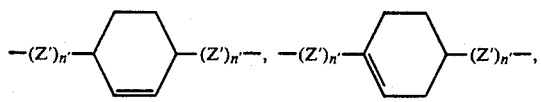

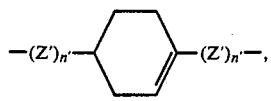

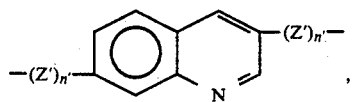

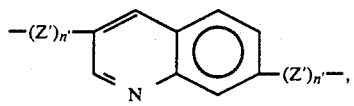

-continued

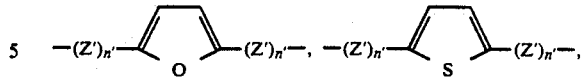

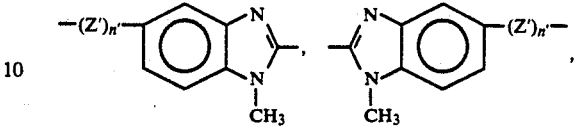

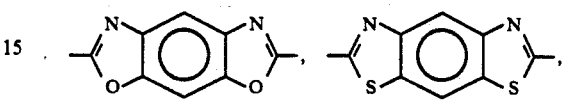

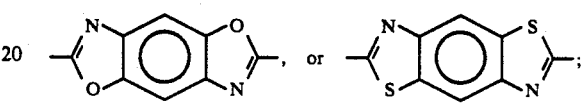

and each X is independently hydrogen, a hydrocarbyl or hydrocarbyloxy group having from 1 to about 12 carbon atoms, a halogen atom, $-NO_2$ or $-C\equiv N$; $Z^2$ is a group represented by a cyclic or bicyclic ring system is containing from 5 to about 12 carbon atoms and is cycloaliphatic, polycycloaliphatic, aromatic or a combination thereof; n is zero to 2; each Z' is independently a $-CO-$, $-O-CO-$, $-CO-O-$, $-CO-NR^1-$, or $-NR^1-CO-$ group; each $R^1$ is independently hydrogen or an aliphatic hydrocarbon group having from 1 to about 4 carbon atoms and each n' independently has a value of zero or one; or any combination of any two or more compounds represented by the aforementioned Formulas XVII and XVIII; and (d) components (A) and (B) are employed in amounts which provide a ratio of active hydrogen atoms per epoxide group of from about 0.05:1 to about 0.8:1.

3. A curable composition of claim 2 wherein (a) when component (A) is an epoxy resin represented by Formula I, X is a hydrocarbyl or hydrocarbyloxy group, it has from 1 to about 4 carbon atoms and when it is a halogen atom, it is bromine (b) when component (A) is an epoxy resin represented by Formula II, X is a hydrocarbyl or hydrocarbyloxy group, it has from 1 to about 4 carbon atoms and when it is a halogen atom, it is bromine; and (c) in component (B), X is a hydrocarbyl or hydrocarbyloxy group, it has from 1 to about 4 carbon atoms and when it is a halogen atom, it is chlorine or bromine.

4. A curable composition of claim 1 wherein (a) component (B) is hydroquinone, bisphenol A, 4,4'-dihydroxydiphenylmethane, 4,4'-thiodiphenol, 4,4'-sulfonyldiphenol, 4,4'-dihydroxydiphenyl oxide, 4,4'-dihydroxybenzophenone, 1,1-bis(4-hydroxyphenyl)-1-phenylethane, 3,3',5,5'-tetrachlorobisphenol A, 3,3'-dimethoxybisphenol A, 4,4'-dihydroxybiphenyl, 4,4'-dihydroxy-α,α'-diethylstilbene, 4,4'-dihydroxy-α-methylstilbene, 4,4'-dihydroxybenzanilide, 4,4'-dihydroxy-2,2'-dimethylazoxybenzene, 4,4'-dihydroxy-α-cyanostilbene, bis(4-hydroxyphenyl)terephthalate, N,N'-bis(4-hydroxyphenyl)terephthalamide, bis(4'-hydroxybiphenyl)terephthalate, 4,4'-dihydroxyphenylbenzoate, bis(4'-hydroxyphenyl)-1,4-benzenediimine, 4,4''-dihydroxybiphenylbenzoate, 1,4-bis(41-hydroxyphenyl-1'-carboxamide)benzene, 1,4-bis(4'-hydroxyphenyl-1'-carboxy)benzene, 4,4'-bis(4''-hydroxyphenyl-1''-carboxy)biphenyl, terephthalic acid, 4,4'-benzanilide dicarboxylic acid, 4,4'-phenylbenzoate dicarboxylic acid, 4,4'-stilbenedicarboxylic acid, aniline, 4'-sulfonamido-N-phenylbenzamide, 4'-sulfonamido-N'-phenyl-4-chlorobenzamide, 4-amino-1-phenylbenzoate, 4-amino-N-phenylbenzamide, N-phenyl-4-aminophenyl-1-carboxamide, phenyl-4-aminobenzoate, biphenyl-4-aminobenzoate, 1-phenyl-4'-aminophenylterephthalate and mixtures thereof; and (b) components (A) and (B) are employed in amounts which provide a ratio of active hydrogen atoms per epoxide group of from about 0.1:1 to about 0.5:1.

5. A curable composition of claim 3 wherein
(a) component (B) is hydroquinone, bisphenol A, 4,4'-dihydroxydiphenylmethane, 4,4'-thiodiphenol, 4,4'-sulfonyldiphenol, 4,4'-dihydroxydiphenyl oxide, 4,4'-dihydroxybenzophenone, 1,1-bis(4-hydroxyphenyl)-1-phenylethane, 3,3',5,5'-tetrachlorobisphenol A, 3,3'-dimethoxybisphenol A, 4,4'-dihydroxybiphenyl, 4,4'-dihydroxy-α,α'-diethylstilbene, 4,4'-dihydroxy-α-methylstilbene, 4,4'-dihydroxybenzanilide, 4,4'-dihydroxy-2,2'-dimethylazoxybenzene, 4,4'-dihydroxy-α-cyanostilbene, bis(4-hydroxyphenyl)terephthalate, N,N'-bis(4-hydroxyphenyl)terephthalamide, bis(4'-hydroxybiphenyl)terephthalate, 4,4'-dihydroxyphenylbenzoate, bis(4'-hydroxyphenyl)-1,4-benzenediimine, 4,4''-dihydroxybiphenylbenzoate, 1,4-bis(4'-hydroxyphenyl-1'-carboxamide)benzene, 1,4-bis(4'-hydroxyphenyl-1'-carboxy)benzene, 4,4'-bis(4''-hydroxyphenyl-1''-carboxy)biphenyl, terephthalic acid, 4,4'-benzanilide dicarboxylic acid, 4,4'-phenylbenzoate dicarboxylic acid, 4,4'-stilbenedicarboxylic acid, aniline, 4'-sulfonamido-N-phenylbenzamide, 4'-sulfonamido-N'-phenyl-4-chlorobenzamide, 4'-amino-1-phenylbenzoate, 4-amino-N-phenylbenzamide, N-phenyl-4-aminophenyl-1-carboxamide, phenyl-4-aminobenzoate, biphenyl-4-aminobenzoate, 1-phenyl-4'-aminophenylterephthalate and mixtures thereof; and (b) components (A) and (B) are employed in amounts which provide a ratio of active hydrogen atoms per epoxide group of from about 0.1:1 to about 0.5:1.

6. A curable composition comprising (I) a blend comprising
(A) an advanced epoxy resin composition prepared by reacting
(1) one or more epoxy resins containing one or more rodlike mesogenic moieties, said epoxy resin being those represented by either the following Formula I

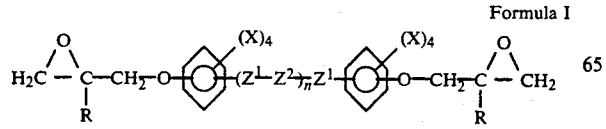

Formula I wherein at least about 80 percent of the $-(Z^1-Z^2)_n-Z^1-$ linkages and the glycidyl ether groups are in the para position with respect to each other; each R and $R^1$ is independently hydrogen or an aliphatic hydrocarbon group having from 1 to about 4 carbon atoms; each X is independently hydrogen, a hydrocarbyl or hydrocarbyloxy group having from 1 to about 12 carbon atoms, a halogen atom, $-NO_2$, or $-C\equiv N$; each $Z^1$ is independently $-CR^1=CR^1-$, $-CR^1=CR^1-CR^1=CR^1-$, $-CR^1=N-N=CR^1$, $-CR^1=C-R^1-CO-O-CH_2-$, $-CR^1=C-R^1-CO-O-CH_2-CH_2-$, $-CH_2-O-CO-CR^1=CR^1-$, $-CH_2-CH_2-O-CO-CR^1=CR^1-$, $-CR^1=C-R^1-CO-O-$, $-O-CO-CR^1=CR^1-$, $-CO-NR^1-$, $-NR^1-CO-$, $-CO-NR^1-NR^1-CO-$, $-C\equiv C-$, $-C\equiv C-C\equiv C-$, $-N=N-$, $-CO-S-$, $-S-CO-$, $-CR^1=CR^1-O-CO-CH_2-$, $-CH_2-CO-O-CR^1=CR^1-$, $-CR^1=C-R^1-O-CO-CH_2-CH_2-$, $-CH_2-CH_2-CO-O-CR^1=CR^1-$, $-CH_2-CH_2-CO-O-$, $-O-CO-CH_2-CH_2-$, $-CO-O-CR^1=CR^1-$, $-CR^1=C-R^1-O-CO-$, a direct single bond when $n \geq 1$,

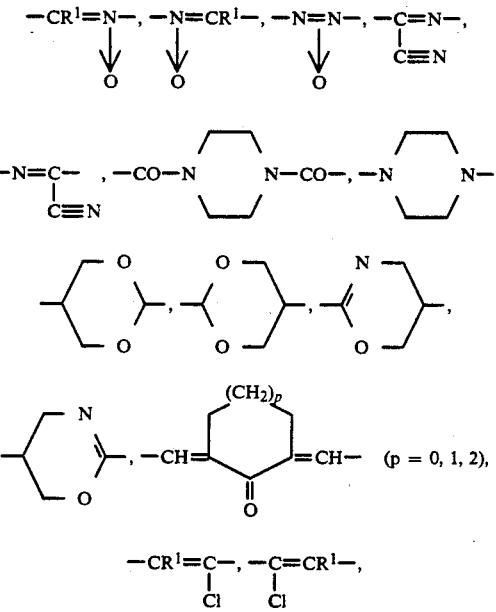

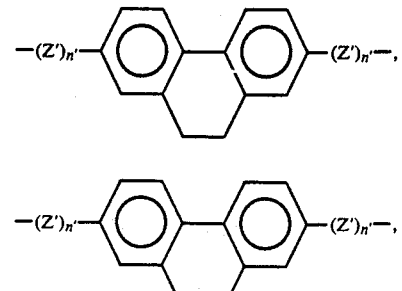

-continued

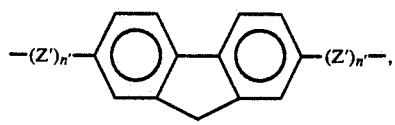

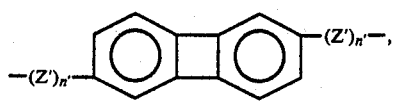

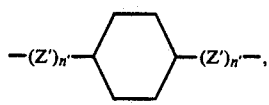

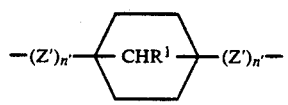

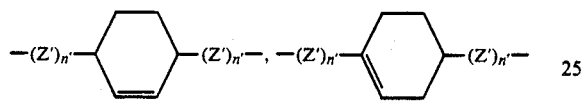

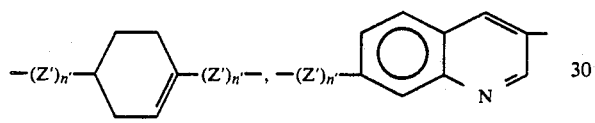

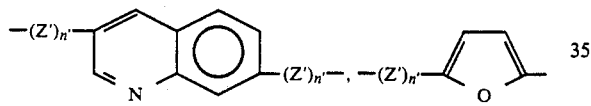

Z² is a group represented by a cyclic or bicyclic ring system containing from 5 to about 12 carbon atoms and is cycloaliphatic, polycycloaliphatic, aromatic or a combination thereof; n is 0 to 2; each Z' is independently a —CO—, —O—CO—, —CO—O—, —CO—NR¹—, or —NR¹—CO— group and each n' independently has a value of zero or one;

with the proviso that each Z¹ can also independently be

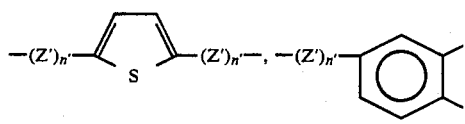

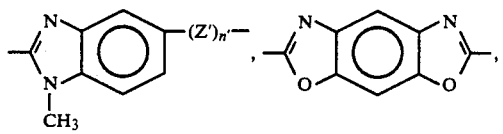

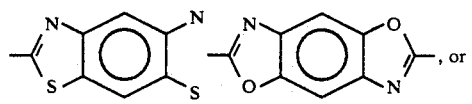

-continued

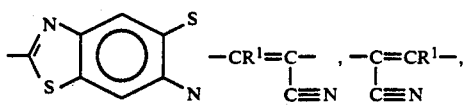

—CR¹=N—, —N=CR¹—, —CO—CR¹=CR¹—, —CR¹=CR¹—CO—, —CO—O—, and —O—CO— when Z² is not a benzene ring and when n≠0;

or the following Formula II

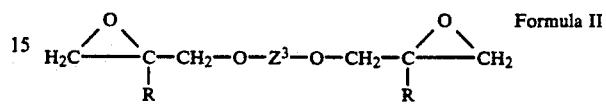

wherein Z³ is

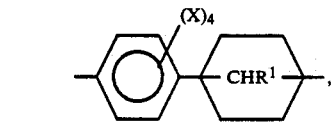

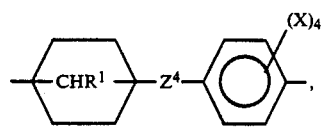

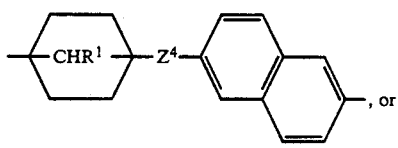

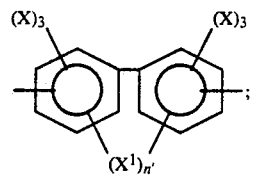

and Z⁴ is —CO—O—, —O—CO—, —NR¹—CO— or —CO—NR¹—; X¹ is a divalent hydrocarbyl group having from 1 to about 10 carbon atoms which can contain one or more heteroatoms selected from N, O or S and is saturated or unsaturated; each R and R¹ is independently hydrogen or an aliphatic hydrocarbon group having from 1 to about 4 carbon atoms; each X is independently hydrogen, a hydrocarbyl or hydrocarbyloxy group having from 1 to about 12 carbon atoms, a halogen atom, —NO₂, or —C≡N; and n' is zero or one; or any combination of any two or more epoxy resins represented by the aforementioned Formulas I or II; with (2) at least one compound having an average or more than one active hydrogen atom per molecule selected from the group consisting of bisphenols, thiobisphenols, dicarboxylic acids and compounds containing one primary amine or amide group or two secondary amine groups; and wherein (a) components (A-1) and (A-2) are employed in quantities which provide a ratio of active hydrogen atoms per epoxide group of from about 0.01:1 to about 0.95:1; and (b) the reactants are meltable or soluble under conditions necessary for their derivatization or further reaction; and (B) one or more polyepoxides which are substantially free of rodlike mesogenic moieties; and (II) a curing quantity of at least one curing agent therefor.

7. A curable composition of claim 6 wherein;
(a) when component (A-1) is an epoxy resin represented by Formulas I or II and when X therein is a hydrocarbyl or hydrocarbyloxy group, it has from 1 to about 6 carbon atoms and when it is a halogen atom, it is chlorine or bromine;
(b) component (B) is an epoxy resin represented by the following Formulas V, VI, VII, VIII, IX, X or XI Formula V
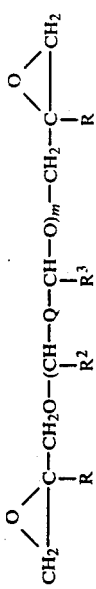
Formula VI
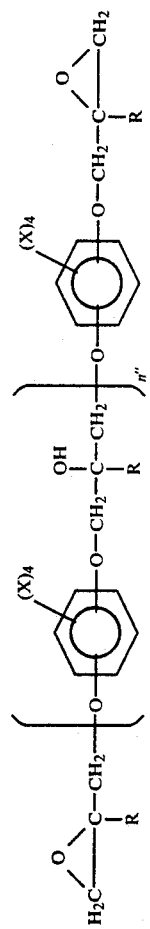
Formula VII
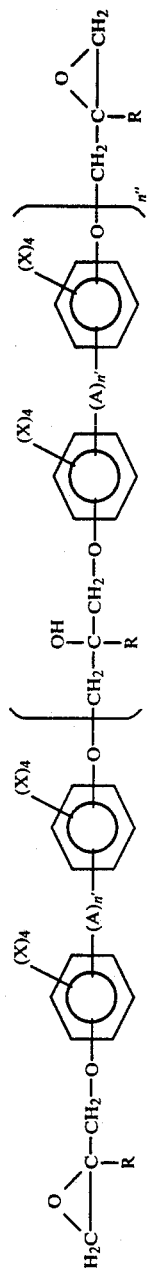
Formula VIII
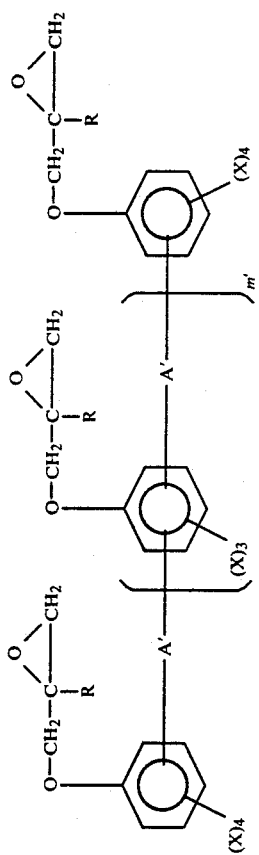
Formula IX
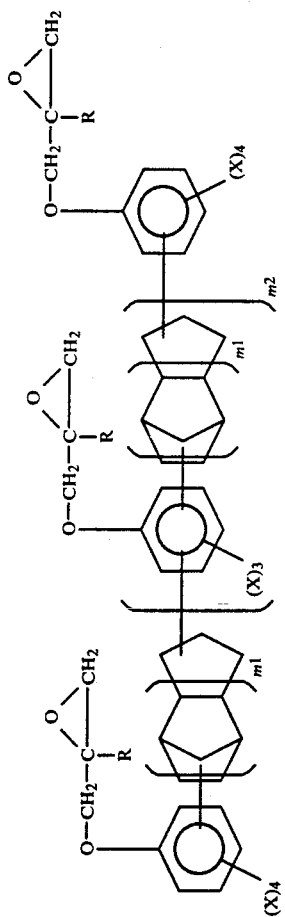

-continued
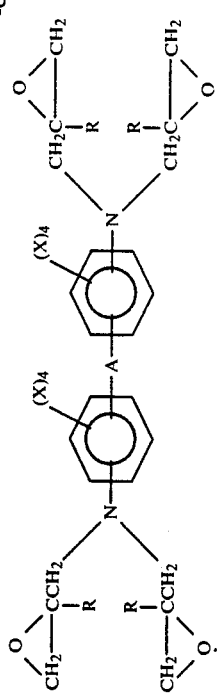
Formula X
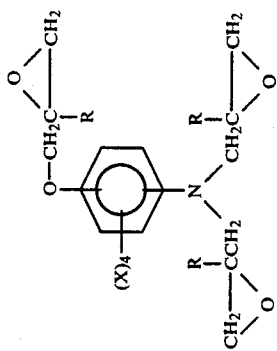
Formula XI wherein each A is independently a divalent hydrocarbyl group having from 1 to about 12 carbon atoms, —O—, —S—, —S—S—, —SO—, —SO₂—, or —CO—; each A' is independently a divalent hydrocarbon group having from 1 to about 6 carbon atoms; Q is a single bond, —CH₂—S—CH₂—, —(CH₂)$_{n1}$—, or

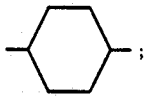

each R is independently hydrogen or an alkyl group having from 1 to about 4 carbon atoms; each R² and R³ is independently hydrogen, a hydrocarbyl or halohydrocarbyl group having from 1 to about 6 carbon atoms; each X is independently hydrogen, a hydrocarbyl or hydrocarbyloxy group having from 1 to about 12 carbon atoms, a halogen atom, —NO₂ or —C≡N; m has a value from about 1 to about 10; m' has an average value from about 0.01 to about 12; m¹ has an average value from about 1 to about 12; m² has a value from about 1 to about 12; n' has a value of zero or 1; n" has an average value from about zero to about 3 and n' has an average value from about 1 to about 10;

(c) components (A-1) and (A-2) are employed in amounts which provide a ratio of active hydrogen atoms per epoxide group of from about 0.05:1 to about 0.8:1;

(d) component (A) is present in an amount of from about 1 to about 99 percent by weight based on the combined quantities of components (A) and (B); and (e) component (B) is present in an amount of from about 99 to about 1 percent by weight based on the combined quantities of components (A) and (B).

8. A curable composition of claim 7 wherein;

(a) when component (A-]) is an epoxy resin represented by Formulas I or II and when X therein is a hydrocarbyl or hydrocarbyloxy group, it has from 1 to about 4 carbon atoms and when it is a halogen atom, it is bromine;

(b) component (A-2) is a compound represented by the following Formulas XVII or XVIII Formula XVII

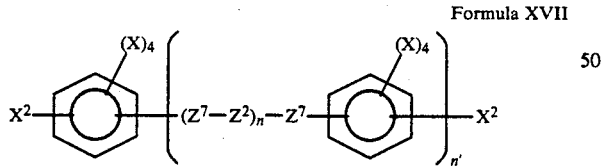

Formula XVIII

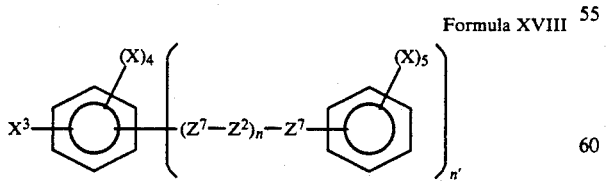

wherein X² is independently a hydroxyl, carboxylic acid, —SH, or —NHR² group; R² is an alkyl group having from 1 to about 4 carbon atoms; X³ is NH₂—, NH₂—SO₂—, NH₂—CO—, or NH₂—Z⁸—O—; Z⁸ is an alkyl or cycloalkyl group having from 1 to about 12 carbon atoms; Z⁷ can independently be a divalent hydrocarbyl group having from 1 to about 10 carbon atoms, —O—, —CO—, —SO—, —SO₂—, —S—, —S—S—, —CR¹=CR¹—, —CR¹=CR¹—CR¹=CR¹—, —CR¹=N—N=CR¹—, —CR¹=CR¹—CO—O—CH₂, —CR¹=CR¹—CO—CH₂—CH₂—, —CH₂—O—CO—CR¹=CR¹—, —CH₂—O—CO—CR¹=CR¹—, —CR¹=CR¹—CO—O—, —O—CO—CR¹=CR¹—, —N=N—, —CO—NR¹—, —NR¹—CO—, —CO—NR¹—NR¹—CO—, —C≡C—, —C≡C—C≡C—, —CO—S—, —S—CO—, —CR¹=N—, —N=CR¹—, —CO—O—, —O—CO—, —CR¹=CR¹—CO—, —CO—CR¹=CR¹—, —CR¹=CR¹—O—CO—CH₂—, —CH₂—CO—O—CR¹=CR¹—, —CR¹=CR¹—O—CO—CH₂—CH₂—, —CH₂—CH₂—CO—O—CR¹=CR¹—, —CH₂—CH₂—CO—O—, —O—CO—CH₂—CH₂—, —CO—O—CR¹=CR¹—, —CR¹=CR¹—O—CO—, a direct single bond,

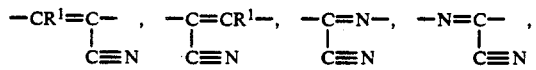

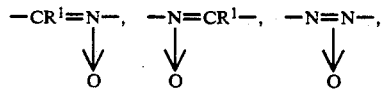

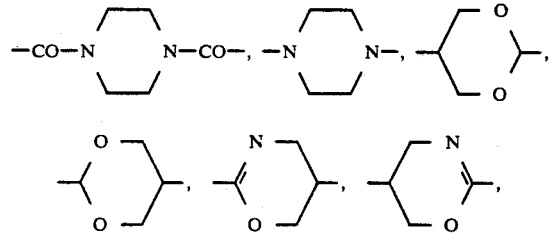

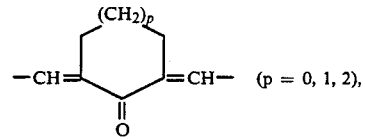

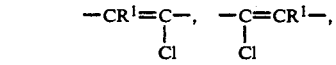

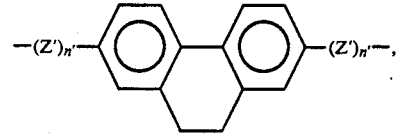

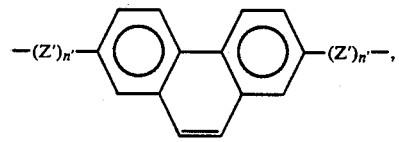

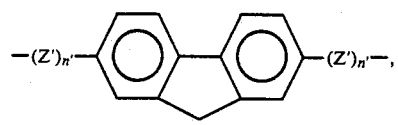

or hydrocarbyloxy group having from 1 to about 12 carbon atoms, a halogen atom, —NO$_2$ or —C≡N; Z$^2$ is a group represented by a cyclic or bicyclic ring system containing from 5 to about 12 carbon atoms and is cycloaliphatic, polycycloaliphatic, aromatic or a combination thereof; n is zero to 2; each Z' is independently a —CO—, —O—CO—, —CO—O—, —CO—NR$^1$—, or —NR$^1$—CO— group; each R$^1$ is independently hydrogen or an aliphatic hydrocarbon group having from 1 to about 4 carbon atoms and each n' independently has a value of zero or one; or any combination of any two or more compounds represented by the aforementioned Formulas XVII and XVIII;

(c) components (A-1) and (A-2) are employed in amounts which provide a ratio of active hydrogen atoms per epoxide group of from about 0.05:1 to about 0.8:1;

(d) component (A) is present in an amount of from about 10 to about 80 percent by weight based on the combined quantities of components (A) and (B); and (e) component (B) i3 present in an amount of from about 90 to about 20 percent by weight based on the combined quantities of components (A) and (B).

9. A curable composition of claim 6 wherein (a) component (B) is hydroquinone, bisphenol A, 4,4'-dihydroxydiphenylmethane, 4,4'-thiodiphenol, 4,4'-sulfonyldiphenol, 4,4'-dihydroxydiphenyl oxide, 4,4'-dihydroxybenzophenone, 1,1-bis(4-hydroxyphenyl)-1-phenylethane, 3,3',5,51-tetrachlorobisphenol A, 3,3'-dimethoxybisphenol A, 4,4'-dihydroxybiphenyl, 4,4'-dihydroxy-α,α'-diethylstilbene, 4,4'-dihydroxy-α-methylstilbene, 4,4'-dihydroxybenzanilide, 4,4'-dihydroxy-2,2'-dimethylazoxybenzene, 4,4'-dihydroxy-α-cyanostilbene, bis(4-hydroxyphenyl)terephthalate, N,N'-bis(4-hydroxyphenyl)terephthalamide, bis(4'-hydroxybiphenyl)terephthalate, 4,4'-dihydroxyphenylbenzoate, bis(4'-hydroxyphenyl)-1,4-benzenediimine, 4,4''-dihydroxybiphenylbenzoate, 1,4-bis(4'-hydroxyphenyl-1'-carboxamide)benzene, 1,4-bis(4'-hydroxyphenyl-1'-carboxy)benzene, 4,4'-bis(4''-hydroxyphenyl-1''-carboxy)biphenyl, terephthalic acid, 4,4'-benzanilide dicarboxylic acid, 4,4'-phenylbenzoate dicarboxylic acid, 4,4'-stilbenedicarboxylic acid, aniline, 4'-sulfonamido-N-phenylbenzamide, 4'-sulfonamido-N'-phenyl-4-chlorobenzamide, 4-amino-1-phenylbenzoate, 4-amino-N-phenylbenzamide, N-phenyl-4-aminophenyl-1-carboxamide, phenyl-4-aminobenzoate, biphenyl-4-aminobenzoate, 1-phenyl-4'-aminophenylterephthalate and mixtures thereof;

(b) components (A-1) and (A-2) are employed in amounts which provide a ratio of active hydrogen atoms per epoxide group of from about 0.1:1 to about 0.5:1;

(e) component (A) is present in an amount of from about 10 to about 50 percent by weight based on the combined quantities of components (A) and (B); and (d) component (B) is present in an amount of from about 90 to about 50 percent by weight based on the combined quantities of components (A) and (B).

10. A curable composition of claim 7 wherein (a) component (B) is hydroquinone, bisphenol A, 4,4'-dihydroxydiphenylmethane, 4,4'-thiodiphenol, 4,4'-sulfonyldiphenol, 4,4'-dihydroxydiphenyl oxide, 4,4'-dihydroxybenzophenone, 1,1-bis(4-hydroxyphenyl)-1-phenylethane, 3,3',5,51-tetrachlorobisphenol A, 3,3'-dimethoxybisphenol A, 4,4'-dihydroxybiphenyl, 4,4'-dihydroxy-α,α'-diethylstilbene, 4,4'-dihydroxy-α-methylstilbene, 4,4'-dihydroxybenzanilide, 4,4'-dihydroxy-2,2'-dimethylazoxybenzene, 4,4'-dihydroxy-α-cyanostilbene, bis(4-hydroxyphenyl)terephthalate, N,N'-bis(4-hydroxyphenyl)terephthalamide, bis(4'-hydroxybiphenyl)terephthalate, 4,4'-dihydroxyphenylbenzoate, bis(4'-hydroxyphenyl)-1,4-benzenediimine, 4,4''-dihydroxybiphenylbenzoate, 1,4-bis(4'-hydroxyphenyl-1'-carboxamide)benzene, 1,4-bis(4'-hydroxyphenyl-1'-carboxy)benzene, 4,4'-bis(4''-hydroxyphenyl-1''-carboxy)biphenyl, terephthalic acid, 4,4'-benzanilide dicarboxylic acid, 4,4'-phenylbenzoate dicarboxylic acid, 4,4'-stilbenedicarboxylic acid, aniline, 4'-sulfonamido-N-phenylbenzamide, 4'-sulfonamido-N'-phenyl-4-chlorobenzamide, 4-amino-1-phenylbenzoate, 4-amino-N-phenylbenzamide, N-phenyl-4-aminophenyl-1-carboxamide, phenyl-4-aminobenzoate, biphenyl-4-aminobenzoate, 1-phenyl-4'-aminophenylterephthalate and mixtures thereof; and (b) components (A-1) and (A-2) are employed in amounts which provide a ratio of active hydrogen atoms per epoxide group of from about 0.1:1 to about 0.5:1.;

(c) component (A) is present in an amount of from about 10 to about 50 percent by weight based on the combined quantities of components (A) and (B); and (d) component (B) is present in an amount of from about 90 to about 50 percent by weight based on the combined quantities of components (A) and (B).

11. A curable composition of claim 1, 2, 3, 4, 5, 6, 7, 8, 9 or 10 wherein said curing agent is an aromatic amine, cycloaliphatic amine, aliphatic amine, carboxylic acid, carboxylic acid anhydride, imidazole, aromatic hydroxyl-containing compound, guanidine or a combination thereof.

12. A curable composition of claim 11 wherein said curing agent is sulfanilamide, diaminodiphenylsulfone, methylenedianiline, isophoronediamine, diaminocyclohexane, 2,5-dimethyl-2,5-hexanediamine, hexamethylenediamine, phthalic anhydride, methylimidazole, methylethylimidazole, phenol-formaldehyde novolac resin, or a combination thereof.

13. The product resulting from curing the curable composition of claim 11.

14. The product of claim 13 wherein said curable composition is subjected to the application of an electric field, magnetic field, drawing and/or shear flow prior to and/or during curing.

15. The product resulting from curing the curable composition of claim 12.

16. The product of claim 15 wherein said curable composition is is subjected to the application of an electric field, magnetic field, drawing and/or shear flow prior to and/or during curing.

* * * * *

UNITED STATES PATENT AND TRADEMARK OFFICE
CERTIFICATE OF CORRECTION

PATENT NO. : 5,270,404  
DATED : December 14, 1993  
INVENTOR(S) : Jimmy D. Earls, et al Page 1 of 3

It is certified that error appears in the above-indentified patent and that said Letters Patent is hereby corrected as shown below:

On the title page, Item [56]:
    under Other Publications, after Chapter 17, delete "00." and after the word at, "th" should read --the--.

under Other Publications, after Derwent Abstracts: 90-143153/19, delete " "Handbook of "

under Other Publications, in front of Epoxy insert--"Handbook of--.

In claim 1, column 71, lines 40 & 41, delete "is a divalent".

In claim 2, column 72, line 43, : "-N≡N-" should read -- -N=N- --.

In claim 2, column 74, line 27, before N, "-" should be deleted.

In claim 2, column 74, line 28, delete "is".

UNITED STATES PATENT AND TRADEMARK OFFICE
CERTIFICATE OF CORRECTION

PATENT NO. : 5,270,404
DATED : December 14, 1993
INVENTOR(S) : Jimmy D. Earls, et al It is certified that error appears in the above-indentified patent and that said Letters Patent is hereby corrected as shown below:

In claim 4, column 75, line 7, "41" should read --4'--.

In claim 6, column 77, line 65, the formula should read

--

--.

In claim 6, column 78, line 62, "or" should be --of--.

UNITED STATES PATENT AND TRADEMARK OFFICE
CERTIFICATE OF CORRECTION

PATENT NO. : 5,270,404
DATED : December 14, 1993
INVENTOR(S) : Jimmy D. Earls, et al It is certified that error appears in the above-indentified patent and that said Letters Patent is hereby corrected as shown below:

In claim 7, line 26, column 85, "n'" should be --$n^1$--.

In claim 8, line 40, column 85, "(A-])" should read --(A-1)--.

In claim 8, line 10, column 86, "-N≡N-," should read -- -N=N-, --.

In claim 8, line 11, column 88, "i3" should read --is--.

In claim 9, line 21, column 88, "51" should read --5'--.

In claim 9, line 49, column 88, "(e)" should read --(c)--.

In claim 10, line 63, column 88, "51" should read --5'--.

Signed and Sealed this

Sixth Day of September, 1994

Attest:

BRUCE LEHMAN

*Attesting Officer*     *Commissioner of Patents and Trademarks*